US008193528B2

(12) United States Patent
Schäfer et al.

(10) Patent No.: US 8,193,528 B2
(45) Date of Patent: Jun. 5, 2012

(54) AZAPYRENES FOR ELECTRONIC APPLICATIONS

(75) Inventors: Thomas Schäfer, Liestal (CH); Thomas Eichenberger, Basel (CH); Kristina Bardon, Waldshut (DE); Andrea Ricci, Zürich (CH); Natalia Chebotareva, Hagenthal le Bas (FR)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/003,614

(22) PCT Filed: Jun. 23, 2009

(86) PCT No.: PCT/EP2009/057754
§ 371 (c)(1),
(2), (4) Date: Mar. 7, 2011

(87) PCT Pub. No.: WO2010/006890
PCT Pub. Date: Jan. 21, 2010

(65) Prior Publication Data
US 2011/0186821 A1    Aug. 4, 2011

(30) Foreign Application Priority Data

Jul. 18, 2008   (EP) ..................... 08160714

(51) Int. Cl.
*H01L 35/24* (2006.01)
(52) U.S. Cl. .............. 257/40; 257/13; 257/79; 544/248; 544/247; 544/249; 544/245
(58) Field of Classification Search .................... 257/13, 257/40, 79; 544/248, 247, 249, 245
See application file for complete search history.

(56) References Cited

U.S. PATENT DOCUMENTS

2004/0076853 A1   4/2004 Jarikov

OTHER PUBLICATIONS

Borolvlev, Chem. of Heterocyclic Compounds, vol. 38, No. 8 (2002) pp. 968-973.
Riehm et al., Chamistry:A European Journal, vol. 13,(2007) pp. 7317-7329.
Aksenov et al., Tetrahedron Letters, vol. 49, No. 4 (Jan. 4, 2008) pp. 707-709.
Aksenova et al. Chem. of Heterocyclic Compounds, vol. 43, No. 5 (May 1, 2007) pp. 665-666.
Jie Hu, Journal of Organic Chemistry, Vol. 70, (Dec. 16, 2004) pp. 707-708.

*Primary Examiner* — Long Pham
(74) *Attorney, Agent, or Firm* — Qi Zhuo

(57) ABSTRACT

The present invention relates to electronic devices, especially electroluminescent devices, comprising azapyrenes of formula (I), or formula (III), wherein $Y^1, Y^2, Y^3, Y^4, X^1, X^2$ and $X^3$ are independently each other N, or $CR^4$, with the proviso that at least one of the groups $X^1, X^2$ and $X^3$ is a group $CR^4$, $R^1$ is hydrogen, F, $-SiR^{100}R^{101}R^{102}$, or an organic substituent, $R^4$ is hydrogen, F, $-SiR^{100}R^{101}R^{102}$, or an organic substituent, or any of the substituents $R^1$, $R^{1'}$ and $R^4$, which are adjacent to each other, together form an aromatic, or heteroaromatic ring, or ring system, which can optionally be substituted, m is an integer of 1 to 6, and $R^{100}$, $R^{101}$ and $R^{102}$ are independently of each other a $C_1$-$C_8$alkyl group, a $C_6$-$C_{24}$aryl group, or a $C_7$-$C_{12}$aralkyl group, which may optionally be substituted, and Q is a linking group; with the proviso that in the compound of formula (III) at least one of the substituents $R^1$, or $R^4$ is a group Q; especially as host for phosphorescent emitters, electron transporting materials, or emitter materials. The hosts may function with phosphorescent materials to provide improved efficiency, stability, manufacturability, or spectral characteristics of electroluminescent devices.

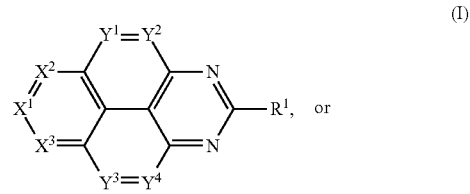

(I)

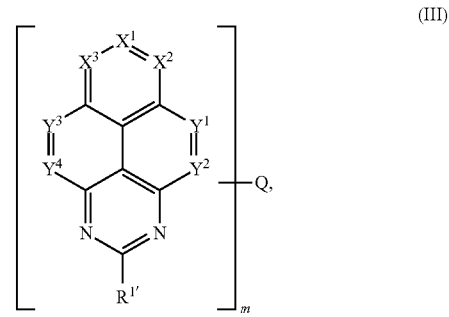

(III)

16 Claims, No Drawings

AZAPYRENES FOR ELECTRONIC APPLICATIONS

The present invention relates to electronic devices, especially electroluminescent devices, comprising azapyrenes, especially as host for phosphorescent emitters, electron transporting materials, or emitter materials. The hosts may function with phosphorescent materials to provide improved efficiency, stability, manufacturability, or spectral characteristics of electroluminescent devices.

Azapyrenes and the synthesis thereof are described, for example, in the following publications: A. V. Aksenov et al., Tetrahedron Letters (2008) 1808-1811; A. V. Aksenov et al., Tetrahedron Letters (2008) 707-709; I. V. Aksenova, et al., Chemistry of Heterocyclic Compounds (2007) 665-666; Till Riehm et al., Chemistry—A European Journal (2007) 7317-7329; I. V. Borovlev et al., Chemistry of Heterocyclic Compounds (2002) 968-973 and (2003) 1417-1442.

US2004076853 relates to an organic light-emitting device including a substrate, an anode and a cathode disposed over the substrate, and a luminescent layer disposed between the anode and the cathode wherein the luminescent layer includes a host and at least one dopant. The host of the luminescent layer is selected to include a solid organic material comprising a mixture of at least two components, one of which is capable of forming both monomer state and an aggregate state. The list of preferred heterocyclic compounds as materials for the first host component of the luminescent layer includes among others benzo[lmn][3,8]phenanthroline (2,7-diazapyrene):

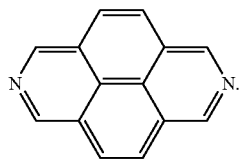

JP2255789 discloses an organic electroluminescent element having successively a positive pore injection and transportation layer, an emission layer and optionally a positive pore inhibitory layer on an anode and a cathode wherein at least one of the electrodes is transparent, a naphthalene derivative

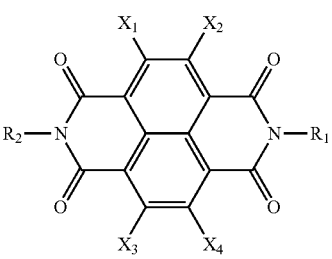

[e.g. 4,5-dimethoxynaphthalene-1,8-dicarboxylic acid (2' propyl)pentylimide,1,5-dicyanonaphthalene-4,8-dicarboxylic acid isobutyl ester] having 400-800 nm maximum fluorescent wavelength is used as an emission layer.

Notwithstanding these developments, there remains a need for EL devices comprising new electron transport, emitting and/or host materials, and especially hosts that will function with phosphorescent materials to provide improved efficiency, stability, manufacturability, and/or spectral characteristics of electroluminescent devices.

Accordingly, the present invention provides an electronic device, comprising a compound of formula

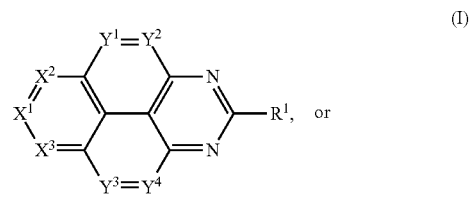

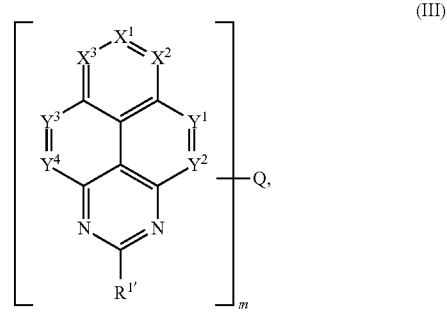

wherein
$Y^1, Y^2, Y^3, Y^4, X^1, X^2$ and $X^3$ are independently each other N, or $CR^4$,
with the proviso that at least one of the groups $X^1$, $X^2$ and $X^3$ is a group $CR^4$,
$R^1$ is hydrogen, F, $-SiR^{100}R^{101}R^{102}$, or an organic substituent,
$R^{1'}$ and $R^4$ are independently of each other hydrogen, F, $-SiR^{100}R^{101}R^{102}$ or an organic substituent, or
any of the substituents $R^{1'}$, $R^1$ and $R^4$, which are adjacent to each other, together form an aromatic, or heteroaromatic ring, or ring system, which can optionally be substituted,
m is an integer of 1 to 6, and
$R^{100}$, $R^{101}$ and $R^{102}$ are independently of each other a $C_1$-$C_8$alkyl group, a $C_6$-$C_{24}$aryl group, or a $C_7$-$C_{12}$aralkyl group, which may optionally be substituted, and Q is a linking group; with the proviso that in the compound of formula III at least one of the substituents $R^{1'}$, or $R^4$ is a group Q.

The compound of formula I is especially a compound of formula

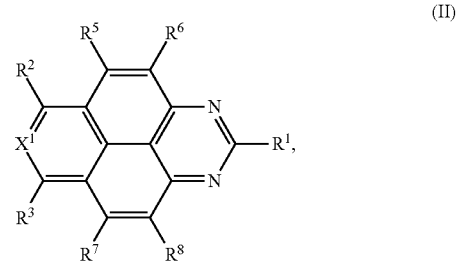

wherein $X^1$ is N, or $CR^4$,
$R^1$ is hydrogen, F, $-SiR^{100}R^{101}R^{102}$, or an organic substituent,
$R^2, R^3, R^4, R^5, R^6, R^7$ and $R^8$ are independently of each other hydrogen, F, $-SiR^{100}R^{101}R^{102}$, or an organic substituent, or any of the substituents $R^1$, $R^2$, $R^3$, $R^4$, $R^5$, $R^6$, $R^7$ and $R^8$, which are adjacent to each other, together form an aromatic, or heteroaromatic ring, or ring system, which can optionally be substituted, and $R^{100}$, $R^{101}$ and $R^{102}$ are as defined above.

The electronic device of the present invention is preferably an electroluminescent (EL) device. The compounds of formula I, or III may be used in organic light emitting diodes (OLEDs) as hosts for phosphorescent compounds, as emitting and/or electron transport material. The compounds of the present the invention can function in an organic electronic device including an organic solar cell, an organic photoconductor and an organic transistor, according to a principle similar to that applied to the organic light-emitting device. Besides organic light-emitting devices there are numerous other types of semiconductor devices. Common to all is the presence of one or more semiconductor materials. Semiconductor devices have been described, for example, by S. M. Sze in Physics of Semiconductor Devices, $2^{nd}$ edition, John Wiley and Sons, New York (1981). Such devices include rectifiers, transistors (of which there are many types, including p-n-p, n-p-n, and thin-film transistors), photoconductors, current limiters, thermistors, p-n junctions, field-effect diodes, Schottky diodes, and so forth. In each semiconductor device, the semiconductor material is combined with one or more metals or insulators to form the device. Semiconductor devices can be prepared or manufactured by known methods such as, for example, those described by Peter Van Zant in Microchip Fabrication, Fourth Edition, McGraw-Hill, New York (2000). A particularly useful type of transistor device, the thin-film transistor (TFT), in which the materials of the present invention can be used, generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, Physics of Semiconductor Devices, 2.sup.nd edition, John Wiley and Sons, page 492, New York (1981)). These components can be assembled in a variety of configurations. For example in an organic thin-film transistor (OTFT) has an organic semiconductor layer. Examples of such devices are described in WO2007/118799 and WO2009/047104.

For heterojunction solar cells (bulk heterojunction solar cells) the active (photoactive) layer comprise a mixture p-type and n-type organic semiconductors. In the active layer charge separation induced by light is occurring. Compounds of the formula I, or III can preferably be used as n-type semiconductor in such devices. Heterojunction solar cells comprise additional layers in the following order: a) a cathode (electrode), b) optionally a transition layer, such as an alkali halogenide, especially lithium fluoride, c) an active (photoactive) layer containing a compound of formula I, or III, d) optionally a smoothing layer, e) an anode (electrode), f) a substrate. Examples of such devices are described in WO2008/000664 and WO2009/047104.

$R^1$, $R^{1'}$, $R^2$, $R^3$, $R^4$, $R^5$, $R^6$, $R^7$ and $R^8$ are preferably hydrogen or an organic substituent.

The linking group Q is, for example an arylene, or heteroarylene group.

More preferred are compounds of formula II, wherein $X^1$ is N, or $CR^4$, $R^1$, $R^2$, $R^3$, $R^4$, $R^5$, $R^6$, $R^7$ and $R^8$ are independently of each other H, $C_1$-$C_{18}$alkyl, $C_1$-$C_{18}$alkyl which is substituted by E and/or interrupted by D, $C_1$-$C_{18}$ perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —CO—$R^{28}$, —CN, or a group -$L^1$-$NR^{25'}R^{26'}$,

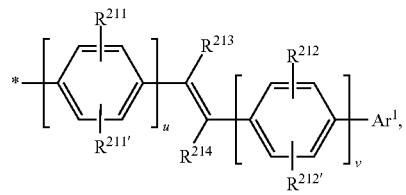

or a group -$L^1$-$NR^{25'}R^{26'}$,—wherein
u is 0, or 1; v is 0, or 1;
$R^{211}$, $R^{211'}$, $R^{212}$ and $R^{212'}$ are independently of each other H, $C_1$-$C_{18}$alkyl, or $C_1$-$C_{18}$alkoxy,
$R^{213}$ and $R^{214}$ are independently of each other H, or $C_1$-$C_{18}$alkyl,
$Ar^1$ is —$NR^{25'}R^{26'}$, $C_6$-$C_{24}$aryl, $C_6$-$C_{24}$aryl which is substituted by G, $C_2$-$C_{20}$heteroaryl, or $C_2$-$C_{20}$heteroaryl which is substituted by G;
wherein $R^{25'}$ and $R^{26'}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, or
$R^{25'}$ and $R^{26'}$ together with the nitrogen atom to which they are bonded form a heteroaromatic ring, or ring system, which may optionally be substituted;
$L^1$ is a single bond, or a bridging unit BU,
$R^5$ and $R^6$ and/or $R^7$ and $R^8$ together form a group

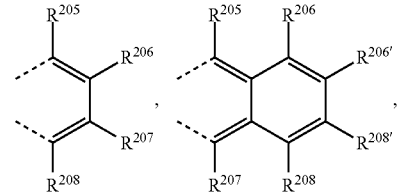

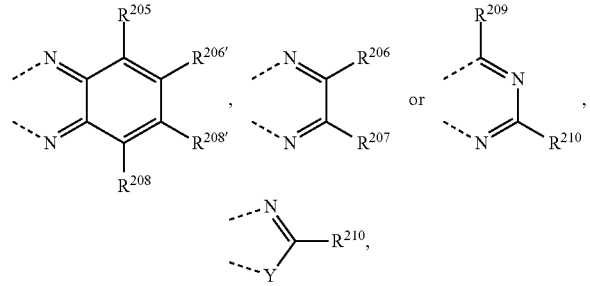

wherein $R^{206'}$, $R^{208'}$, $R^{205}$, $R^{206}$,
$R^{207}$, $R^{208}$, $R^{209}$ and $R^{210}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $C_1$-$C_{18}$ perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_7$-$C_{25}$aralkyl, CN, or —CO—$R^{28}$, Y is O, or N—R$^{25}$, D is —CO—; —COO—; —S—; —SO—; —SO$_2$—; —O—;
—NR$^{25}$—; —SiR$^{39}$R$^{31}$—; —POR$^{32}$—;
—CR$^{23}$=CR$^{24}$—; or —C≡C—; and E is —OR$^{29}$; —SR$^{29}$; —NR$^{25}$R$^{26}$; —COR$^{28}$; —COOR$^{27}$;
—CONR$^{25}$R$^{26}$; —CN; or halogen;

G is E, C$_1$-C$_{18}$alkyl, C$_1$-C$_{18}$alkyl which is interrupted by D, C$_1$-C$_{18}$ perfluoroalkyl, C$_1$-C$_{18}$alkoxy, or C$_1$-C$_{18}$alkoxy which is substituted by E and/or interrupted by D, wherein R$^{23}$, R$^{24}$, R$^{25}$ and R$^{26}$ are independently of each other C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—; or R$^{25}$ and R$^{26}$ together form a five or six membered ring, or ring system;

R$^{27}$ is C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—, R$^{28}$ is H; C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—, R$^{29}$ is C$_6$-C$_{18}$aryl; C$_6$-C$_{18}$aryl, which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—, R$^{30}$ and R$^{31}$ are independently of each other C$_1$-C$_{18}$alkyl, C$_6$-C$_{18}$aryl, or C$_6$-C$_{18}$aryl, which is substituted by C$_1$-C$_{18}$alkyl, and R$^{32}$ is C$_1$-C$_{18}$alkyl, C$_6$-C$_{18}$aryl, or C$_6$-C$_{18}$aryl, which is substituted by C$_1$-C$_{18}$alkyl.

L$^1$ is a single bond, —(CR$^{47}$=CR$^{48}$)$_{m2}$—, —(Ar$^3$)$_{m3}$—, —[Ar$^3$(Y$^1$)$_{m5}$]$_{m4}$—, —[(Y$^1$)$_{m5}$Ar$^3$]$_{m4}$—, or —[Ar$^3$(Y$^2$)$_{m5}$Ar$^4$]$_{m4}$—, wherein Y$^1$ is —(CR$^{47}$=CR$^{48}$)—, Y$^2$ is NR$^{49}$, O, S, C=O, C(=O)O, wherein R$^{49}$ is C$_6$-C$_{18}$aryl which can optionally be substituted by C$_1$-C$_{18}$alkyl, or C$_1$-C$_{18}$alkoxy; C$_1$-C$_{18}$alkyl; or C$_1$-C$_{18}$alkyl which is interrupted by —O—;

R$^{47}$ and R$^{48}$ are independently of each other hydrogen, C$_1$-C$_{20}$alkyl, or C$_6$-C$_{24}$aryl, which can optionally be substituted by G, m5 is an integer of 1 to 10, m2 is an integer of 1 to 10, m3 is an integer of 1 to 5, m4 is an integer of 1 to 5, Ar$^3$ and Ar$^4$ are independently of each other arylene, or heteroarylene, which can optionally be substituted, wherein G is as defined above.

Preferably, L$^1$ is a single bond, or a bridging unit BU of formula

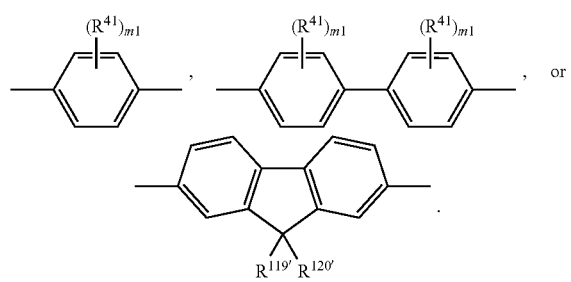

Even more preferred are compounds of the formula I, or III, wherein -L$^1$-X$^1$ is a group of formula

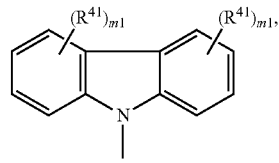

—NR$^{25'}$R$^{26'}$, or a group

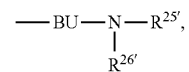

wherein R$^{25'}$ and R$^{26'}$ are independently of each other

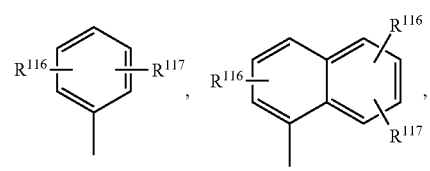

or

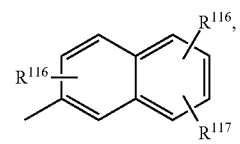

or R$^{25'}$ and R$^{26'}$ together with the nitrogen atom to which they are bonded form a group of formula

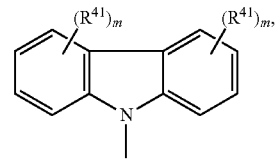

R$^{116}$ and R$^{117}$ are independently of each other C$_1$-C$_{25}$alkyl, which may optionally be interrupted by —O—, or C$_1$-C$_{25}$alkoxy;

BU is

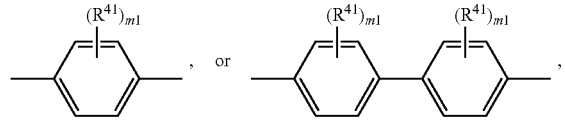

wherein R$^{41}$ can be the same or different at each occurrence and is C$_1$-C$_{25}$alkyl, which may optionally be interrupted by —O—, or C$_1$-C$_{25}$alkoxy; m1 is 0, 1, or 2.

Preferably, R$^{116}$ and R$^{117}$ are independently of each other H, C$_1$-C$_{12}$alkyl, such as methyl, ethyl, n-propyl, iso-propyl, n-butyl, isobutyl, sec-butyl, t-butyl, 2-methylbutyl, n-pentyl, isopentyl, n-hexyl, 2-ethylhexyl, or n-heptyl, C$_1$-C$_{12}$alkyl which is substituted by E and/or interrupted by D, such as —$CH_2OCH_3$, —$CH_2OCH_2CH_3$, —$CH_2OCH_2CH_2OCH_3$, or —$CH_2OCH_2CH_2OCH_2CH_3$, $C_6$-$C_{14}$aryl, such as phenyl, naphthyl, or biphenylyl, $C_5$-$C_{12}$cycloalkyl, such as cyclohexyl, $C_6$-$C_{14}$aryl which is substituted by G, such as —$C_6H_4OCH_3$, —$C_6H_4OCH_2CH_3$, —$C_6H_3(OCH_3)_2$, or —$C_6H_3(OCH_2CH_3)_2$, —$C_6H_4CH_3$, —$C_6H_3(CH_3)_2$, —$C_6H_2(CH_3)_3$, or —$C_6H_4tBu$.

Preferably, $R^{119}$ and $R^{120}$ are independently of each other $C_1$-$C_{12}$alkyl, such as methyl, ethyl, n-propyl, iso-propyl, n-butyl, sec-butyl, hexyl, octyl, or 2-ethyl-hexyl, $C_1$-$C_{12}$alkyl which is substituted by E and/or interrupted by D, such as —$CH_2(OCH_2CH_2)_wOCH_3$, w=1, 2, 3, or 4, $C_6$-$C_{14}$aryl, such as phenyl, naphthyl, or biphenylyl, $C_6$-$C_{14}$aryl which is substituted by G, such as —$C_6H_4OCH_3$, —$C_6H_4OCH_2CH_3$, —$C_6H_3(OCH_3)_2$, —$C_6H_3(OCH_2CH_3)_2$, —$C_6H_4CH_3$, —$C_6H_3(CH_3)_2$, —$C_6H_2(CH_3)_3$, or —$C_6H_4tBu$, or $R^{119}$ and $R^{120}$ together form a 4 to 8 membered ring, especially a 5 or 6 membered ring, such as cyclohexyl, or cyclopentyl, which can optionally be substituted by $C_1$-$C_8$alkyl.

D is preferably —CO—, —COO—, —S—, —SO—, —$SO_2$—, —O—, —$NR^{25}$—, wherein $R^{25}$ is $C_1$-$C_{12}$alkyl, such as methyl, ethyl, n-propyl, iso-propyl, n-butyl, isobutyl, or sec-butyl, or $C_6$-$C_{14}$aryl, such as phenyl, naphthyl, or biphenylyl.

E is preferably —$OR^{29}$; —$SR^{29}$; —$NR^{25}R^{25}$; —$COR^{28}$; —$COOR^{27}$; —$CONR^{25}R^{25}$; or —CN; wherein $R^{25}$, $R^{27}$, $R^{28}$ and $R^{29}$ are independently of each other $C_1$-$C_{12}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, naphthyl, or biphenylyl, which may optionally be substituted.

G has the same preferences as E, or is $C_1$-$C_{18}$alkyl, especially $C_1$-$C_{12}$alkyl, such as methyl, ethyl, n-propyl, iso-propyl, n-butyl, isobutyl, sec-butyl, hexyl, octyl, or 2-ethyl-hexyl.

Examples of a heteroaromatic ring, or ring system, which is formed by $R^{25'}$ and $R^{26'}$ together with the nitrogen atom to which they are bonded, are

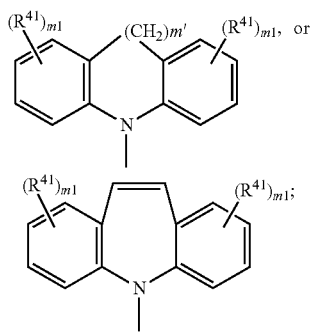

m' is 0, 1, or 2, m1 is 0, 1, or 2. Examples of

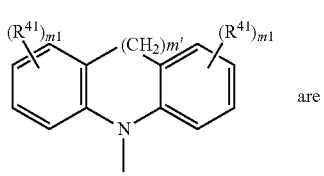

are

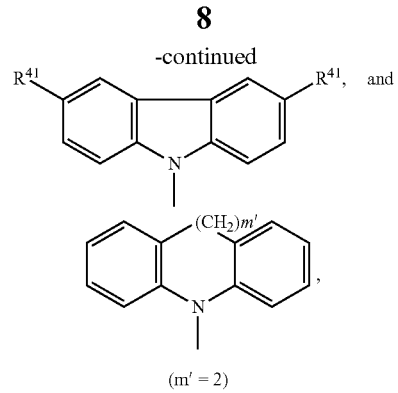

wherein $R^{41}$ is H, or $C_1$-$C_{18}$alkyl.

Examples of groups

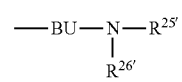

are shown below:

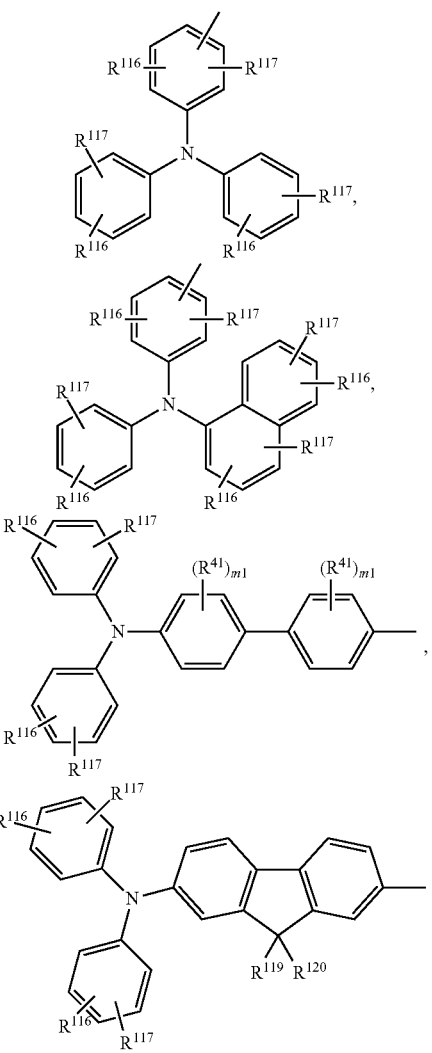

-continued

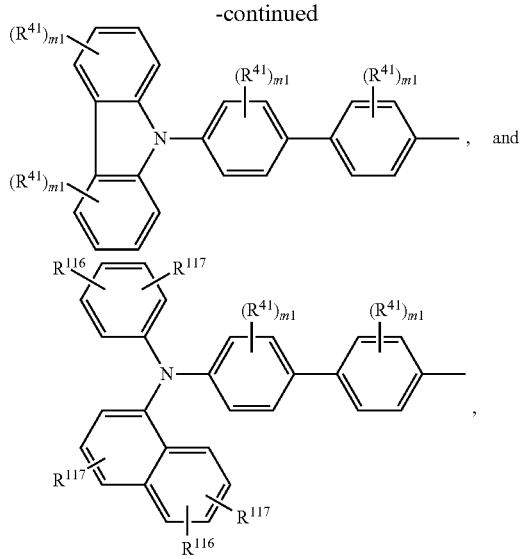

wherein $R^{41}$, $R^{116}$, $R^{117}$, $R^{119}$, $R^{120}$ and m1 are as defined above.

Even more preferred are compounds of formula

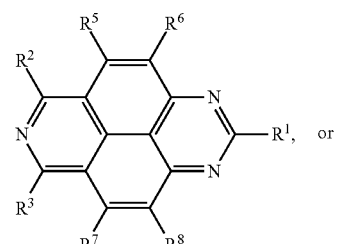
(IIa)

or

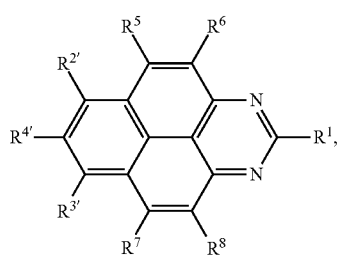
(IIb)

wherein
$R^5$, $R^6$, $R^7$ and $R^8$ are hydrogen,
$R^1$, $R^2$, $R^3$, $R^{2'}$, $R^{3'}$, and $R^{4'}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G,
$C_2$-$C_{20}$heteroaryl, $C_2$-$C_{20}$heteroaryl which is substituted by G, such as

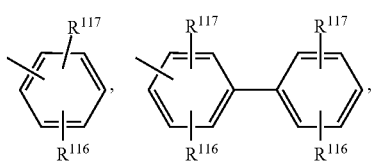

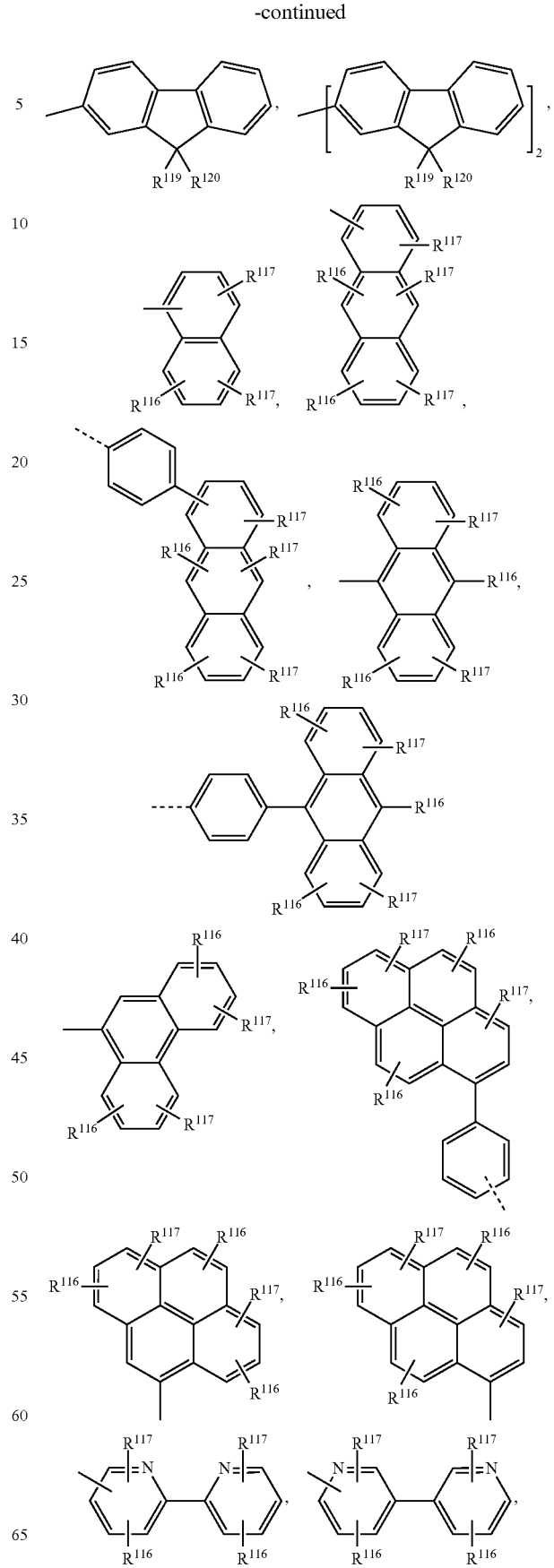

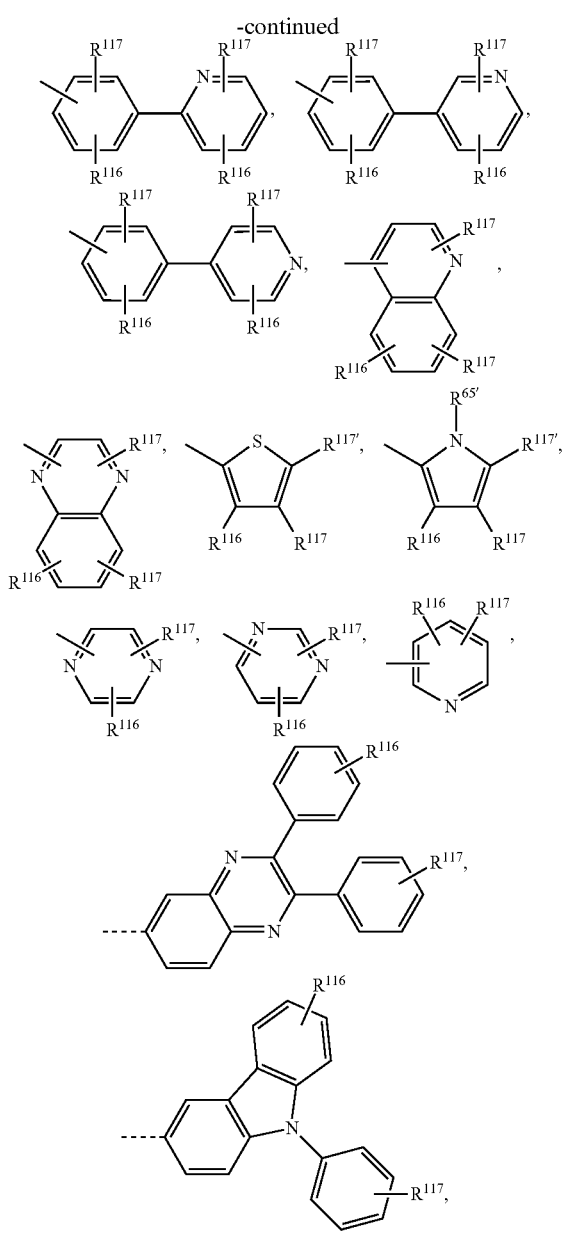

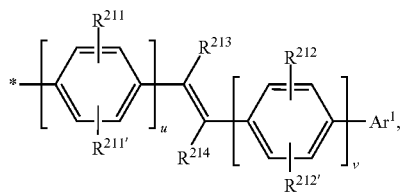

or -L$^1$-NR$^{25'}$R$^{26'}$, wherein
u is 0, or 1; v is 0, or 1;
R$^{211}$, R$^{211'}$, R$^{212}$ and R$^{212'}$ are independently of each other H, C$_1$-C$_{18}$alkyl, or C$_1$-C$_{18}$alkoxy,
R$^{213}$ and R$^{214}$ are independently of each other H, or C$_1$-C$_{18}$alkyl, Ar$^1$ is —NR$^{25'}$R$^{26'}$, C$_6$-C$_{24}$aryl, C$_6$-C$_{24}$aryl which is substituted by G, C$_2$-C$_{20}$heteroaryl, or C$_2$-C$_{20}$heteroaryl which is substituted by G;

L$^1$ is a single bond, or a bridging unit BU, such as

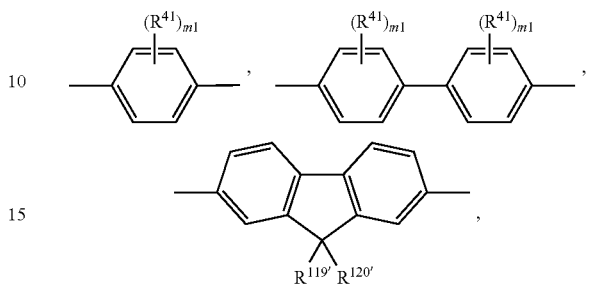

D is —O—; or —NR$^{25}$—,

E is —OR$^{29}$; —NR$^{25}$R$^{26}$; —CN; or F; R$^{29}$;R$^{25}$ and R$^{26}$ are as defined above; and G is E, C$_1$-C$_{18}$alkyl, C$_1$-C$_{18}$alkyl which is interrupted by D, C$_1$-C$_{18}$ perfluoroalkyl, C$_1$-C$_{18}$alkoxy, or C$_1$-C$_{18}$alkoxy which is substituted by E and/or interrupted by D.

R$^{25'}$ and R$^{26'}$ are independently of each other phenyl, naphthyl, anthryl, biphenylyl, 2-fluorenyl, phenanthryl, or perylenyl, which can optionally be substituted, such as

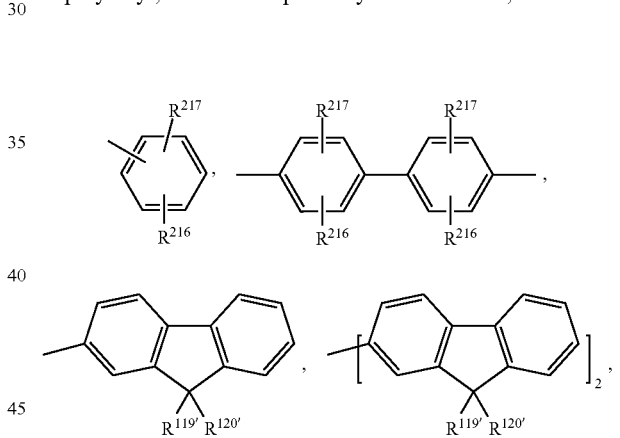

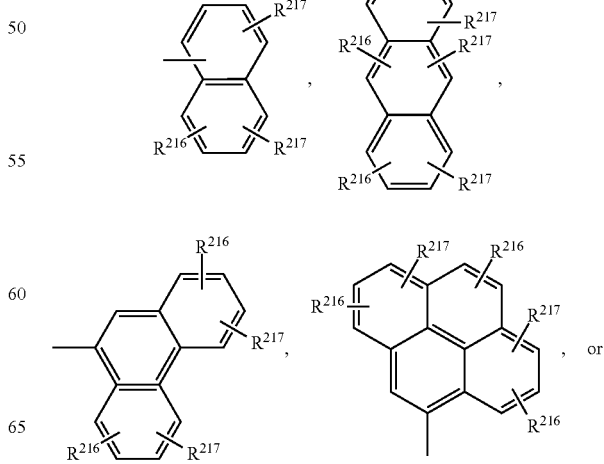

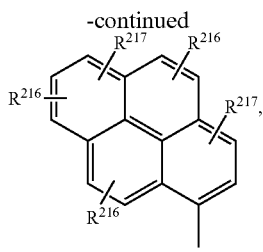

or $R^{25'}$ and $R^{26'}$ together with the nitrogen atom to which they are bonded form a heteroaromatic ring, or ring system, such as

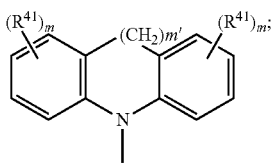

m' is 0, 1, or 2;

m can be the same or different at each occurrence and is 0, 1, 2, or 3, especially 0, 1, or 2, very especially 0 or 1;

m1 can be the same or different at each occurrence and is 0, 1, 2, 3, or 4, especially 0, 1, or 2, very especially 0 or 1, $R^{41}$ can be the same or different at each occurrence and is Cl, F, CN, $N(R^{45})_2$, a $C_1$-$C_{25}$alkyl group, a $C_4$-$C_{18}$cycloalkyl group, a $C_1$-$C_{25}$alkoxy group, in which one or more carbon atoms which are not in neighbourhood to each other could be replaced by $-NR^{45}-$, $-O-$, $-S-$, or $-C(=O)-O-$, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, or two or more groups $R^{41}$ form a ring system;

$R^{45}$ is a $C_1$-$C_{25}$alkyl group, a $C_4$-$C_{18}$cycloalkyl group, in which one or more carbon atoms which are not in neighbourhood to each other could be replaced by $-NR^{45''}-$, $-O-$, $-S-$, $-C(=O)-O-$, or, $-O-C(=O)-O-$, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, and $R^{45''}$ a $C_1$-$C_{25}$alkyl group, or a $C_4$-$C_{18}$cycloalkyl group, $R^{216}$, $R^{217}$, $R^{116}$, $R^{117}$ and $R^{117'}$ are independently of each other H, halogen, —CN, $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', $C_2$-$C_{20}$heteroaryl, $C_2$-$C_{20}$heteroaryl which is substituted by G', $C_2$-$C_{18}$alkenyl, $C_2$-$C_{18}$alkynyl, $C_1$-$C_{18}$alkoxy, $C_1$-$C_{18}$alkoxy which is substituted by E' and/or interrupted by D', $C_7$-$C_{25}$aralkyl, $-C(=O)-R^{127}$, $-C(=O)OR^{127}$, or $-C(=O)NR^{127}R^{126}$, or substituents $R^{116}$, $R^{117}$ and $R^{117'}$, which are adjacent to each other, can form a ring, $R^{119'}$ and $R^{120'}$ are independently of each other $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', $C_2$-$C_{20}$heteroaryl, $C_2$-$C_{20}$heteroaryl which is substituted by G', $C_2$-$C_{18}$alkenyl, $C_2$-$C_{18}$alkynyl, or $C_7$-$C_{25}$aralkyl, or $R^{119'}$ and $R^{120'}$ together form a group of formula $=CR^{121'}R^{122'}$, wherein $R^{121'}$ and $R^{122'}$ are independently of each other H, $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', or $C_2$-$C_{20}$heteroaryl, or $C_2$-$C_{20}$heteroaryl which is substituted by G', or $R^{119'}$ and $R^{120'}$ together form a five or six membered ring, which optionally can be substituted by $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', $C_2$-$C_{20}$heteroaryl, $C_2$-$C_{20}$heteroaryl which is substituted by G', $C_2$-$C_{18}$alkenyl, $C_2$-$C_{18}$alkynyl, $C_1$-$C_{18}$alkoxy, $C_1$-$C_{18}$alkoxy which is substituted by E' and/or interrupted by D', $C_7$-$C_{25}$aralkyl, or $-C(=O)-R^{127}$, and $R^{126}$ and $R^{127}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, D' is —CO—, —COO—, —S—, —SO—, —SO$_2$—, —O—, —NR$^{65}$—, —SiR$^{70}$R$^{71}$—, —POR$^{72}$—, —CR$^{63}$=CR$^{64}$—, or —C≡C—, and E' is —OR$^{69}$, —SR$^{69}$, —NR$^{65}$R$^{66}$, —COR$^{68}$, —COOR$^{67}$, —CONR$^{65}$R$^{66}$, —CN, or halogen, G' is E', or $C_1$-$C_{18}$alkyl, $R^{63}$ and $R^{64}$ are independently of each other H; $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by —O—;

$R^{65}$, $R^{65'}$ and $R^{66}$ are independently of each other $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by —O—; or $R^{65}$ and $R^{66}$ together form a five or six membered ring, $R^{67}$ and $R^{68}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{69}$ is $C_6$-$C_{18}$aryl; $C_6$-$C_{18}$aryl, which is substituted by $C_1$-$C_{18}$alkyl, $C_1$-$C_{18}$alkoxy; $C_1$-$C_{18}$alkyl; or $C_1$-$C_{18}$alkyl which is interrupted by —O—, $R^{79}$ and $R^{71}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{72}$ is $C_1$-$C_{18}$alkyl, $C_6$-$C_{18}$aryl, or $C_6$-$C_{18}$aryl, which is substituted by $C_1$-$C_{18}$alkyl.

D', E' and G' have the same preferences than D, E and G respectively. $R^{119'}$ and $R^{120'}$ have the same preferences than $R^{119}$ and $R^{129}$ respectively.

In compounds of formula IIa and IIb $R^1$, $R^2$, $R^3$, $R^{2'}$ and $R^{3'}$ are preferably independently of each other $C_6$-$C_{24}$aryl, $C_6$-$C_{24}$aryl which is substituted by G, $C_2$-$C_{20}$heteroaryl, $C_2$-$C_{20}$heteroaryl which is substituted by G, such as

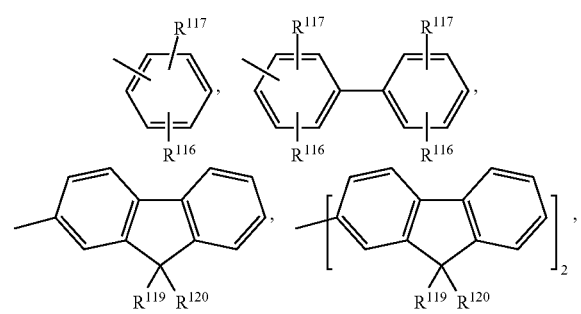

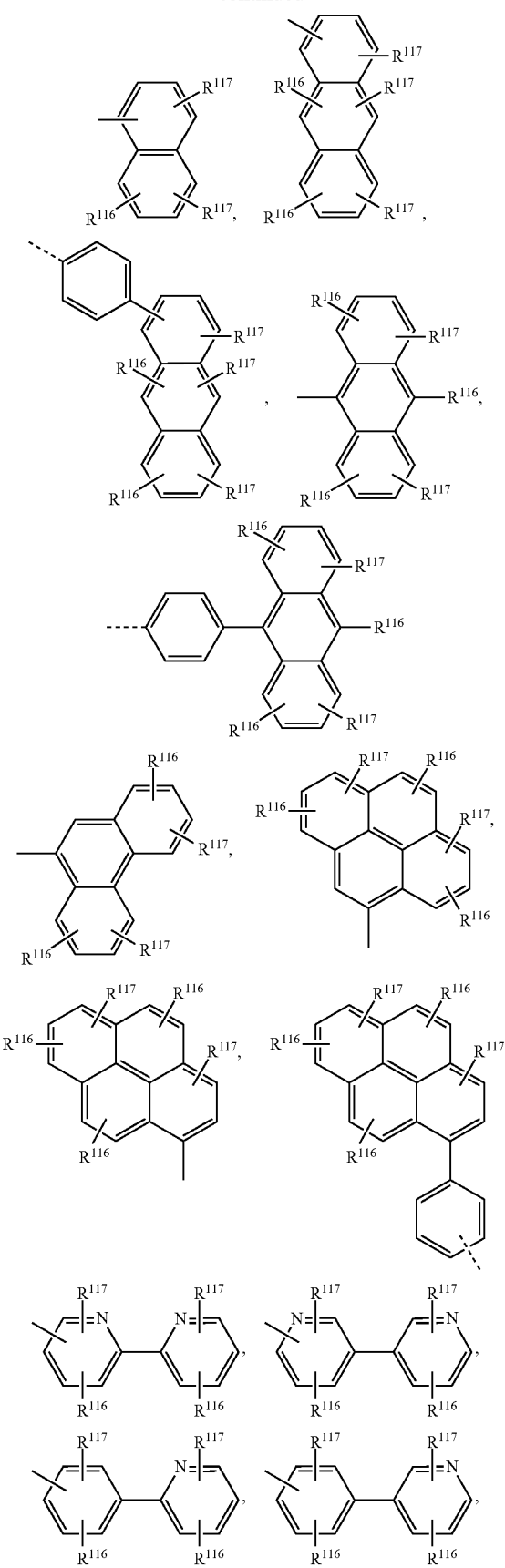
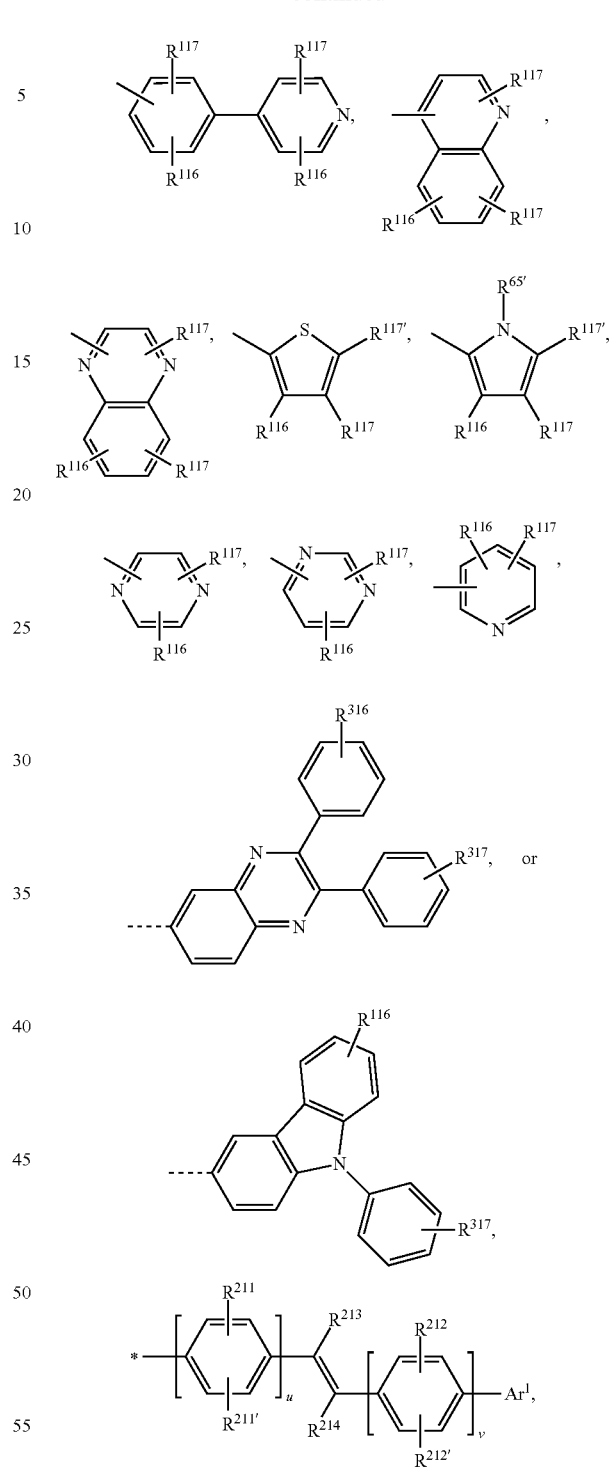

or a group -L$^1$-NR$^{25'}$R$^{26'}$, wherein R$^{316}$ and R$^{317}$ have the meaning of R$^{116}$ and are preferably C$_1$-C$_{25}$alkyl, which may optionally be interrupted by —O—, or C$_1$-C$_{25}$alkoxy.

R$^{4'}$ is hydrogen, C$_6$-C$_{24}$aryl, or C$_6$-C$_{24}$aryl which is substituted by G.

Most preferred are compounds of formula IIa, wherein R$^5$, R$^6$, R$^7$ and R$^8$ are hydrogen, R$^1$, R$^2$, and R$^3$ are independently of each other a group,

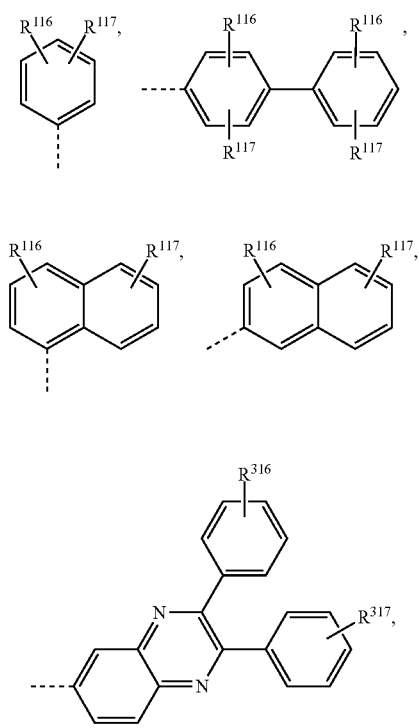
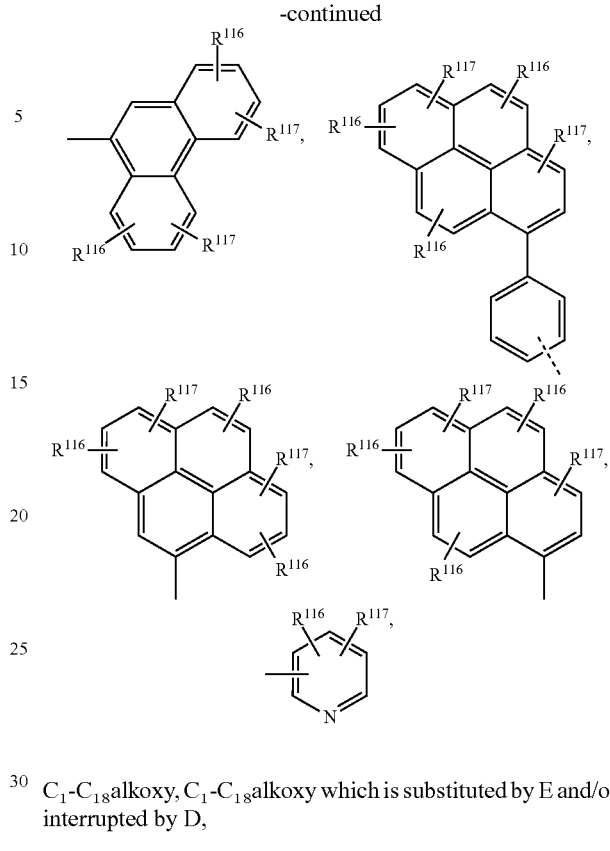
$C_1$-$C_{18}$alkoxy, $C_1$-$C_{18}$alkoxy which is substituted by E and/or interrupted by D,
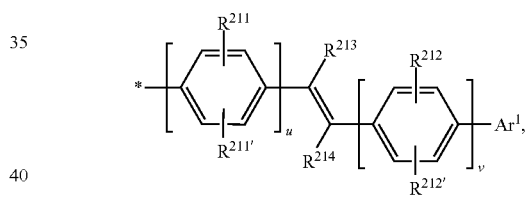
or -$L^1$-$NR^{25'}R^{26'}$,
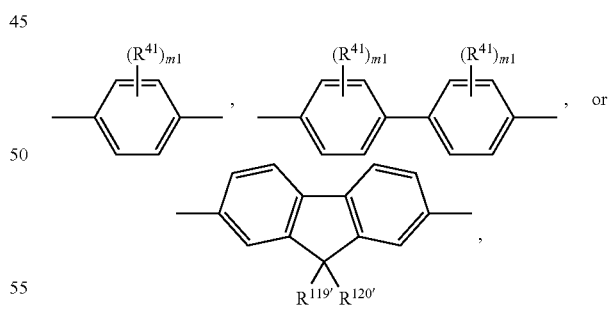
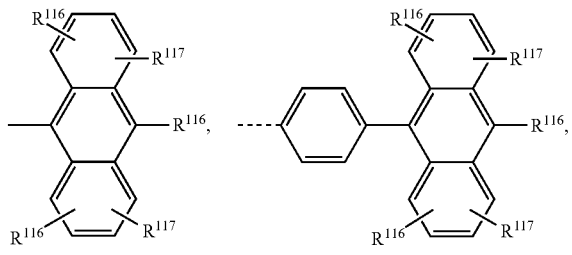
$L^1$ is a single bond,
m1 is 0, or 1;
u is 0, or 1; v is 0, or 1;
$R^{211}$, $R^{211'}$, $R^{212}$ and $R^{212'}$ are independently of each other H, or $C_1$-$C_{18}$alkyl,
$R^{213}$ and $R^{214}$ are independently of each other H, or $C_1$-$C_{18}$alkyl,
$Ar^1$ is —$NR^{25'}R^{26'}$,

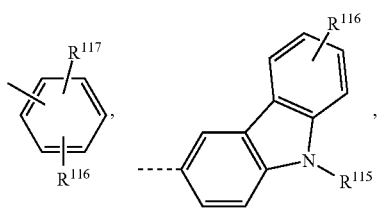

$R^{215}$ is $C_1$-$C_{25}$alkyl, or $C_6$-$C_{18}$aryl,
$R^{25'}$ and $R^{26'}$ are independently of each other

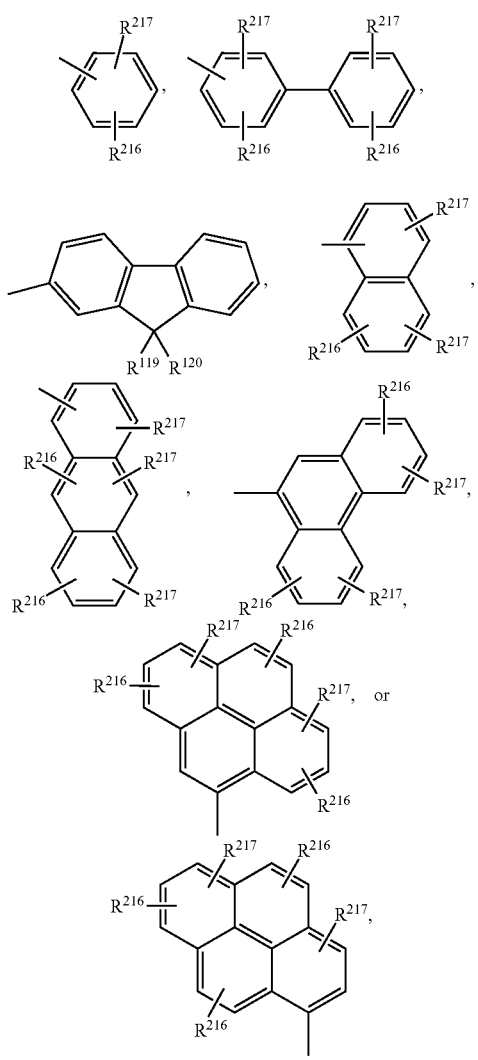

or $R^{25'}$ and $R^{26'}$ together with the nitrogen atom to which they are bonded form a group

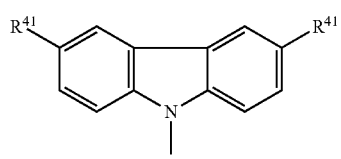

wherein $R^{41}$ is H, or $C_1$-$C_8$alkyl, and $R^{116}$ and $R^{117}$ are independently of each other $C_1$-$C_{25}$alkyl, which may optionally be interrupted by —O—, or $C_1$-$C_{25}$alkoxy, 1-naphthyl, 2-naphthyl, phenyl, or pyridine, which may optionally be substituted by $C_1$-$C_{25}$alkyl, which may optionally be interrupted by —O—, or phenyl; and $R^{316}$ and $R^{317}$ have the meaning of $R^{116}$ and are preferably $C_1$-$C_{25}$alkyl, which may optionally be interrupted by —O—, or $C_1$-$C_{25}$alkoxy, $R^{216}$ and $R^{217}$ are independently of each other $C_1$-$C_{25}$alkyl, which may optionally be interrupted by —O—, or $C_1$-$C_{25}$alkoxy; as well as compounds of formula IIb, wherein $R^5$, $R^6$, $R^7$ and $R^8$ are hydrogen, $R^1$, $R^{2'}$, and $R^{3'}$ are independently of each other a group

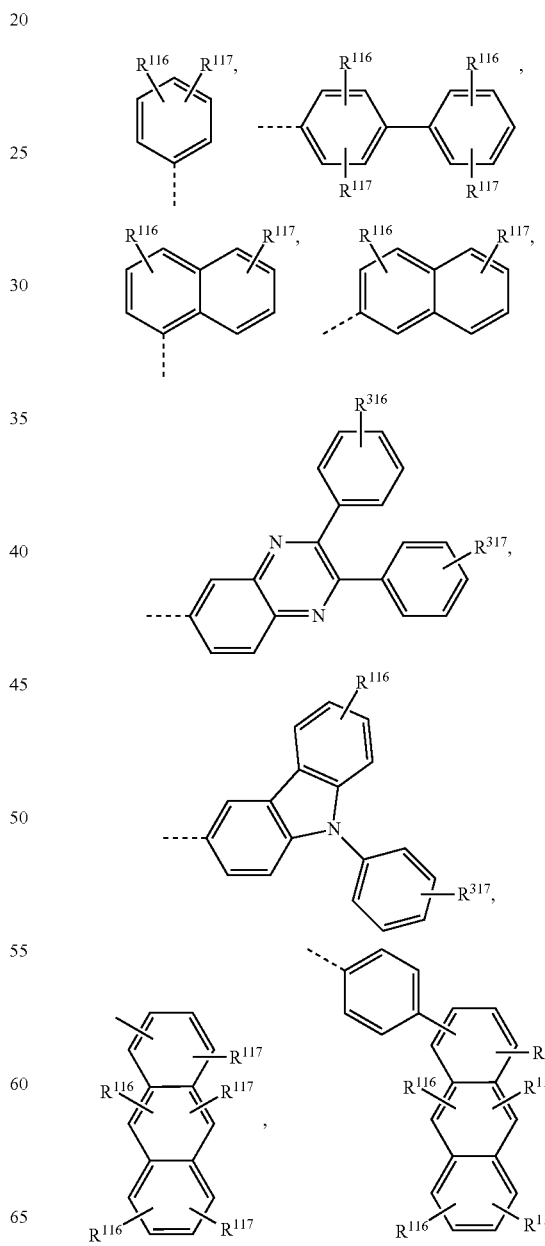

-continued

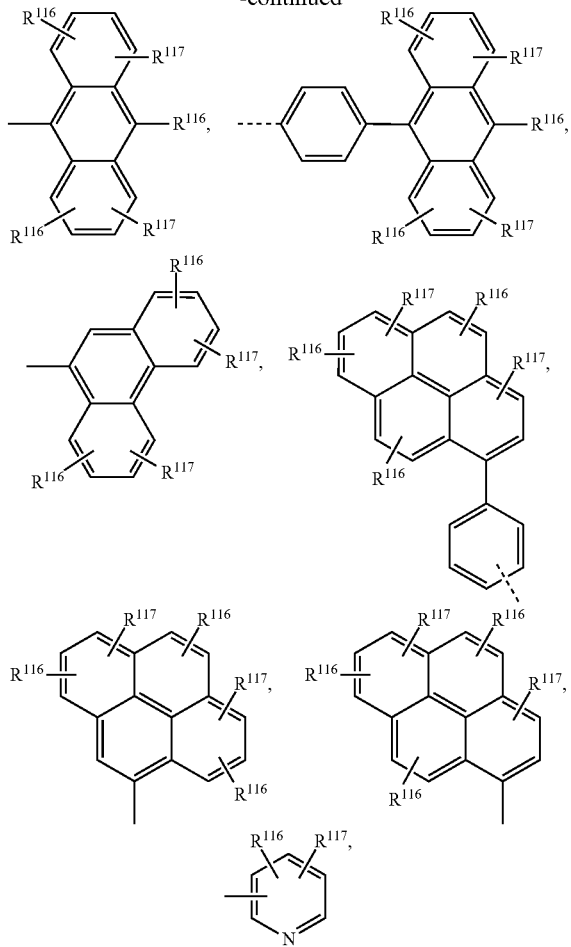

$C_1$-$C_{18}$alkoxy, $C_1$-$C_{18}$alkoxy which is substituted by E and/or interrupted by D,

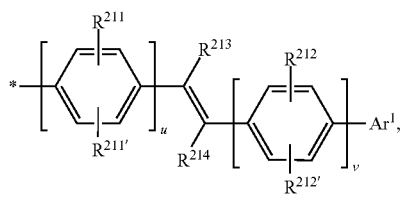

or $L^1$-$NR^{25'}R^{26'}$,
$L^1$ is a single bond,

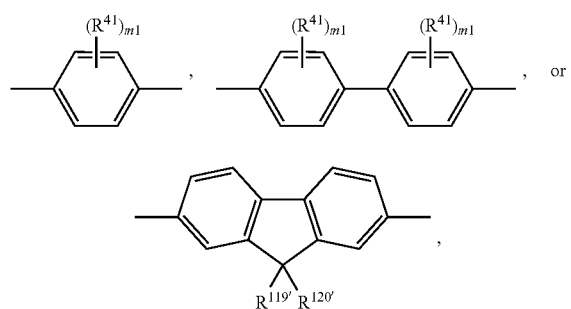

m1 is 0, or 1;

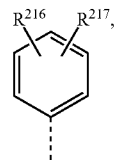

$R^{4'}$ is hydrogen, or a group
u is 0, or 1; v is 0, or 1;
$R^{211}$, $R^{211'}$, $R^{212}$ and $R^{212'}$ are independently of each other H, or $C_1$-$C_{18}$alkyl,
$R^{213}$ and $R^{214}$ are independently of each other H, or $C_1$-$C_{18}$alkyl,
$Ar^1$ is —$NR^{25'}R^{26'}$,

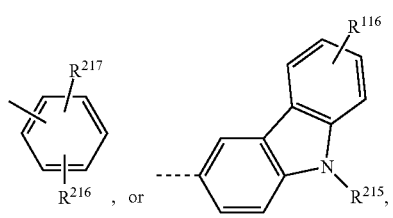

wherein $R^{215}$ is as defined above;
$R^{25'}$ and $R^{26'}$ are independently of each other

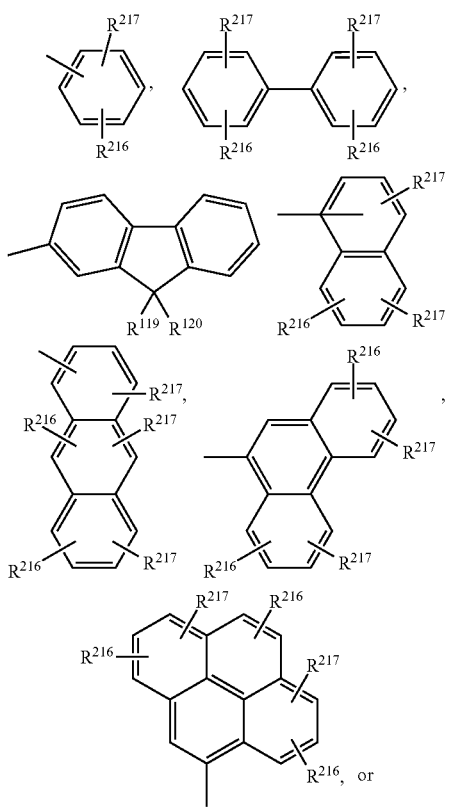

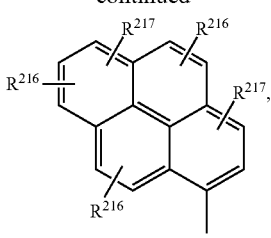

or

R$^{25'}$ and R$^{26'}$ together with the nitrogen atom to which they are bonded form a group

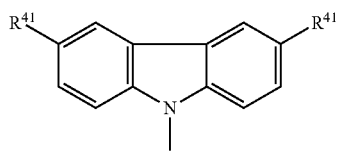

wherein R$^{41}$ is H, or C$_1$-C$_8$alkyl, and

R$^{116}$ and R$^{117}$ are independently of each other C$_1$-C$_{25}$alkyl, which may optionally be interrupted by —O—, or C$_1$-C$_{25}$alkoxy, 1-naphthyl, 2-naphthyl, phenyl, or pyridine, which may optionally be substituted by C$_1$-C$_{25}$alkyl, which may optionally be interrupted by —O—, or phenyl;

R$^{316}$ and R$^{317}$ have the meaning of R$^{116}$ and are preferably C$_1$-C$_{25}$alkyl, which may optionally be interrupted by —O—, or C$_1$-C$_{25}$alkoxy;

R$^{119'}$ and R$^{120'}$ are independently of each other C$_1$-C$_{25}$alkyl, or C$_1$-C$_{25}$alkyl, which is substituted by E and/or interrupted by D, R$^{216}$ and R$^{217}$ are independently of each other C$_1$-C$_{25}$alkyl, which may optionally be interrupted by —O—, or C$_1$-C$_{25}$alkoxy, D is —O—; or —NR$^{25}$—, and E is —OR$^{29}$; —NR$^{25}$R$^{26}$; —CN, or F; R$^{29}$; R$^{25}$, and R$^{26}$ are as defined above.

Examples of particularly preferred compounds of formula IIa are compounds A-1-A-19, which are shown in claim 6.

Examples of particularly preferred compounds of formula IIb are compounds B-1-B-42, which are shown in claim 6.

In another preferred embodiment the present invention relates to an electronic device, comprising a compound of formula III, especially a compound of formula

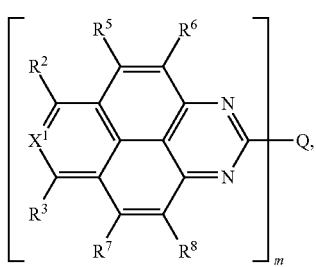
(IIIa)

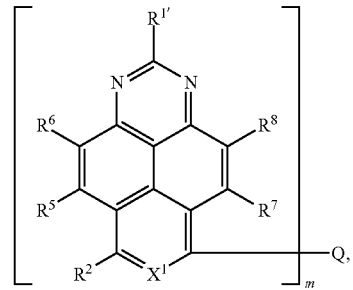
(IIIb)

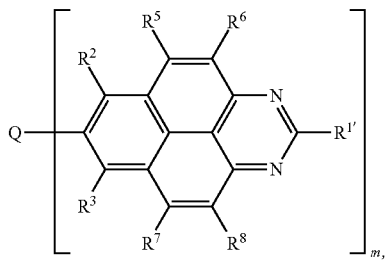
(IIIc)

wherein m, R$^1$, R$^2$, R$^3$, X$^1$, R$^5$, R$^6$, R$^7$ and R$^8$ are as defined above, and Q is a group of formula

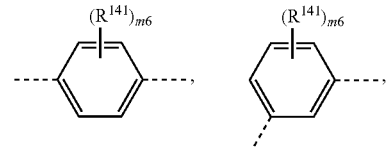

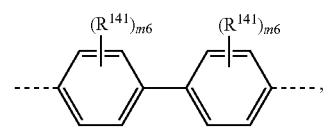

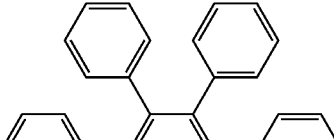

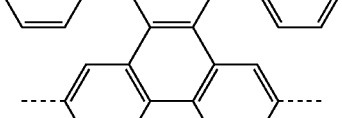

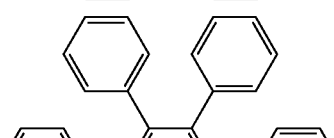

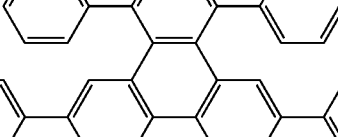

-continued

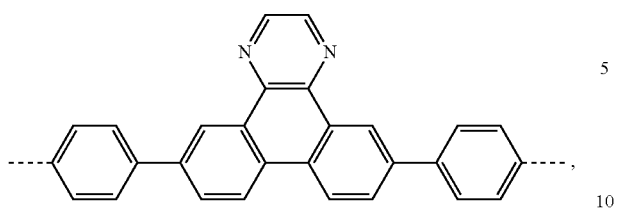

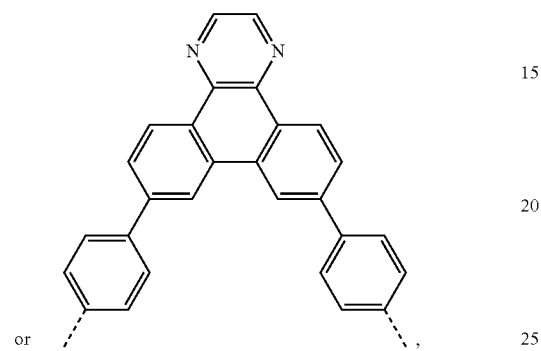
or wherein $R^{141}$ can be the same or different at each occurrence and is $C_1$-$C_{25}$alkyl, which may optionally be interrupted by —O—, or $C_1$-$C_{25}$alkoxy; m6 is 0, 1, or 2.

Even more preferred are compounds of formula IIIa, IIIb, or IIIc, wherein $X^1$ is CH, or N, $R^5$, $R^6$, $R^7$ and $R^8$ are hydrogen, $R^1$, $R^2$, $R^3$ are independently of each other

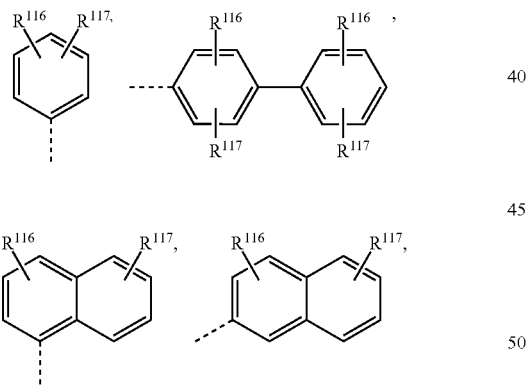

$R^{116}$ and $R^{117}$ are independently of each other $C_1$-$C_{25}$alkyl, which may optionally be interrupted by —O—, or $C_1$-$C_{25}$alkoxy, and Q and m are as defined above.

Examples of particularly preferred compounds of formula IIIa are compounds $C_1$-$C_7$, which are shown in claim 9.

Examples of particularly preferred compounds of formula IIIb are compounds D1-D6, which are shown in claim 9.

In another preferred embodiment the present invention relates to an electronic device, comprising a compound of formula

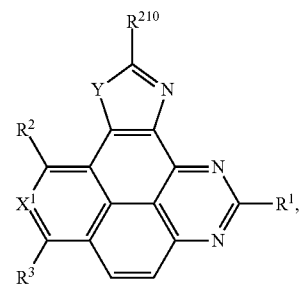
(Iva)

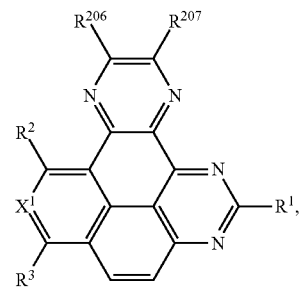
(Ivb)

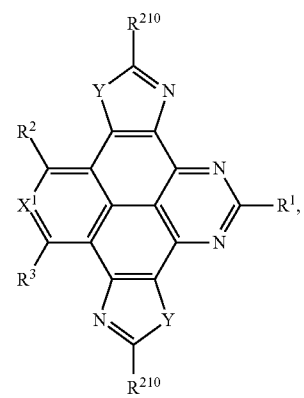
(Va)

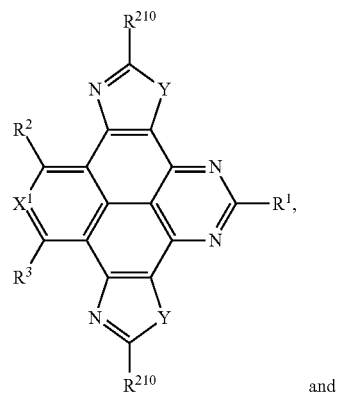
and
(Vb)

-continued (Vc)

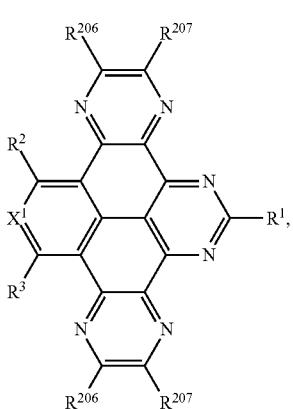

wherein
$X^1$ is N, or CH,
Y is O, or $NR^{25}$,
$R^{25}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl;
or $C_1$-$C_{18}$alkyl which is interrupted by —O—; and
$R^1$, $R^2$, $R^3$, $R^{206}$, $R^{207}$, $R^{210}$ are as defined above.

Compounds of formula Iva, Ivb, Va, Vb and Vc are even more preferred, wherein
$R^1$ is $C_6$-$C_{24}$aryl, $C_6$-$C_{24}$aryl which is substituted by G, or a group of formula

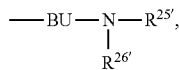

$R^2$ and $R^3$ are independently of each other $C_6$-$C_{24}$aryl, $C_6$-$C_{24}$aryl which is substituted by G,
$R^{25}$ is $C_6$-$C_{24}$aryl, $C_6$-$C_{24}$aryl which is substituted by G,
$R^{206}$ and $R^{207}$ are independently of each other H, $C_1$-$C_{18}$alkyl, $C_1$-$C_{18}$alkyl which is substituted by E and/or interrupted by D, $C_1$-$C_{18}$ perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, or
$R^{206}$ and $R^{207}$ form together a group of formula

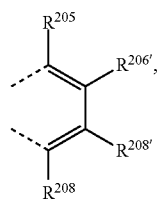

wherein
$R^{205}$ and $R^{208}$ are H,
$R^{206'}$ and $R^{208'}$ are independently of each other H, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, or CN,
$R^{210}$ is $C_6$-$C_{24}$aryl, $C_6$-$C_{24}$aryl which is substituted by G, or a group of formula

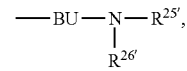

$X^1$ is N, or CH,
Y is O, or $NR^{25}$, wherein
D is —O—; or —$NR^{25}$—,
E is —$OR^{29}$; —$NR^{25}R^{26}$; —CN; or F; and
G is E, $C_1$-$C_{18}$alkyl, $C_1$-$C_{18}$alkyl which is interrupted by D, $C_1$-$C_{18}$ perfluoroalkyl, $C_1$-$C_{18}$alkoxy,
or $C_1$-$C_{18}$alkoxy which is substituted by E and/or interrupted by D,
$R^{25}$ and $R^{26}$ are $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;
$R^{29}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;
$R^{25'}$ and $R^{26'}$ are independently of each other

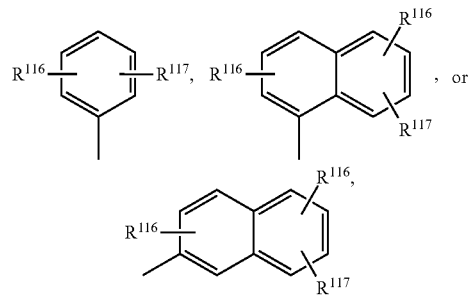

or $R^{25'}$ and $R^{26'}$ together with the nitrogen atom to which they are bonded
form a group of formula

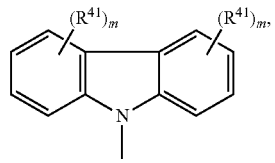

$R^{116}$ and $R^{117}$ are independently of each other $C_1$-$C_{25}$alkyl, which may optionally be interrupted by —O—, or $C_1$-$C_{25}$alkoxy;
BU is

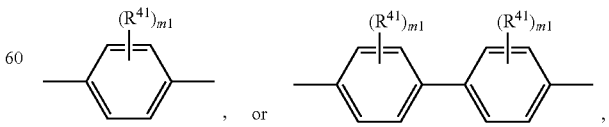

wherein $R^{41}$ can be the same or different at each occurrence and is $C_1$-$C_{25}$alkyl, which may optionally be interrupted by —O—, or $C_1$-$C_{25}$alkoxy; m1 is 0, 1, or 2.

$R^1$ is preferably a group

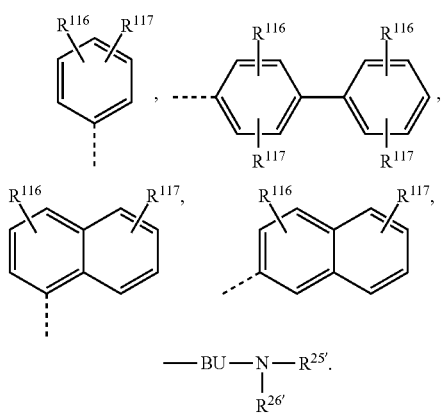

—BU—N(R^{25'})—R^{26'}.

$R^2$, $R^3$ and $R^{25}$ are preferably a group

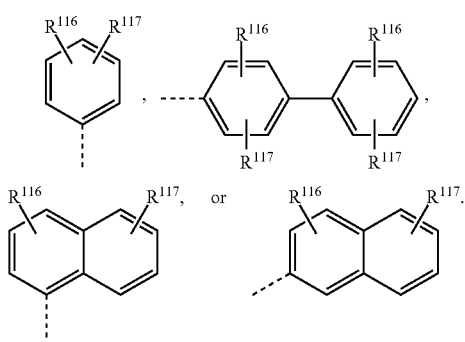

$R^{25'}$ and $R^{26'}$ are independently of each other

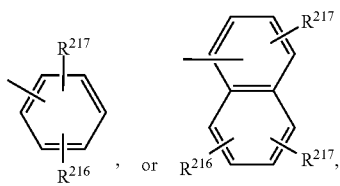

or $R^{25'}$ and $R^{26'}$ together with the nitrogen atom to which they are bonded form a group

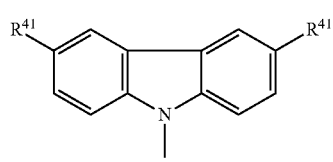

wherein $R^{41}$ is H, or $C_1$-$C_8$alkyl.

$R^{206}$ and $R^{207}$ are independently of each other H, CN, or $C_1$-$C_{18}$alkyl which is interrupted by O, or $R^{206}$ and $R^{207}$ form together a group of formula

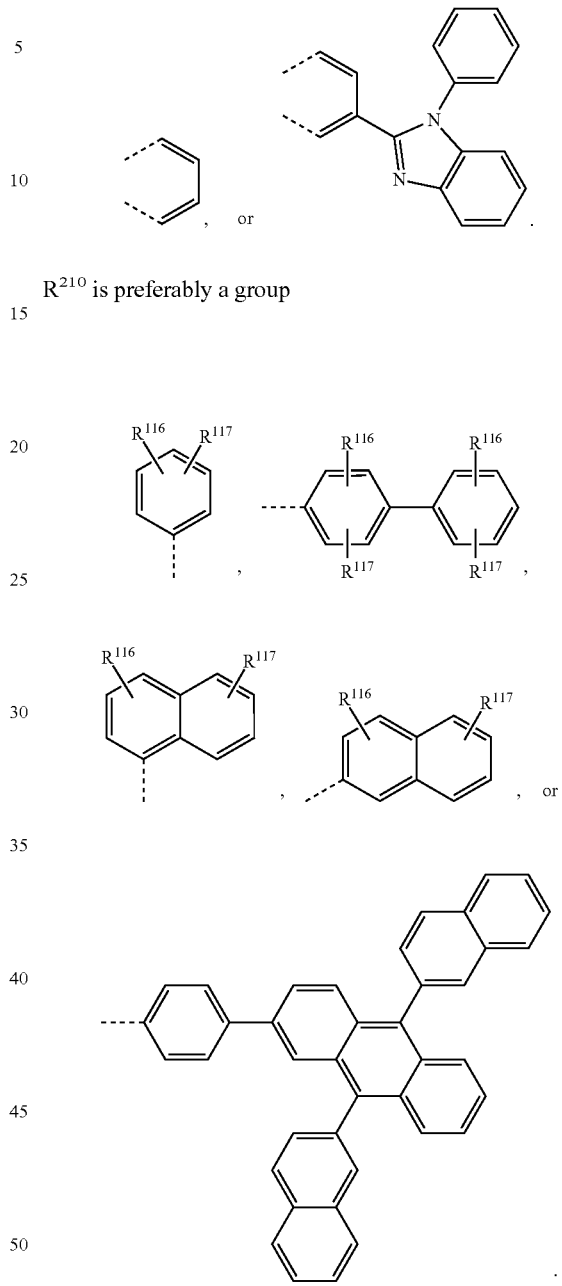

$R^{210}$ is preferably a group $R^{116}$ and $R^{117}$ are $C_1$-$C_{25}$alkyl, which may optionally be interrupted by —O—, CN, or $C_1$-$C_{25}$alkoxy.
$R^{216}$ and $R^{217}$ are $C_1$-$C_{25}$alkyl, which may optionally be interrupted by —O—, or $C_1$-$C_{25}$alkoxy.

Preferred compounds of formula Iva are compounds E-1 to E-8, F-1 and F-2 as shown in claim 6.

Preferred compounds of formula Ivb are compounds G-1 to G-5, H-1 and H-2 as shown in claim 6.

Preferred compounds of formula Vb are compounds I-1 to I-5 and J-1 to J-4 as shown in claim 6.

Preferred compounds of formula Vc are compounds K-1 to K-8, L-1 and L-2 as shown in claim 6.

Compounds of formula Iva, Ivb, Va, Vb and Vc can be prepared by using the compounds of formula

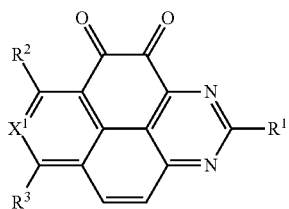

(VIa)

and

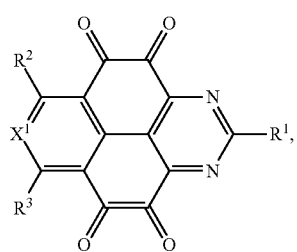

(VIb)

respectively as starting materials, wherein $X^1$, $R^1$, $R^2$ and $R^3$ are as defined above. A compound of an imidazole system can be prepared by stirring a compound of formula VIa, or VIb under reflux with an aldehyde, ammonium acetate (optionally an aromatic amine can be added, which lead to substituted products) an appropriate solvent. Further, diamine can be added to a compound of formula VIa, or VIb and then stirred under reflux under acid conditions to prepare a compound of a pyrazine system. Furthermore, the compound of an oxazole system can be obtained by reacting a compound of formula VIa, or VIb with the appropriate aldehyde in the presence of ammonium acetate and an aliphatic amine. Synthetic procedures are described in WO2006/097419.

Compounds of the formula VIa and VIb are new and form a further subject of the present invention.

Compounds of formula VIa and VIb can be produced by oxidizing azapyrenes of formula II, wherein $R^5$, $R^6$, $R^7$ and $R^8$ are H, with sodium perchlorate or sodium periodate in the presence of ruthenium trichlorate in methylenechlorid according to the procedure described in J. Org. Chem. 2005, 70, 707-708.

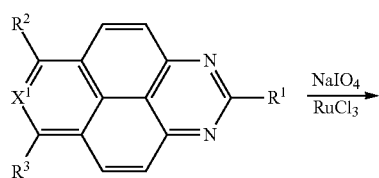

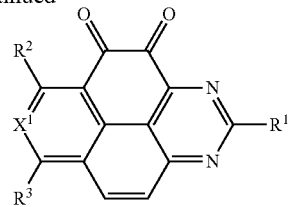

VIa or

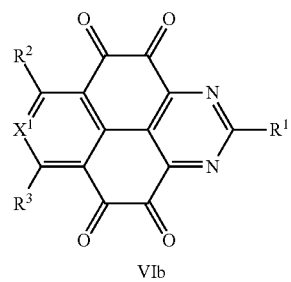

VIb

Dependent on the amount of oxidation agent and the reaction time compounds of formula VIa and/or VIb are obtained.

The compounds of formula Iva, Ivb, Va, Vb and Vc has a basic structure in which the derivative can perform functions of not only electron or hole injection and/or transportation, but also that of light emission, for example, that of a single light-emitting material, a light-emitting dopant together with a suitable host or a blue light-emitting host together with a suitable dopant in an organic electronic device. As host a fluorescent or phosphorescent emitter material can be used. By applying the compounds of formula Iva, Ivb, Va, Vb and Vc in the organic electronic device, it is possible to achieve excellent effects in terms of an efficiency of a device, drive voltage and stability.

The compounds of the present the invention can function in an organic electronic device including an organic solar cell, an organic photoconductor and an organic transistor, according to a principle similar to that applied to the organic light-emitting device.

Halogen is fluorine, chlorine, bromine and iodine.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_1$-$C_{25}$alkoxy ($C_1$-$C_{18}$alkoxy) groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulphur atom.

$C_2$-$C_{25}$alkenyl ($C_2$-$C_{18}$alkenyl) groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-24}$alkynyl ($C_{2-18}$alkynyl) is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

$C_1$-$C_{18}$perfluoroalkyl, especially $C_1$-$C_4$perfluoroalkyl, is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

The terms "haloalkyl, haloalkenyl and haloalkynyl" mean groups given by partially or wholly substituting the abovementioned alkyl group, alkenyl group and alkynyl group with halogen, such as trifluoromethyl etc. The "aldehyde group, ketone group, ester group, carbamoyl group and amino group" include those substituted by an alkyl group, a cycloalkyl group, an aryl group, an aralkyl group or a heterocyclic group, wherein the alkyl group, the cycloalkyl group, the aryl group, the aralkyl group and the heterocyclic group may be unsubstituted or substituted. The term "silyl group" means a group of formula —$SiR^{262}R^{263}R^{264}$, wherein $R^{262}$, $R^{263}$ and $R^{264}$ are independently of each other a $C_1$-$C_8$alkyl group, in particular a $C_1$-$C_4$ alkyl group, a $C_6$-$C_{24}$aryl group or a $C_7$-$C_{12}$aralkyl group, such as a trimethylsilyl group. The term "siloxanyl group" means a group of formula —O—$SiR^{262}R^{263}R^{264}$, wherein $R^{262}$, $R^{263}$ and $R^{264}$ are as defined above, such as a trimethylsiloxanyl group.

The term "cycloalkyl group" is typically $C_5$-$C_{18}$cycloalkyl, especially $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The term "cycloalkenyl group" means an unsaturated alicyclic hydrocarbon group containing one or more double bonds, such as cyclopentenyl, cyclopentadienyl, cyclohexenyl and the like, which may be unsubstituted or substituted. The cycloalkyl group, in particular a cyclohexyl group, can be condensed one or two times by phenyl which can be substituted one to three times with $C_1$-$C_4$-alkyl, halogen and cyano.

Examples of such condensed cyclohexyl groups are:

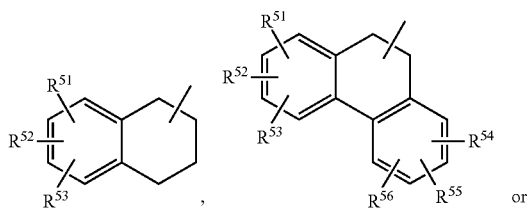

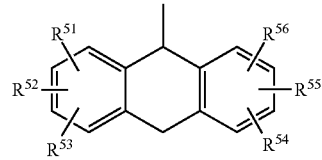

in particular

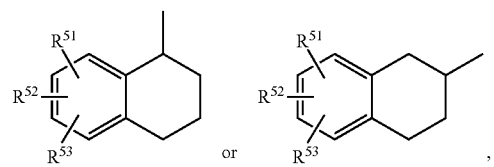

wherein $R^{51}$, $R^{52}$, $R^{53}$, $R^{54}$, $R^{55}$ and $R^{56}$ are independently of each other $C_1$-$C_8$-alkyl, $C_1$-$C_8$-alkoxy, halogen and cyano, in particular hydrogen.

Aryl is usually $C_6$-$C_{30}$aryl, preferably $C_6$-$C_{24}$aryl, which optionally can be substituted, such as, for example, phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, anthryl, tetracyl, pentacyl, hexacyl, or quaderphenylyl, which may be unsubstituted or substituted.

The term "aralkyl group" is typically $C_7$-$C_{25}$aralkyl, such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted.

The term "aryl ether group" is typically a $C_{8-24}$aryloxy group, that is to say O—$C_{6-24}$aryl, such as, for example, phenoxy or 4-methoxyphenyl. The term "aryl thioether group" is typically a $C_{6-24}$arylthio group, that is to say S—$C_{6-24}$aryl, such as, for example, phenylthio or 4-methoxyphenylthio. The term "carbamoyl group" is typically a $C_{1-18}$-carbamoyl radical, preferably $C_{18}$carbamoyl radical, which may be unsubstituted or substituted, such as, for example, carbamoyl, methylcarbamoyl, ethylcarbamoyl, n-butylcarbamoyl, tert-butylcarbamoyl, dimethylcarbamoyloxy, morpholinocarbamoyl or pyrrolidinocarbamoyl.

The terms "aryl" and "alkyl" in alkylamino groups, dialkylamino groups, alkylarylamino groups, arylamino groups and diaryl groups are typically $C_1$-$C_{25}$alkyl and $C_6$-$C_{24}$aryl, respectively.

Alkylaryl refers to alkyl-substituted aryl radicals, especially $C_7$-$C_{12}$alkylaryl. Examples are tolyl, such as 3-methyl-, or 4-methylphenyl, or xylyl, such as 3,4-dimethylphenyl, or 3,5-dimethylphenyl.

Heteroaryl is typically $C_2$-$C_{26}$heteroaryl ($C_2$-$C_{20}$heteroaryl), i.e. a ring with five to seven ring atoms or a condensed ring system, wherein nitrogen, oxygen or sulphur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted.

Examples of a five or six membered ring formed by, for example, $R^{25'}$ and $R^{26'}$, respectively are heterocycloalkanes or heterocycloalkenes having from 3 to 5 carbon atoms which can have one additional hetero atom selected from nitrogen, oxygen and sulphur, for example

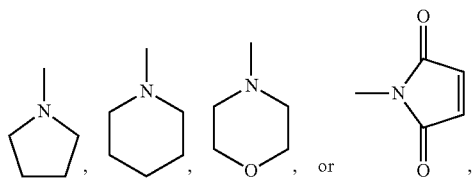

which can be part of a bicyclic system, for example

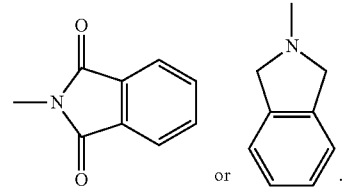

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group or a silyl group, wherein $C_1$-$C_8$alkyl, $C_1$-$C_8$alkoxy, a cyano group, or a silyl group are preferred.

If a substituent, such as, for example $R^{41}$ occurs more than one time in a group, it can be different in each occurrence.

The wording "substituted by G" means that one, or more, especially one to three groups G might be present.

As described above, the aforementioned groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl or alkylaryl contains the unit D in the alkyl moiety. $C_1$-$C_{18}$alkyl substituted by one or more E and/or interrupted by one or more units D is, for example, $(CH_2CH_2O)_{1-9}$—$R^x$, where $R^x$ is H or $C_1$-$C_{18}$alkyl or $C_2$-$C_{10}$alkanoyl (e.g. CO—CH($C_2H_5$)$C_4H_9$), $CH_2$—CH(OR$^{y''}$)—$CH_2$—O—$R^y$, where $R^y$ is $C_1$-$C_{18}$alkyl, $C_5$-$C_{12}$cycloalkyl, phenyl, $C_7$-$C_{15}$-phenylalkyl, and $R^{y''}$ embraces the same definitions as $R^y$ or is H;
$C_1$-$C_8$alkylene-COO—$R^z$, e.g. $CH_2COOR_z$, $CH(CH_3)CO$-$OR^z$, $C(CH_3)_2COOR^z$, where $R^z$ is H, $C_1$-$C_{18}$alkyl, $(CH_2CH_2O)_{1-9}$—$R^x$, and $R^x$ embraces the definitions indicated above;
$CH_2CH_2$—O—CO—CH=$CH_2$; $CH_2CH(OH)CH_2$—O—CO—C(CH$_3$)=$CH_2$.

Preferred arylene radicals are 1,4-phenylene, 2,5-tolylene, 1,4-naphthylene, 1,9 antracylene, 2,7-phenantrylene and 2,7-dihydrophenantrylene.

Preferred heteroarylene radicals are 2,5-pyrazinylene, 3,6-pyridazinylene, 2,5-pyridinylene, 2,5-pyrimidinylene, 1,3,4-thiadiazol-2,5-ylene, 1,3-thiazol-2,4-ylene, 1,3-thiazol-2,5-ylene, 2,4-thiophenylene, 2,5-thiophenylene, 1,3-oxazol-2,4-ylene, 1,3-oxazol-2,5-ylene and 1,3,4-oxadiazol-2,5-ylene, 2,5-indenylene and 2,6-indenylene.

Specific compounds of formula I and III are new and form a further subject of the present invention. Hence, the present invention is also directed to compounds of formula

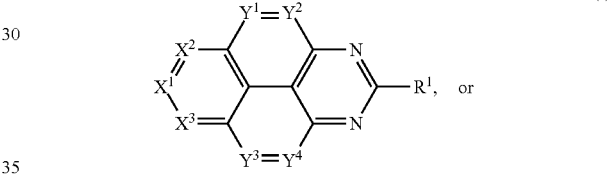

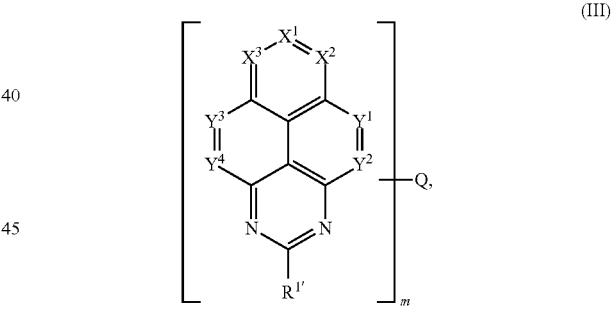

wherein
$Y^1, Y^2, Y^3, Y^4, X^1, X^2$ and $X^3$ are independently each other N, or $CR^4$,
with the proviso that at least one of the groups $X^1, X^2$ and $X^3$ is a group $CR^4$,
$R^1$ is F, —SiR$^{100}$R$^{101}$R$^{102}$, or an organic substituent,
$R^{1'}$ and $R^4$ are independently of each other hydrogen, F, —SiR$^{100}$R$^{101}$R$^{102}$ or an organic substituent, or
any of the substituents $R^1$, $R^{1'}$ and $R^4$, which are adjacent to each other, together form an aromatic, or heteroaromatic ring, or ring system, which can optionally be substituted,
m is an integer of 1 to 6, and
$R^{100}$, $R^{101}$ and $R^{102}$ are independently of each other a $C_1$-$C_8$alkyl group, a $C_6$-$C_{24}$aryl group, or a $C_7$-$C_{12}$aralkyl group, which may optionally be substituted, and Q is a linking group; with the proviso that in the compound of formula III at least one of the substituents $R^1$, or $R^4$ is a group Q and with the further proviso that the following compounds 1 to 12 are excluded:
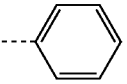
| Cpd. | R¹ | R² | R³ |
|---|---|---|---|
| 1 | phenyl | phenyl | phenyl |
| 2 | 4-Br-phenyl | 4-Br-phenyl | 4-Br-phenyl |
| 3 | 4-NO₂-phenyl | 4-NO₂-phenyl | 4-NO₂-phenyl |
| 4 | —CH₃ | H | H |
| 5 | phenyl | H | H |
| 6 | —CH₃ | —CH₃ | —CH₃ |
| Cpd. | R¹ | R² | R³ | R⁴ |
|---|---|---|---|---|
| 7 | —CH₃ | phenyl | phenyl | H |
| 8 | phenyl | phenyl | phenyl | H |
| 9 | —CH₃ | H | —CH₃ | —CO₂C₂H₅ |
| 10 | phenyl | phenyl | phenyl | H |
| 11 | —CH₃ | —CH₃ | phenyl | H |
| 12 | phenyl | —CH₃ | phenyl | H |

$R^1$ is preferably $C_6$-$C_{24}$aryl, $C_6$-$C_{24}$aryl which is substituted by G, $C_2$-$C_{20}$heteroaryl, $C_2$-$C_{20}$heteroaryl which is substituted by G, such as

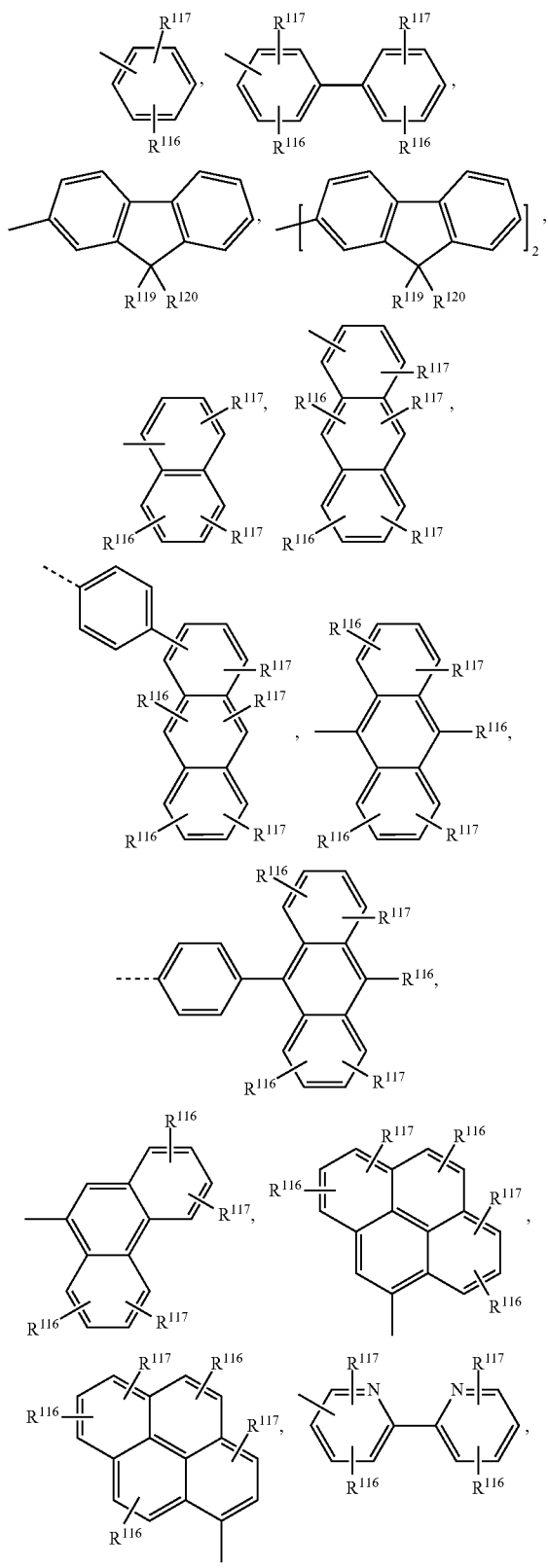

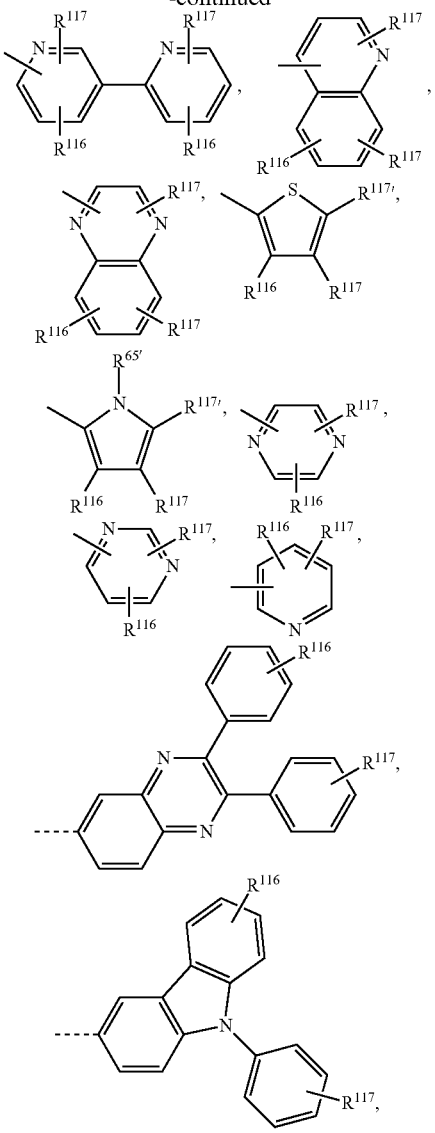

or a group -$L^1$-$NR^{25'}R^{26'}$.

The synthesis of the compounds of formula I can be done in accordance, or in analogy to known procedures. Reference is made, for example, to A. V. Aksenov et. al., Chemistry of Heterocyclic Compounds (2003) 1417.

Compounds of formula IIa can be obtained by reacting compounds of formula X with compounds of formula XI in the presence of polyphosphoric acid (PPA) (A. V. Aksenov et. al., Tetrahedron Letters (2008) 707 and ibid. (2008) 1808).

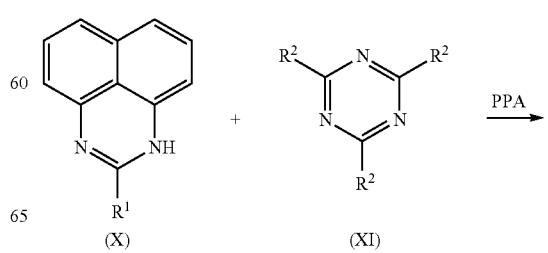

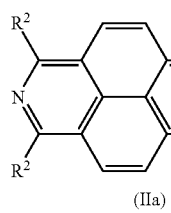

(IIa)

Alternatively, compounds of formula IIa, wherein R¹=R²=R³, can be obtained by reacting compounds of formula XIII with compounds of formula XIV in the presence of polyphosphoric acid (PPA) (A. V. Aksenov et. al., Chemistry of Heterocyclic Compounds (2002) 665).

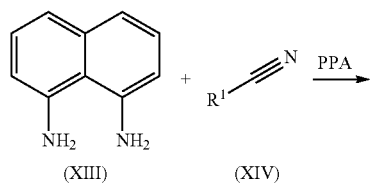

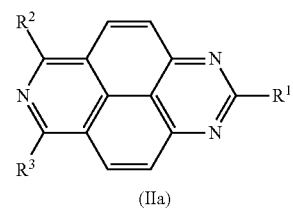

(IIa)

Compounds of formula IIb can be obtained by reacting compounds of formula X with compounds of formula XII in the presence of polyphosphoric acid (PPA) (A. V. Aksenov et. al., Chemistry of Heterocyclic Compounds (1997) 1367 and ibid. (2007) 257).

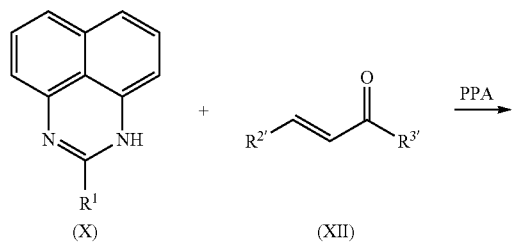

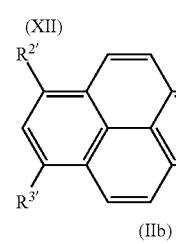

(IIb)

The synthesis of the compounds of formula X can be done in accordance, or in analogy to the procedure described in A. L. Llamas-Saiz, J. Chem. Soc. Perkin. Trans. (1995) 1389.

Compounds of formula III, wherein Q is an arylene, or heteroarylene radical, can be prepared, for example, by reaction of a compound of formula Xa with XII in PPA.

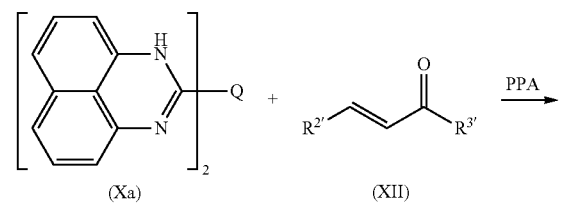

The compounds of formula Xa can be prepared as described in Khimiya Geterotsiklicheskikh Soedinenii (1980) 96-100.

Compounds of formula III, wherein Q is an arylene, or heteroarylene radical, can also be prepared starting from X and XIIa:

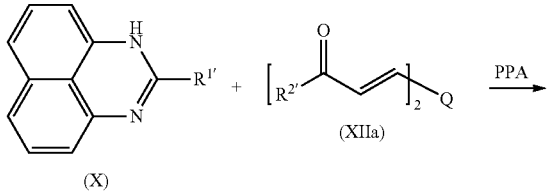

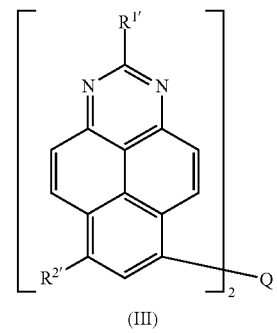

(III)

The compounds of formula XIIa can be prepared as described, for example, in Synthetic Communications 32 (2002) 3389:

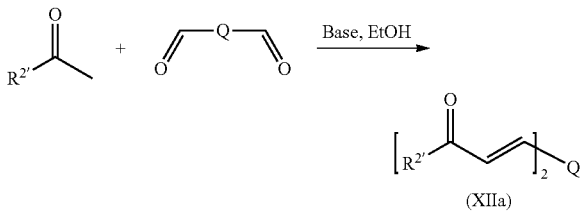

Alternatively, compounds of formula III can also be prepared by Suzuki coupling of an azapyrene carrying a boronic ester function and bromoaryl azapyrene.

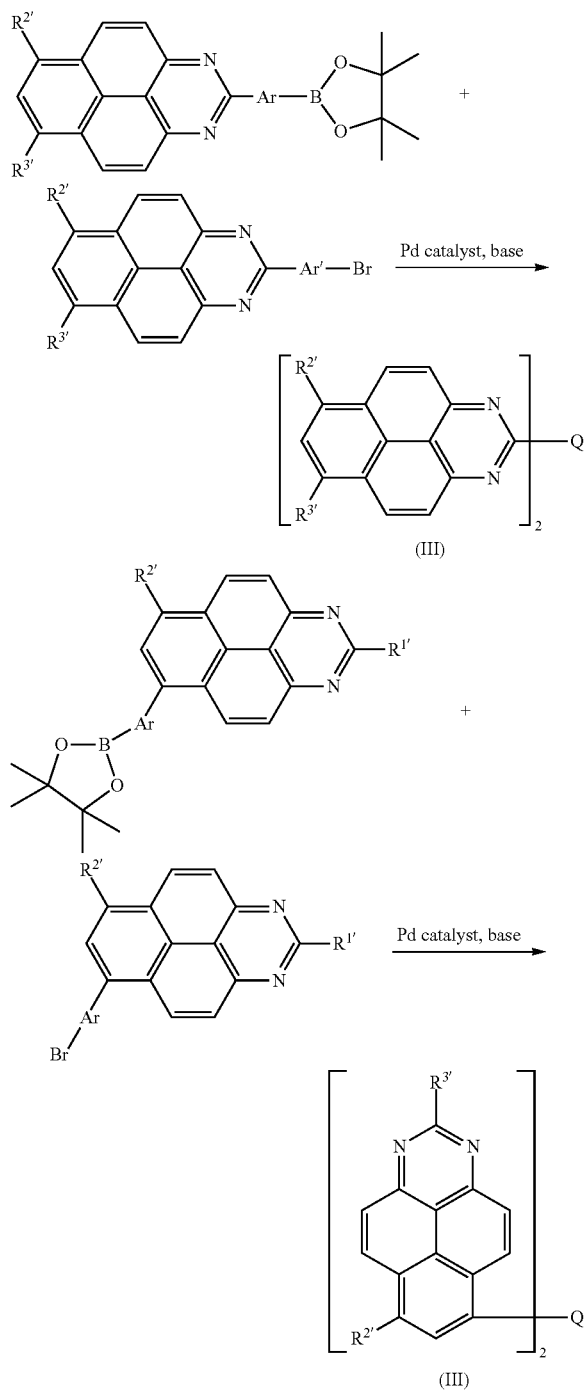

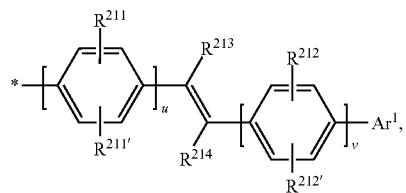

can be used as fluorescent emitters, especially in combination with a host material. Compounds of formula II, wherein $R^1$ is a group

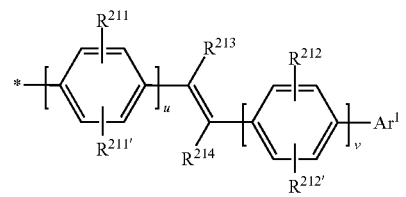

and $R^2$ and $R^3$ are independently of each other $C_6$-$C_{24}$aryl; $C_6$-$C_{24}$aryl which is substituted by $C_1$-$C_{18}$alkyl, or $C_1$-$C_{18}$alkoxy; are preferred.

u is 0, or 1; v is 0, or 1.

$R^{211}$, $R^{211'}$, $R^{212}$ and $R^{212'}$ are independently of each other H, $C_1$-$C_{18}$alkyl, or $C_1$-$C_{18}$alkoxy.

$R^{213}$ and $R^{214}$ are independently of each other H, or $C_1$-$C_{18}$alkyl.

$X^1$ is N or CH, especially CH. $R^5$, $R^6$, $R^7$ and $R^8$ are H.

$Ar^1$ is —$NR^{25'}R^{26'}$, $C_6$-$C_{24}$aryl, $C_6$-$C_{24}$aryl which substituted by G, $C_2$-$C_{20}$heteroaryl, or $C_2$-$C_{20}$heteroaryl which is substituted by G, preferably —$NR^{25'}R^{26'}$,

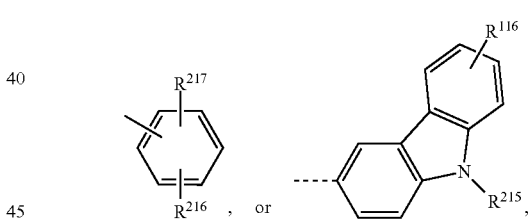

wherein $R^{25'}$ and $R^{26'}$ are as defined above.

Examples of such compounds are compounds B-26 to B-32 as shown in claim 6.

Compounds of the formula II

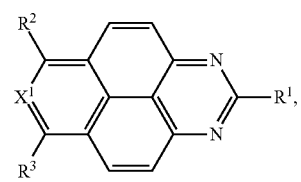

wherein
$R^5$, $R^6$, $R^7$ and $R^8$ are H,
$X^1$ is N or $CR^4$, especially N, CH, very especially CH,
$R^1$ to $R^4$ are independently of each other $C_6$-$C_{18}$aryl; $C_6$-$C_{18}$aryl which is substituted by $C_1$-$C_{18}$alkyl, or $C_1$-$C_{18}$alkoxy, especially $C_1$-$C_6$alkyl, $C_2$-$C_{20}$heteroaryl, The Suzuki reaction can be carried out as described in WO04039786. Ar and Ar' are an arylene, or heteroarylene radical, which together form the bridging unit Q after Suzuki coupling of the azapyrene carrying a boronic ester function and the bromoaryl azapyrene.

The electronic device of the present invention is preferably an electroluminescent (EL) device. The compounds of formula I, or III may be used in organic light emitting diodes (OLEDs) as hosts for phosphorescent compounds, as emitting and/or electron transport material.

Compounds of formula II, wherein at least one of $R^1$, $R^2$ and $R^3$ is a group of the formula $C_2$-$C_{20}$heteroaryl which is substituted by $C_1$-$C_{18}$alkyl, or $C_1$-$C_{18}$alkoxy, especially $C_1$-$C_6$alkyl; are preferred as host materials for fluorescent emitters.

Examples of such compounds are compounds A-1, B-1, B-2, B-9, B-34, B-35 and B-36 as shown in claim 6.

Compounds of the formula Ivb and Vc, wherein $X^1$ is N or $CR^4$, especially N, CH, very especially CH, $R^1$ to $R^4$ are independent of each other $C_6$-$C_{24}$aryl; $C_6$-$C_{24}$aryl which is substituted by $C_1$-$C_{18}$alkyl, or $C_1$-$C_{18}$alkoxy, especially $C_1$-$C_6$alkyl; $C_2$-$C_{20}$heteroaryl, $C_2$-$C_{20}$heteroaryl, which is substituted by $C_1$-$C_{18}$alkyl, or $C_1$-$C_{18}$alkoxy, especially $C_1$-$C_6$alkyl;

$R^{206}$ and $R^{207}$ are independently of each other $C_6$-$C_{24}$aryl; $C_6$-$C_{24}$aryl which is substituted by $C_1$-$C_{18}$alkyl, or $C_1$-$C_{18}$alkoxy, especially $C_1$-$C_6$alkyl; $C_2$-$C_{20}$heteroaryl, $C_2$-$C_{20}$heteroaryl, which is substituted by $C_1$-$C_{18}$alkyl, or $C_1$-$C_{18}$alkoxy, especially $C_1$-$C_6$alkyl; or CN; or $R^{206}$ and $R^{207}$ form together a group of formula

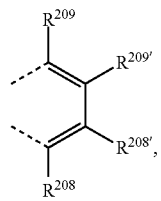

wherein $R^{209}$ and $R^{208}$ are H, $R^{209'}$ and $R^{208'}$ are independently of each other H, $C_1$-$C_{18}$alkyl, $C_1$-$C_{18}$alkyl which is interrupted by —O—, $C_1$-$C_{18}$alkoxy, $C_1$-$C_{18}$perfluoroalkyl, $C_6$-$C_{24}$aryl, $C_6$-$C_{24}$aryl which is substituted by $C_1$-$C_{18}$alkyl, or $C_1$-$C_{18}$alkoxy; $C_2$-$C_{20}$heteroaryl, or $C_2$-$C_{20}$heteroaryl, which is substituted by $C_1$-$C_{18}$alkyl, or $C_1$-$C_{18}$alkoxy; are suitable electron transporting materials in electronic applications. Such compounds can be used in OLEDs in electron transporting or injection layers. In this case the compound can be used alone or with a dopant. Such compounds are also useable as electron accepting materials in organic photovoltaic cells.

Examples of such compounds are compounds G-1 to G-5, H-1, H-2, K-1 to K-8, L-1 and L-2 as shown in claim 6.

Suitable dopants are alkali halides like LiF, NaF, KF, CsF, LiCl; alkali metal chalgonides like $Li_2O$, $K_2O$; $Cs_2O$, $CsCO_3$, alkali earth chalcogenides like CaO, BaO as described in US2008/018237. An example of an n-doped electron transport layer using Bphen doped with Li at a molar ratio of 1:1 is disclosed in U.S. Pat. No. 6,337,102. WO2009000237 disclose organic dopants and the use of such materials.

In one embodiment of the present invention the EL device comprises a cathode, an anode, and there between a light emitting layer containing a host material and a phosphorescent light-emitting material, wherein the host material is a compound of formula I, or III.

In another embodiment of the present invention the EL device comprises a cathode, an anode, and an electron transport material, wherein the electron transport material is, or comprises a compound of formula I, or III.

In another embodiment of the present invention the EL device comprises a cathode, an anode, and an emitting layer, wherein the emitting layer consists of, or comprises a compound of formula I, or III.

In another embodiment of the present invention the EL device, comprises a cathode, an anode, and there between a light emitting layer containing a material of formula I, or III, wherein compounds of formula I, or III are used as fluorescent host material or fluorescent light emitting material.

In addition, the present invention is also directed to the use of the compounds of formula I, or III for electrophotographic photoreceptors, photoelectric converters, solar cells, image sensors, dye lasers and electroluminescent devices.

Suitably, the light-emitting layer of the OLED device comprises a host material and one or more guest materials for emitting light. One of the host materials may be a compound of formula I, or III. The light-emitting guest material(s) is usually present in an amount less than the amount of host materials and is typically present in an amount of up to 15 wt % of the host, more typically from 0.1 to 10 wt % of the host, and commonly from 2 to 8% of the host. For convenience, the phosphorescent complex guest material may be referred to herein as a phosphorescent material. The emissive layer may comprise a single material, that combines transport and emissive properties. Whether the emissive material is a dopant or a major constituent, emissive layer may comprise other materials, such as dopants that tune the emission of the emissive layer. The emissive layer may include a plurality of emissive materials capable of, in combination, emitting a desired spectrum of light.

Other Host Materials for Phosphorescent Materials

The host material useful in the invention may be used alone or in combination with other host materials. Other host materials should be selected so that the triplet exciton can be transferred efficiently from the host material to the phosphorescent material. Suitable host materials are described in WO00/70655; 01/39234; 01/93642; 0/074015; 02/15645, and US20020117662. Suitable hosts include certain aryl amines, triazoles, indoles and carbazole compounds. Examples of hosts are 4,4'-N,N'-dicarbazole-biphenyl (CBP), 2,2'-dimethyl-4,4'-N,N'-dicarbazole-biphenyl, m-(N,N'-dicarbazole)benzene, and poly(N-vinylcarbazole), including their derivatives.

Desirable host materials are capable of forming a continuous film. The light-emitting layer may contain more than one host material in order to improve the device's film morphology, electrical properties, light emission efficiency, and lifetime. The light emitting layer may contain a first host material that has good hole-transporting properties, and a second host material that has good electron-transporting properties.

Phosphorescent Materials

Phosphorescent materials may be used alone or, in certain cases, in combination with each other, either in the same or different layers. Examples of phosphorescent and related materials are described in WO00/57676, WO00/70655, WO01/41512, WO02/15645, US2003/0017361, WO01/93642, WO01/39234, U.S. Pat. No. 6,458,475, WO02/071813, U.S. Pat. No. 6,573,651, US2002/0197511, WO02/074015, U.S. Pat. No. 6,451,455, US2003/0072964, US2003/0068528, U.S. Pat. Nos. 6,413,656, 6,515,298, 6,451,415, 6,097,147, US2003/0124381, US2003/0059646, US2003/0054198, EP1239526, EP1238981, EP1244155, US2002/0100906, US2003/0068526, US2003/0068535, JP2003073387, JP2003073388, US2003/0141809, US2003/0040627, JP2003059667, JP2003073665 and US2002/0121638.

The emission wavelengths of cyclometallated Ir(III) complexes of the type $IrL_3$ and $IrL_2L'$, such as the green-emitting fac-tris(2-phenylpyridinato-N,$C^{2'}$)iridium(III) and bis(2-phenylpyridinato-N,$C^{2'}$)Iridium(III) (acetylacetonate) may be shifted by substitution of electron donating or withdrawing groups at appropriate positions on the cyclometallating ligand L, or by choice of different heterocycles for the cyclometallating ligand L. The emission wavelengths may also be shifted by choice of the ancillary ligand L'. Examples of red emitters are the bis(2-(2'-benzothienyl)pyridinato-N,$C^{3'}$)iridium(El)(acetylacetonate) and tris(1-phenylisoquinolinato-N,C)iridium(III). A blue-emitting example is bis(2-(4,6-difluorophenyl)-pyridinato-N,$C^{2'}$)Iridium(III)(picolinate).

Red electrophosphorescence has been reported, using bis (2-(2'-benzo[4,5-a]thienyl)pyridinato-N, $C^3$)iridium(acetylacetonate)[$Btp_2Ir(acac)$] as the phosphorescent material (Adachi, C., Lamansky, S., Baldo, M. A., Kwong, R. C., Thompson, M. E., and Forrest, S. R., App. Phys. Lett., 78, 1622 1624 (2001).

Other important phosphorescent materials include cyclometallated Pt(II) complexes such as cis-bis(2-phenylpyridinato-N,$C^{2'}$)platinum(II), cis-bis(2-(2'-thienyl)pyridinato-N, $C^{3'}$) platinum(II), cis-bis(2-(2'-thienyl)quinolinato-N,$C^{5'}$) platinum(II), or (2-(4,6-difluorophenyl)pyridinato-NC2') platinum(II)acetylacetonate. Pt(II)porphyrin complexes such as 2,3,7,8,12,13,17,18-octaethyl-21H, 23H-porphine platinum(H) are also useful phosphorescent materials.

Still other examples of useful phosphorescent materials include coordination complexes of the trivalent lanthanides such as $Th^{3+}$ and $Eu^{3+}$ (J. Kido et al, Appl. Phys. Lett., 65, 2124 (1994)).

Other important phosphorescent materials are described in WO06/000544 and European patent application no. 07102949.0.

Examples of phosphorescent materials are compounds A-1 to B-234, B-1 to B-234, C-1 to C-44 and D-1 to D-234, which are described in WO08/101,842, and compounds A1-A144 and B1-B144, which are described in PCT/EP2009/051109.

Blocking Layers

In addition to suitable hosts, an OLED device employing a phosphorescent material often requires at least one exciton or hole blocking layers to help confine the excitons or electron-hole recombination centers to the light-emitting layer comprising the host and phosphorescent material, or to reduce the number of charge carriers (electrons or holes). In one embodiment, such a blocking layer would be placed between the electron-transporting layer and the light-emitting layer. In this case, the ionization potential of the blocking layer should be such that there is an energy barrier for hole migration from the host into the electron-transporting layer, while the electron affinity should be such that electrons pass more readily from the electron-transporting layer into the light-emitting layer comprising host and phosphorescent material. It is further desired, but not absolutely required, that the triplet energy of the blocking material be greater than that of the phosphorescent material. Suitable hole-blocking materials are described in WO00/70655 and WO01/93642. Two examples of useful materials are bathocuproine (BCP) and bis(2-methyl-8-quinolinolato)(4-phenylphenolato)aluminum(III) (BalQ). Metal complexes other than Balq are also known to block holes and excitons as described in US20030068528. US20030175553 describes the use of factris(1-phenylpyrazolato-N,C 2)iridium(III) (Irppz) in an electron/exciton blocking layer.

Embodiments of the invention can provide advantageous features such as operating efficiency, higher luminance, color hue, low drive voltage, and improved operating stability. Embodiments of the organometallic compounds useful in the invention can provide a wide range of hues including those useful in the emission of white light (directly or through filters to provide multicolor displays).

General Device Architecture

The compounds of the present invention can be employed in many OLED device configurations using small molecule materials, oligomeric materials, polymeric materials, or combinations thereof. These include very simple structures comprising a single anode and cathode to more complex devices, such as passive matrix displays comprised of orthogonal arrays of anodes and cathodes to form pixels, and active-matrix displays where each pixel is controlled independently, for example, with thin film transistors (TFTs).

There are numerous configurations of the organic layers. The essential requirements of an OLED are an anode, a cathode, and an organic light-emitting layer located between the anode and cathode. Additional layers may be employed as more fully described hereafter.

A typical structure, especially useful for of a small molecule device, is comprised of a substrate, an anode, a hole-injecting layer, a hole-transporting layer, a light-emitting layer, optionally a hole- or exciton-blocking layer, an electron-transporting layer, and a cathode. These layers are described in detail below. Note that the substrate may alternatively be located adjacent to the cathode, or the substrate may actually constitute the anode or cathode. The organic layers between the anode and cathode are conveniently referred to as the organic EL element. Also, the total combined thickness of the organic layers is desirably less than 500 nm.

Compounds of formula IIa may be used as host in the light-emitting layer (emissive layer).

Compounds of formula IIa and IIb may be used in the electron transport layer, optionally in combination with a dopant.

In a preferred embodiment the device comprises in this order a glass substrate, an anode (indium tin oxide (ITO)), a hole injection layer (2-TNATA (4,4',4"-tris(N-(naphtha-2-yl)-N-phenyl-amino)triphenylamine; α-NPD doped with organic or inorganic dopants), a hole transport layer (4,4'-bis [N-(1-naphtyl)-N-phenylamino]biphenyl (α-NPD)), an emissive layer (aluminum(III) bis(2-methyl-8-hydroxyquinolinato)-4-phenylphenolate (BalQ), α-NPD, Cpd. A-1, or Cpd. A-19 doped with bis(1-phenylisoquinoline) (acetylacetonate)iridium(III), or iridium(III)bis-(2-methyldibenzo [th]quinoxaline) (acetylacetonate)), a electron transport layer (BalQ/$AlQ_3$; $AlQ_3$; Cpd. of A-1/$AlQ_3$; 1,3,5-tris(N-phenyl-benzimidazol-2-yl)benzene (TPBI)/Cpd. A-1; TPBI/$AlQ_3$; Cpd. B-38; BalQ/BCP doped with $Cs_2CO_3$ or organic dopants; BalQ/Cpd. A-1 doped with $Cs_2CO_3$ or organic dopants; BalQ/Cpd. of B-38 doped with $Cs_2CO_3$ or organic dopants; Cpd. B-1; Cpd. B-39; BalQ/Cpd. of B-1), and a cathode LiF/Al or $Cs_2CO_3$/Al. Examples of p-dopants are, for example, mentioned in K. Walzer, B. Maennig, M. Pfeiffer, and K. Leo, Chem. Rev. 107 (2007) 1233-1271, EP1596445A1, WO2009/003455A1, DE100357044, WO2008/058525, WO2008/138580, US20080171228 and US2008/0265216. Suitable n-dopants are alkali halides like LiF, NaF, KF, CsF, LiCl; alkali metal chalgonides like $Li_2O$, $K_2O$; $Cs_2O$, $Cs_2CO_3$, alkali earth chalcogenides like CaO, BaO as described in WO2008/018237. An example of an n-doped electron transport layer using Bphen doped with Li at a molar ratio of 1:1 is disclosed in U.S. Pat. No. 6,337,102. WO2009000237 discloses organic dopants and the use of such materials.

Substrate

The substrate can either be light transmissive or opaque, depending on the intended direction of light emission. The light transmissive property is desirable for viewing the EL emission through the substrate. Transparent glass or plastic is commonly employed in such cases. The substrate can be a complex structure comprising multiple layers of materials. This is typically the case for active matrix substrates wherein TFTs are provided below the OLED layers. It is still necessary that the substrate, at least in the emissive pixilated areas, be comprised of largely transparent materials such as glass or polymers. For applications where the EL emission is viewed through the top electrode, the transmissive characteristic of the bottom support is immaterial, and therefore can be light transmissive, light absorbing or light reflective. Substrates for use in this case include, but are not limited to, glass, plastic, semiconductor materials, silicon, ceramics, and circuit board materials. Again, the substrate can be a complex structure comprising multiple layers of materials such as found in active matrix TFT designs. It is necessary to provide in these device configurations a light-transparent top electrode.

Anode

When the desired electroluminescent light emission (EL) is viewed through the anode, the anode should be transparent or substantially transparent to the emission of interest. Common transparent anode materials used in this invention are indium-tin oxide (ITO), indium-zinc oxide (IZO) and tin oxide, but other metal oxides can work including, but not limited to, aluminium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulphide, can be used as the anode. For applications where EL emission is viewed only through the cathode, the transmissive characteristics of the anode are immaterial and any conductive material can be used, transparent, opaque or reflective. Example conductors for this application include, but are not limited to, gold, iridium, molybdenum, palladium, and platinum. Desired anode materials are commonly deposited by any suitable means such as evaporation, sputtering, chemical vapor deposition, or electrochemical means. Anodes can be patterned using well-known photolithographic processes. Optionally, anodes may be polished prior to application of other layers to reduce surface roughness so as to minimize shorts or enhance reflectivity.

Cathode

When light emission is viewed solely through the anode, the cathode used in this invention can be comprised of nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One useful cathode material is comprised of a Mg:Ag alloy wherein the percentage of silver is in the range of 1 to 20%, as described in U.S. Pat. No. 4,885,221. Another suitable class of cathode materials includes bilayers comprising the cathode and a thin electron-injection layer (EIL) in contact with an organic layer (e.g., an electron transporting layer (ETL)) which is capped with a thicker layer of a conductive metal. Here, the EIL preferably includes a low work function metal or metal salt, and if so, the thicker capping layer does not need to have a low work function. One such cathode is comprised of a thin layer of LiF followed by a thicker layer of Al as described in U.S. Pat. No. 5,677,572. An ETL material doped with an alkali metal, for example, $L_1$-doped Alq, is another example of a useful EIL. Other useful cathode material sets include, but are not limited to, those disclosed in U.S. Pat. Nos. 5,059,861, 5,059,862 and 6,140,763.

When light emission is viewed through the cathode, the cathode must be transparent or nearly transparent. For such applications, metals must be thin or one must use transparent conductive oxides, or a combination of these materials. Optically transparent cathodes have been described in more detail in U.S. Pat. Nos. 4,885,211, 5,247,190, JP 3,234,963, U.S. Pat. Nos. 5,703,436, 5,608,287, 5,837,391, 5,677,572, 5,776,622, 5,776,623, 5,714,838, 5,969,474, 5,739,545, 5,981,306, 6,137,223, 6,140,763, 6,172,459, EP1076368, U.S. Pat. Nos. 6,278,236 and 6,284,3936. Cathode materials are typically deposited by any suitable method such as evaporation, sputtering, or chemical vapour deposition. When needed, patterning can be achieved through many well known methods including, but not limited to, through-mask deposition, integral shadow masking as described in U.S. Pat. No. 5,276,380 and EP0732868, laser ablation, and selective chemical vapour deposition.

Hole-Injecting Layer (HIL)

A hole-injecting layer may be provided between anode and hole-transporting layer. The hole-injecting material can serve to improve the film formation property of subsequent organic layers and to facilitate injection of holes into the hole-transporting layer. Suitable materials for use in the hole-injecting layer include, but are not limited to, porphyrinic compounds as described in U.S. Pat. No. 4,720,432, plasma-deposited fluorocarbon polymers as described in U.S. Pat. No. 6,208,075, and some aromatic amines, for example, m-MTDATA (4,4',4"-tris[(3-methylphenyl)phenylamino]triphenylamine), or 2-TNATA (4,4',4"-tris(N-(naphtha-2-yl)-N-phenyl-amino)triphenylamine). Alternative hole-injecting materials reportedly useful in organic EL devices are described in EP0891121 and EP1029909.

Hole-Transporting Layer (HTL)

The hole-transporting layer of the organic EL device contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated in U.S. Pat. No. 3,180,730. Other suitable triarylamines substituted with one or more vinyl radicals and/or comprising at least one active hydrogen containing group are disclosed in U.S. Pat. Nos. 3,567,450 and 3,658,520. A more preferred class of aromatic tertiary amines are those which include at least two aromatic tertiary amine moieties as described in U.S. Pat. Nos. 4,720,432 and 5,061,569. Such compounds include those represented by structural formula

(A)

wherein $Q^1$ and $Q^2$ are independently selected aromatic tertiary amine moieties and G is a linking group such as an arylene, cycloalkylene, or alkylene group of a carbon to carbon bond. In one embodiment, at least one of $Q^1$ or $Q^2$ contains a polycyclic fused ring structure, e.g., a naphthalene. When G is an aryl group, it is conveniently a phenylene, biphenylene, or naphthalene moiety.

A useful class of triarylamines satisfying structural formula (A) and containing two triarylamine moieties is represented by structural formula

(B)

where $Q^3$ and $Q^4$ each independently represents a hydrogen atom, an aryl group, or an alkyl group or $Q^3$ and $Q^4$ together represent the atoms completing a cycloalkyl group; and $Q^5$ and $Q^6$ each independently represents an aryl group, which is in turn substituted with a diaryl substituted amino group, as indicated by structural formula

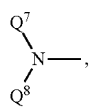
(C)

wherein $Q^7$ and $Q^8$ are independently selected aryl groups. In one embodiment, at least one of $Q^7$ or $Q^8$ contains a polycyclic fused ring structure, e.g., a naphthalene.

Another class of aromatic tertiary amines are the tetraaryldiamines. Desirable tetraaryldiamines include two diarylamino groups, such as indicated by formula I, linked through an arylene group. Useful tetraaryldiamines include those represented by formula

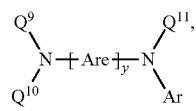
(D)

wherein each Are is an independently selected arylene group, such as a phenylene or anthracene moiety, y is an integer of from 1 to 4, and Ar, $Q^9$, $Q^{10}$, and $Q^{11}$ are independently selected aryl groups. In a typical embodiment, at least one of Ar, $Q^9$, $Q^{10}$, and $Q^{11}$ is a polycyclic fused ring structure, e.g., a naphthalene. The various alkyl, alkylene, aryl, and arylene moieties of the foregoing structural formulae (A), (B), (C), (D), can each in turn be substituted. Typical substituents include alkyl groups, alkoxy groups, aryl groups, aryloxy groups, and halogen such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms, e.g. cyclopentyl, cyclohexyl, and cycloheptyl ring structures. The aryl and arylene moieties are usually phenyl and phenylene moieties.

The hole-transporting layer can be formed of a single or a mixture of aromatic tertiary amine compounds. Specifically, one may employ a triarylamine, such as a triarylamine satisfying the formula (B), in combination with a tetraaryldiamine, such as indicated by formula (D). When a triarylamine is employed in combination with a tetraaryldiamine, the latter is positioned as a layer interposed between the triarylamine and the electron injecting and transporting layer. Illustrative of useful aromatic tertiary amines are the following: 1,1-Bis(4-di-p-tolylaminophenyl)cyclohexane, 1,1-bis (4-di-p-tolylaminophenyl)-4-phenylcyclohexane, N,N,N', N'-tetraphenyl-4,4'''-diamino-1,1':4',":4''', 1'''-quaterphenyl bis(4-dimethylamino-2-methylphenyl)phenylmethane, 1,4-bis[2-[4-[N,N-di(p-toly)amino]phenyl]vinyl]benzene (BDTAPVB), N,N,N',N'-tetra-p-tolyl-4,4'-diaminobiphenyl, N,N,N',N'-tetraphenyl-4,4'-diaminobiphenyl, N,N,N',N'-tetra-1-naphthyl-4,4'-diaminobiphenyl, N,N,N',N'-tetra-2-naphthyl-4,4'-diaminobiphenyl, N-phenylcarbazole, 4,4'-bis [N-(1-naphthyl)-N-phenylamino]biphenyl (α-NPD), 4,4'-bis [N-(1-naphthyl)-N-(2-naphthyl)amino]biphenyl (TNB), 4,4'-bis[N-(1-naphthyl)-N-phenylamino]p-terphenyl, 4,4'-bis[N-(2-naphthyl)-N-phenylamino]biphenyl, 4,4'-bis[N-(3-acenaphthenyl)-N-phenylamino]biphenyl, 1,5-bis[N-(1-naphthyl)-N-phenylamino]naphthalene, 4,4'-bis[N-(9-anthryl)-N-phenylamino]biphenyl, 4,4'-bis[N-(1-anthryl)-N-phenylamino]-p-terphenyl, 4,4'-bis[N-(2-phenanthryl)-N-phenylamino]biphenyl, 4,4'-bis[N-(8-fluoranthenyl)-N-phenylamino]biphenyl, 4,4'-bis[N-(2-pyrenyl)-N-phenylamino]biphenyl, 4,4'-bis[N-(2-naphthacenyl)-N-phenylamino]biphenyl, 4,4'-bis[N-(2-perylenyl)-N-phenylamino]biphenyl, 4,4'-bis[N-(1-coronenyl)-N-phenylamino]biphenyl, 2,6-bis(di-p-tolylamino) naphthalene, 2,6-bis[di-(1-naphthyl)amino]naphthalene, 2,6-bis[N-(1-naphthyl)-N-(2-naphthyl)amino]naphthalene, N,N,N',N'-tetra(2-naphthyl)-4,4''-diamino-p-terphenyl, 4,4'-bis {N-phenyl-N-[4-(1-naphthyl)-phenyl]amino}biphenyl, 2,6-bis[N,N-di(2-naphthyl)amino]fluorine, 4,4',4''-tris[(3-methylphenyl)phenylamino]triphenylamine (MTDATA), and 4,4'-Bis[N-(3-methylphenyl)-N-phenylamino]biphenyl (TPD). A hole transport layer may be used to enhance conductivity. α-NPD and TPD are examples of intrinsic hole transport layers. An example of a p-doped hole transport layer is m-MTDATA doped with $F_4$-TCNQ at a molar ratio of 50:1 as disclosed in U.S. Pat. No. 6,337,102 or DE10058578.

Another class of useful hole-transporting materials includes polycyclic aromatic compounds as described in EP1009041. Tertiary aromatic amines with more than two amine groups may be used including oligomeric materials. In addition, polymeric hole-transporting materials can be used such as poly(N-vinylcarbazole) (PVK), polythiophenes, polypyrrole, polyaniline, and copolymers such as poly(3,4-ethylenedioxythiophene)/poly(4-styrenesulfonate) also called PEDOT/PSS.

Fluorescent Light-Emitting Materials and Layers (LEL)

In addition to the phosphorescent materials, other light emitting materials may be used in the OLED device, including fluorescent materials. The compounds of formula I and III may function as fluorescent light-emitting materials. Although the term "fluorescent" is commonly used to describe any light emitting material, in this case we are referring to a material that emits light from a singlet excited state. Fluorescent materials may be used in the same layer as the phosphorescent material, in adjacent layers, in adjacent pixels, or any combination. Care must be taken not to select materials that will adversely affect the performance of the phosphorescent materials. One skilled in the art will understand that triplet excited state energies of materials in the same layer as the phosphorescent material or in an adjacent layer must be appropriately set so as to prevent unwanted quenching. As more fully described in U.S. Pat. Nos. 4,769, 292 and 5,935,721, the light-emitting layer (LEL) of the organic EL element includes a luminescent fluorescent or phosphorescent material where electroluminescence is produced as a result of electron-hole pair recombination in this region. The light-emitting layer can be comprised of a single material, but more commonly consists of a host material doped with a guest emitting material or materials where light emission comes primarily from the emitting materials and can be of any color. The host materials in the light-emitting layer can be an electron-transporting material, as defined below, a hole-transporting material, as defined above, or another material or combination of materials that support hole-electron recombination. Fluorescent emitting materials are typically incorporated at 0.01 to 10% by weight of the host material. The host and emitting materials can be small nonpolymeric molecules or polymeric materials such as polyfluorenes and polyvinylarylenes (e.g., poly(p-phenylenevinylene), PPV). In the case of polymers, small molecule emitting materials can be molecularly dispersed into a polymeric host, or the emitting materials can be added by copolymerizing a minor constituent into a host polymer. Host materials may be mixed together in order to improve film formation, electrical properties, light emission efficiency, lifetime, or manufacturability. The host may comprise a material that has good hole-transporting properties and a material that has good electron-transporting properties.

Host and emitting materials known to be of use include, but are not limited to, those disclosed in U.S. Pat. Nos. 4,768,292, 5,141,671, 5,150,006, 5,151,629, 5,405,709, 5,484,922, 5,593,788, 5,645,948, 5,683,823, 5,755,999, 5,928,802, 5,935,720, 5,935,721, and 6,020,078.

Metal complexes of 8-hydroxyquinoline and similar derivatives (Formula E) constitute one class of useful host compounds capable of supporting electroluminescence, and are particularly suitable for light emission of wavelengths longer than 500 nm, e.g., green, yellow, orange, and red.

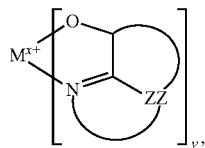

wherein M represents a metal; v is an integer of from 1 to 4; and ZZ independently in each occurrence represents the atoms completing a nucleus having at least two fused aromatic rings. From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; an earth metal, such as aluminium or gallium, or a transition metal such as zinc or zirconium. Generally any monovalent, divalent, trivalent, or tetravalent metal known to be a useful chelating metal can be employed. ZZ completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less.

Illustrative of useful chelated oxinoid compounds are the following:

CO-1: Aluminum trisoxine [alias, tris(8-quinolinolato)aluminum(III)]
CO-2: Magnesium bisoxine [alias, bis(8-quinolinolato)magnesium(II)]
CO-3: Bis[benzo{f}-8-quinolinolato]zinc(II)
CO-4: Bis(2-methyl-8-quinolinolato)aluminium(III)-μ-oxo-bis(2-methyl-8-quinolinolato)aluminium(III)
CO-5: Indium trisoxine [alias, tris(8-quinolinolato)indium]
CO-6: Aluminum tris(5-methyloxine) [alias, tris(5-methyl-8-quinolinolato) aluminum(III)]
CO-7: Lithium oxine [alias, (8-quinolinolato)lithium(I)]
CO-8: Gallium oxine [alias, tris(8-quinolinolato)gallium (III)]
CO-9: Zirconium oxine [alias, tetra(8-quinolinolato)zirconium(IV)]

Useful fluorescent emitting materials include, but are not limited to, derivatives of anthracene, tetracene, xanthene, perylene, rubrene, coumarin, rhodamine, and quinacridone, dicyanomethylenepyran compounds, thiopyran compounds, polymethine compounds, pyrilium and thiapyrilium compounds, fluorene derivatives, periflanthene derivatives, indenoperylene derivatives, bis(azinyl)amine boron compounds, bis(azinyl)methane compounds, and carbostyryl compounds. Illustrative examples of useful materials include, but are not limited to, compounds $L_1$ to $L_{52}$ described in U.S. Pat. No. 7,090,930B2.

Electron-Transporting Layer (ETL)

Preferred thin film-forming materials for use in forming the electron-transporting layer of the organic EL devices of this invention are metal chelated oxinoid compounds, including chelates of oxine itself (also commonly referred to as 8-quinolinol or 8-hydroxyquinoline). Such compounds help to inject and transport electrons and exhibit both high levels of performance and are readily fabricated in the form of thin films. Exemplary of contemplated oxinoid compounds are those satisfying structural formula (E), previously described. Other electron-transporting materials include various butadiene derivatives as disclosed in U.S. Pat. No. 4,356,429 and various heterocyclic optical brighteners as described in U.S. Pat. No. 4,539,507. Benzazoles satisfying structural formula (G) are also useful electron transporting materials. Triazines are also known to be useful as electron transporting materials. Doping may be used to enhance conductivity. $Alq_3$ is an example of an intrinsic electron transport layer. An example of an n-doped electron transport layer is Bphen doped with Li at a molar ratio of 1:1, as disclosed in U.S. Pat. No. 6,337,102.

Deposition of Organic Layers

The organic materials mentioned above are suitably deposited by any means suitable for the form of the organic materials. In the case of small molecules, they are conveniently deposited through thermal evaporation, but can be deposited by other means such as from a solvent with an optional binder to improve film formation. If the material is soluble or in oligomeric/polymeric form, solution processing is usually preferred e.g. spin-coating, ink-jet printing. Dendrimer substituents may be used to enhance the ability of small molecules to undergo solution processing. Patterned deposition can be achieved using shadow masks, integral shadow masks (U.S. Pat. No. 5,294,870), spatially-defined thermal dye transfer from a donor sheet (U.S. Pat. Nos. 5,688,551, 5,851, 709 and 6,066,357) and inkjet method (U.S. Pat. No. 6,066, 357).

Encapsulation

Most OLED devices are sensitive to moisture or oxygen, or both, so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890. In addition, barrier layers such as $SiO_x$, Teflon, and alternating inorganic/polymeric layers are known in the art for encapsulation.

Devices fabricated in accordance with embodiments of the invention may be incorporated into a wide variety of consumer products, including flat panel displays, computer monitors, televisions, billboards, lights for interior or exterior illumination and/or signalling, fully transparent displays, flexible displays, laser printers, cell phones, personal digital assistants (PDAs), laptop computers, digital cameras, camcorders, viewfinders, micro-displays, vehicles, theatre or stadium screen, or a sign. Various control mechanism may be used to control devices fabricated in accordance with the present invention, including passive matrix and active matrix.

Various features and aspects of the present invention are illustrated further in the examples that follow. While these examples are presented to show one skilled in the art how to operate within the scope of this invention, they are not to serve as a limitation on the scope of the invention where such scope is only defined in the claims. Unless otherwise indicated in the following examples and elsewhere in the specification and claims, all parts and percentages are by weight, temperatures are in degrees centigrade and pressures are at or near atmospheric.

EXAMPLES

Example 1

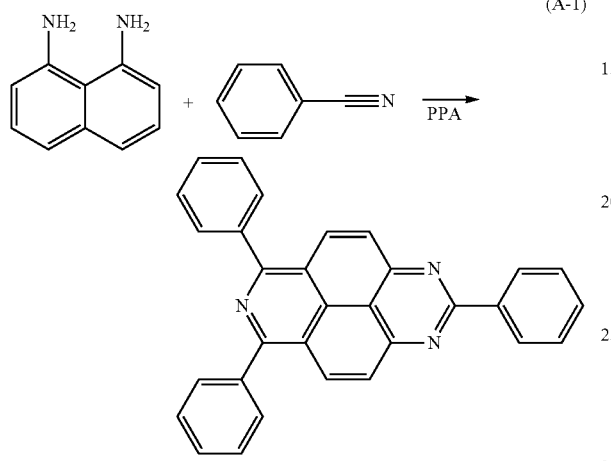

(A-1)

The product is prepared according to Chemistry of Heterocyclic Compounds 43 (2007) 665: To 5.00 g (31.6 mmol) naphthalene-1,8-diamine and 16.3 g (158 mmol) benzonitrile 50 g poly phosphoric acid are added. The reaction mixture is heated under nitrogen for 18 h at 180° C. The heating bath is removed and 50 ml ethanol are added. The reaction mixture is poured into water and neutralized with aqueous ammonia solution. The product is filtered off and is washed with water and water/ethanol 1/1. The product is dissolved in toluene and is filtered on silica gel. The solvent is removed in vacuum and the product is soxhlet extracted with ethyl acetate (yield: 1.26 g (9.2%)). Melting point: 295.0-296.0° C.

Example 2

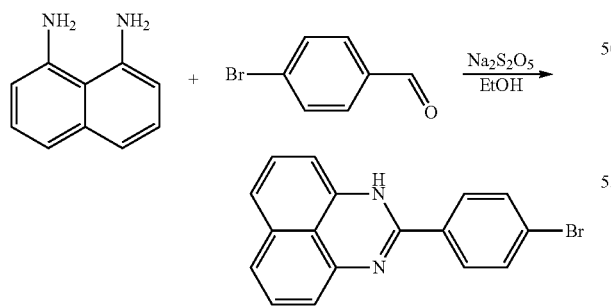

a) 10.0 g (63.2 mmol) naphthalene-1,8-diamine, 12.9 g (69.5 mmol) 4-bromo-benzaldehyde and 13.2 g (69.5 mmol) sodium disulfite are dissolved in 150 ml ethanol. The reaction mixture is refluxed for 3 h under nitrogen and cooled to 25° C. The product is filtered off and washed with water and ethanol (yield: 14.4 g (71%)).

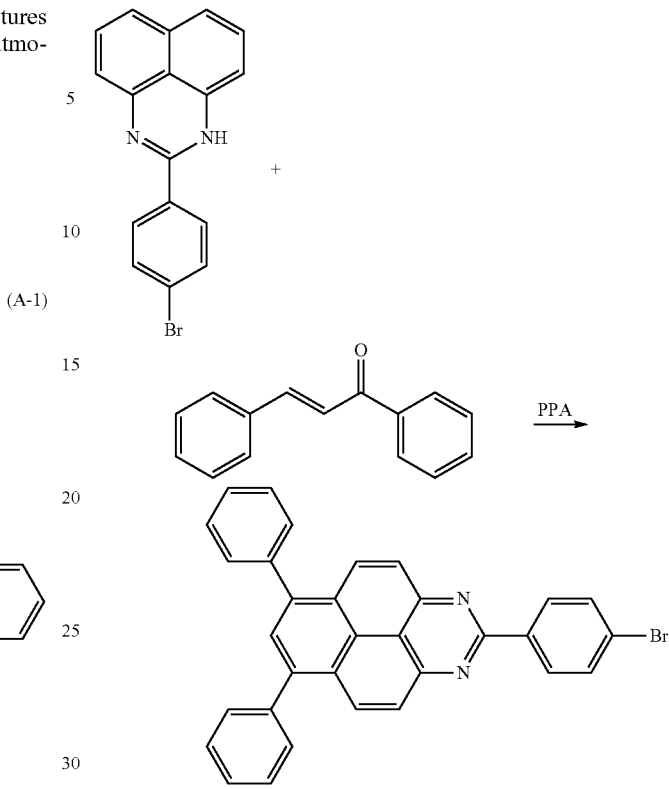

b) 1.00 g (3.09 mmol) of the product of example 2a and 0.710 g (3.40 mmol) (E)-1,3-diphenyl-propenone are added to a mixture of 10 g polyphosphoric acid and 5 ml toluene. The reaction mixture is stirred for 6 h at 90° C. under nitrogen. 20 ml ethanol and 30 ml water are added. The suspension is poured into water. The water phase is neutralized with an aqueous ammonia solution. The product is filtered off, washed with water, ethanol and again water (yield: 0.66 g (42%)).

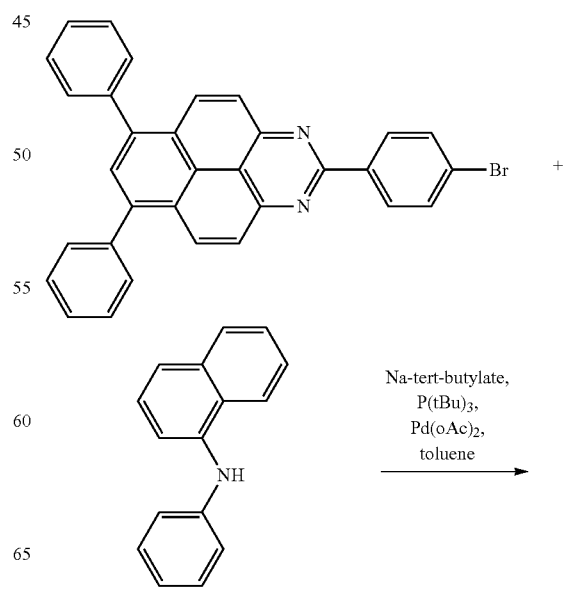

(A-19)

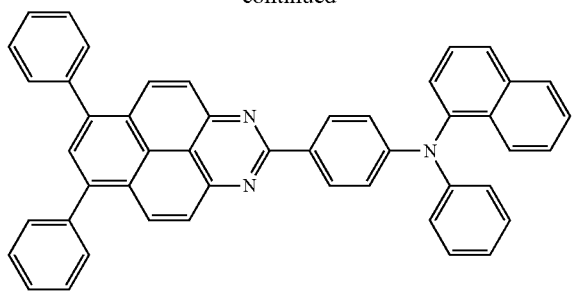
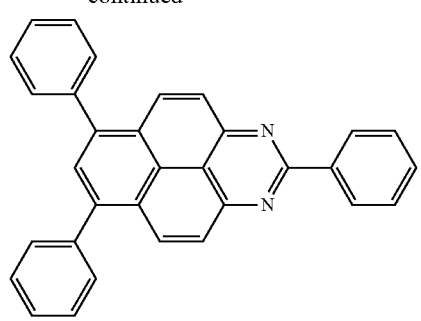

c) 3.00 g (5.86 mmol) of the product of example 2b, 1.41 g (6.45 mmol) naphthalene-1-yl-phenyl-amine and 620 mg (6.45 mmol) sodium tert-butylate are dissolved in 80 ml toluene. The reaction mixture is degassed with argon. 66 mg (0.29 mmol) palladium (II) acetate are added. The reaction mixture is degassed with argon. 119 mg (0.59 mmol) tri-tert-butylphosphane are added. The reaction mixture is degassed with argon, stirred for 3 h at 90° C. under argon, then cooled to 25° C. and washed with a 1% aqueous sodium cyanide solution. The organic phase is separated and the solvent is removed. Column chromatography on silica gel with toluene/hexane 3/7 result in the product (yield: 870 mg (23%)). Melting point: 309.5° C.

b) 20 g polyphosphoric acid and 10 ml toluene are added to 2.00 g (8.19 mmol) of the product of example 1a and 1.88 g (9.01 mmol) (E)-1,3-diphenyl-propenone. The reaction mixture is stirred at 80° C. under nitrogen for 18 h. The heating bath is removed and 60 ml water are added. The suspension is poured into water. The water phase is neutralized with an aqueous ammonia solution. The product is filtered off and washed with ethanol and soxhlet extracted with ethyl acetate (yield: 1.10 g (31%)). Melting point: 273.0-274.5° C.

Example 4

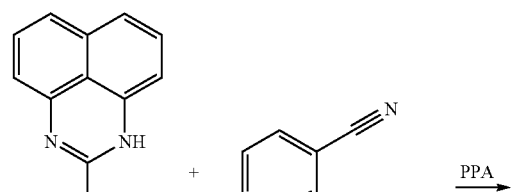

Example 3

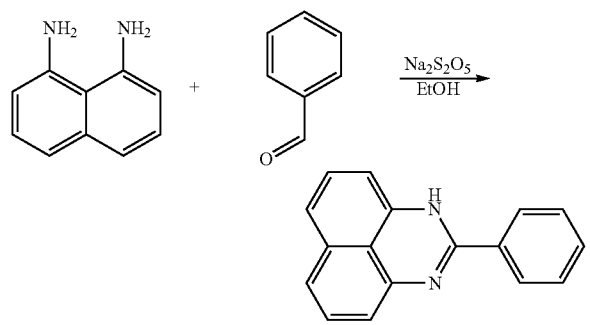

a) 50 ml ethanol are added to 3.60 g (22.8 mmol) naphthalene-1,8-diamine, 2.66 g (25.0 mmol) benzaldehyde, and 4.76 g (25.0 mmol) sodium disulfite. The reaction mixture is refluxed for 2.5 h. The product is filtered off and is washed with ethanol and water (yield: 89%.

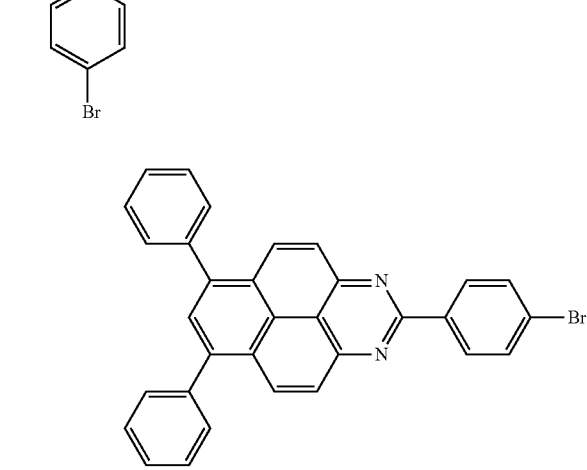

(B-1)

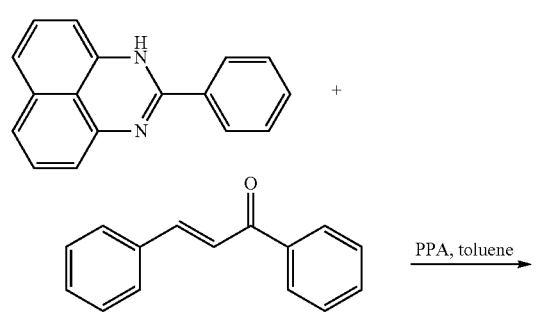

20 g polyphosphoric acid are added to 2.00 g (6.19 mmol) of the product of example 2a and 2.55 g (24.8 mmol) benzonitrile. The reaction mixture is stirred at 180° C. under nitrogen for 17 h. The heating bath is removed and 20 ml ethanol and 30 ml water are added. The suspension is poured into water and the water phase is neutralized with an aqueous ammonia solution. The product is filtered off, washed with water, ethanol and again water and Soxhlet extracted with ethyl acetate (yield: 1.83 g (58%)).

Example 5

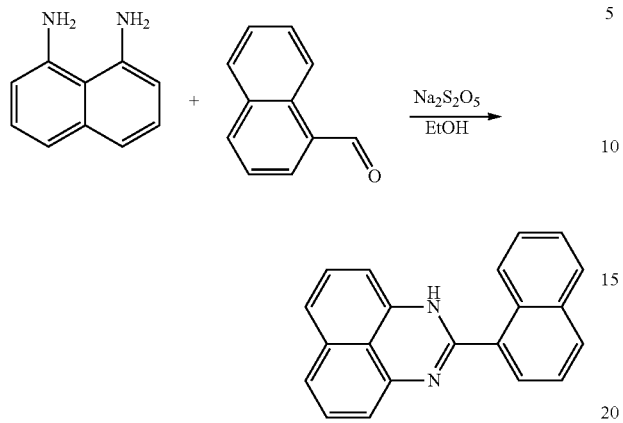

a) 100 ml ethanol are added to 20.0 g (126 mmol) naphthalene-1,8-diamine, 21.7 g (139 mmol) naphthalene-1-carbaldehyde and 26.4 g (139 mmol) sodium disulfite. The reaction mixture is refluxed for 6 h under nitrogen. The product is filtered off and is washed with ethanol and water (yield: 25.6 g (69%)). The product is used without further purification in the next reaction step.

(B-37)

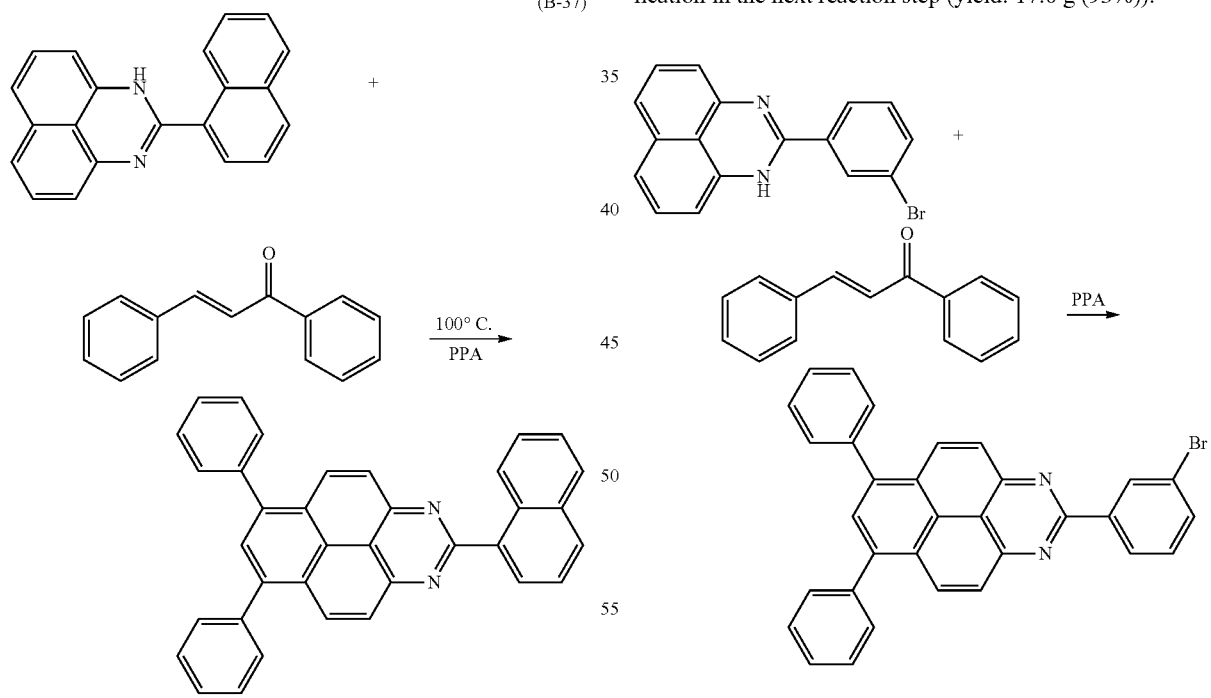

b) 2 g (6.79 mmol) of the product of example 5a, 1.56 g (7.47 mmol) (E)-1,3-diphenyl-propenone are added to a mixture of 20 g polyphosphoric acid and 3 ml toluene. The reaction mixture is heated at 100° C. for 57 h and poured into water. The water phase is neutralized with an aqueous ammonia solution. The product is filtered off, washed with water and ethanol, decocted two times with ethyl acetate, soxhlet extracted with ethyl acetate, filtered on silica gel with toluene and decocted with diethyl ether (yield: 830 mg (25%)). Melting point: 260-261° C.

Example 6

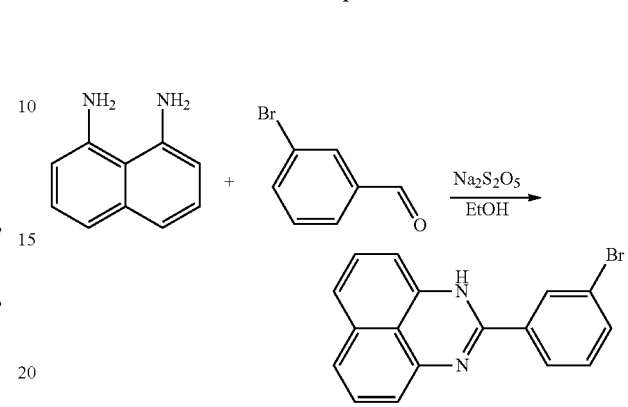

a) 300 ml ethanol are added to 9.00 g (56.9 mmol) naphthalene-1,8-diamine, 11.6 g (62.6 mmol) 3-bromo-benzaldehyde and 11.9 g (62.6 mmol) sodium disulfite. The reaction mixture is refluxed for 14 h under nitrogen and is filtered hot. The solids are washed with ethanol. The ethanol phase is collected. The ethanol is partly distilled off and the ethanol solution is poured into water. The product is filtered off and is washed with water. The product is used without further purification in the next reaction step (yield: 17.0 g (93%)).

b) 5 g (15.5 mmol) of the product of example 6a, 3.54 g (17.0 mmol) (E)-1,3-diphenyl-propenone are added to a mixture of 50 g polyphosphoric acid and 2 ml toluene. The reaction mixture is heated at 100° C. for 22 h under nitrogen and is poured into water. The water phase is neutralized with an aqueous ammonia solution. The product is filtered off, washed with water and ethanol and decocted with ethanol. Yield 3.82 g (48%).

(B-38)

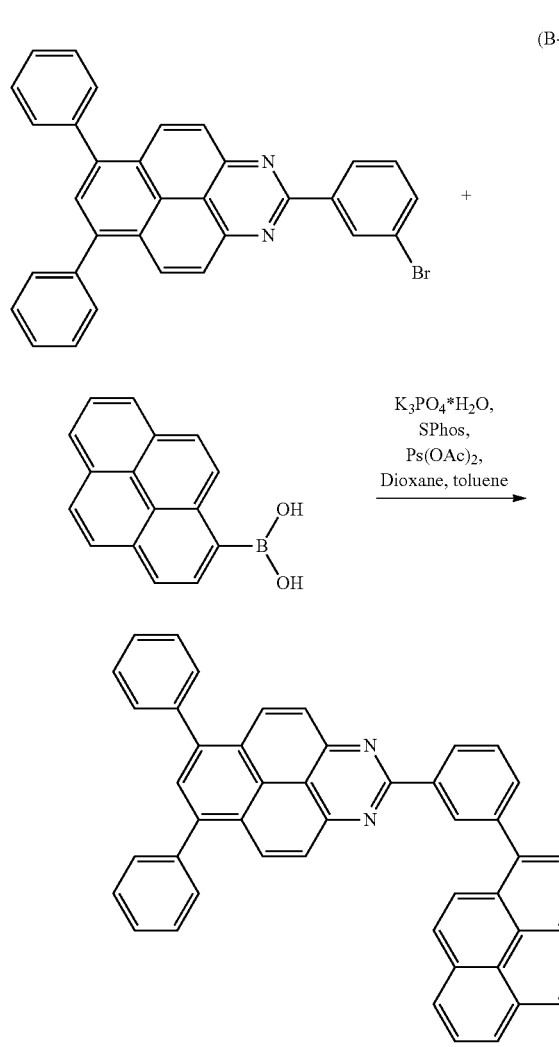

c) 2.00 g (39.1 mmol) of the product of example 6b, 1.15 g (4.69 mmol) 1-pyrenboronic acid, and 2.84 g (11.7 mmol) potassium phosphate tribasic monohydrate are degassed with argon. 10 ml 1,4-dioxane, 40 ml toluene and 8 ml water are added. The reaction mixture is degassed with argon. 96 mg (0.24 mmol) 2-dicyclohexylphosphino-2',6'-dimethoxybiphenyl (Sphos) and 8.8 mg (0.039 mmol) palladium (II) acetate are added and the reaction mixture is heated under argon for 4 h. The solvent is distilled off, the product is filtered off and washed with water and ethanol. Column chromatography on silica gel with toluene/cyclohexane 7/3 results in the product, which is decocted with diethyl ether (yield: 820 mg (33%)). Melting point: 240° C.

Example 7

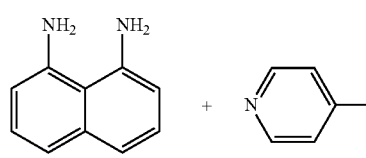

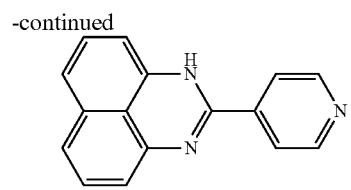

a) 50 ml ethanol are added to 5.00 g (31.6 mmol) naphthalene-1,8-diamine, 3.72 g (34.8 mmol) pyridine-4-carbaldehyde and 6.61 g (34.8 mmol) sodium disulfite. The reaction mixture is refluxed for 17 h under nitrogen and filtered hot. The solids are washed with ethanol. The ethanol phase is collected. The ethanol is partly distilled off and the ethanol solution is poured into water. The product is filtered off, washed with water and is used without purification in the next reaction step (yield: 7.33 g (95%)).

(B-39)

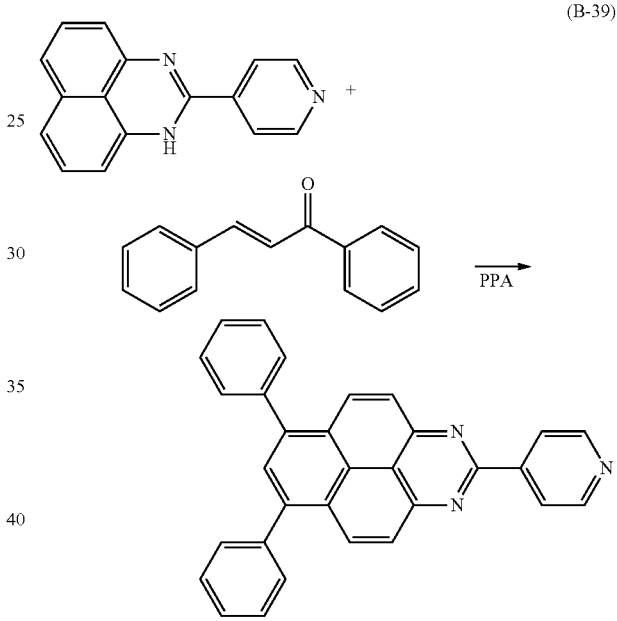

b) 5 g (20.4 mmol) of the product of example 8a, 4.67 g (22.4 mmol) (E)-1,3-diphenyl-propenone are added to a mixture of 50 g polyphosphoric acid and 3 ml toluene. The reaction mixture is heated to 100° C. for 26 h under nitrogen and is poured into water. The water phase is neutralized with an aqueous ammonia solution. The product is filtered off and is washed with water, ethanol and again water. Column chromatography on silica gel with toluene/ethyl acetate result in the product, which is soxhlet extracted with diethylether (yield: 2.00 g (23%)). Melting point 280-284° C.

Example 8

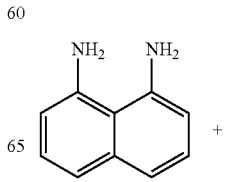

Example 9

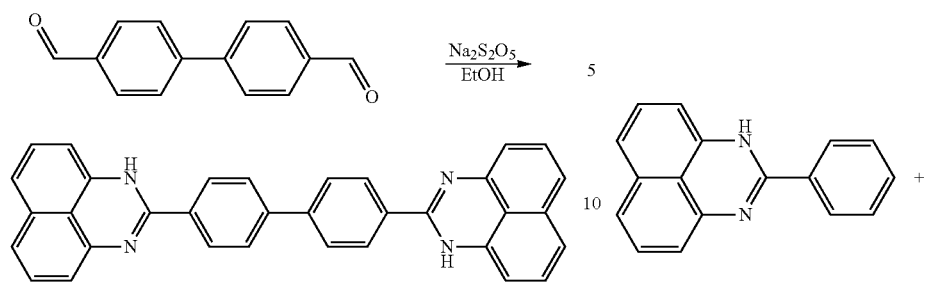

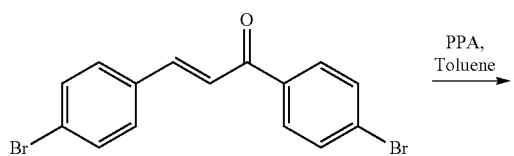

a) A mixture of 5.00 g (31.6 mmol) naphthalene-1,8-diamine, 24.0 g (126 mmol) sodium disulfite and 2.99 g (14.2 mmol) biphenyl-4,4'-dicarbaldehyde in 80 ml ethanol is refluxed for 22 h under nitrogen. The reaction mixture is cooled to 25° C., the product is filtered off, washed with water and ethanol and is used without further purification in the next reaction step (yield: 6.90 g (100%)).

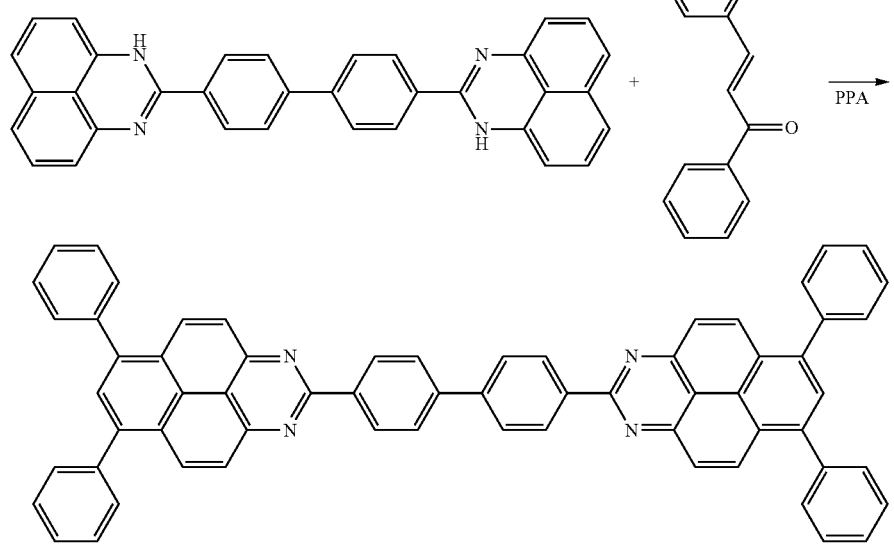

(C-7)

b) 1.50 g (3.08 mmol) of the product of example 9a, 2.89 g (13.9 mmol) (E)-1,3-diphenyl-propenone are added to a mixture of 20 g polyphosphoric acid and 5 ml toluene. The reaction mixture is heated to 100° C. for 94 h under nitrogen and is poured into water. The water phase is neutralized with an aqueous ammonia solution. The product is filtered off, is washed with water, ethanol and again water and is decocted with butan-2-one. Column chromatography on silica gel with toluene/ethyl acetate 100/1 results in the product (yield: 230 mg (9%)).

$^1$H NMR (300 MHz, CDCl$_3$): δ=8.94 (d, J=8.4 Hz, 4H), 8.66 (d, J=9.4 Hz, 4H), 8.31 (d, J=9.4 Hz, 4H), 8.08 (s, 2H), 7.92 (d, 8.5 Hz, 4H), 7.48-7.65 ppm (m, 20H).

-continued

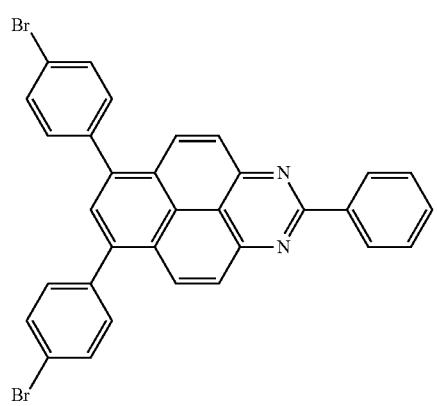

a) 3.50 g (14.3 mmol) of the product of example 3a and 6.29 g (17.2 mmol) (E)-1,3-diphenyl-propenone are added to a mixture of 35 g polyphosphoric acid and 5 ml toluene. The reaction mixture is heated at 100° C. for 45 h under nitrogen and is poured into water. The water phase is neutralized with an aqueous ammonia solution. The product is filtered off, is washed with water, ethanol and again water and is soxhlet extracted with chloroform. Diethylether is added to the chloroform layer and the product is filtered off (yield: 2.75 g (33%)).

filtered off and is washed with toluene, ethanol, water and again ethanol (yield: 2.65 g (90%)).

$^1$H NMR (300 MHz, CDCl$_3$): δ=8.84 (d, J=6.7 Hz, 2H), 8.78 (d, J=9.4 Hz, 2H), 8.27 (d, J=0.3 Hz, 2H), 8.12 (s, 1H), 8.07 (d, J=8.4 Hz, 2H), 7.96 (d, J=7.9 Hz, 2H), 7.86 (d, J=8.1 Hz, 2H), 7.44-7.68 (m, 15H), 6.90-7.37 ppm (m, 16H).

Example 10

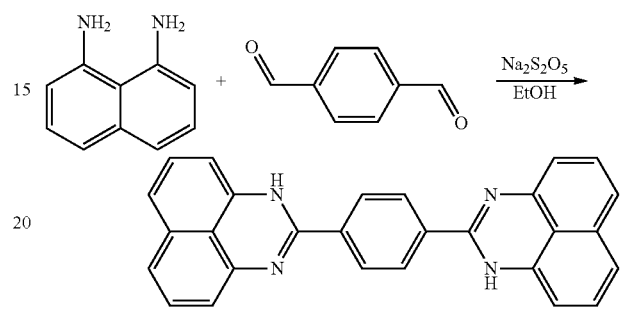

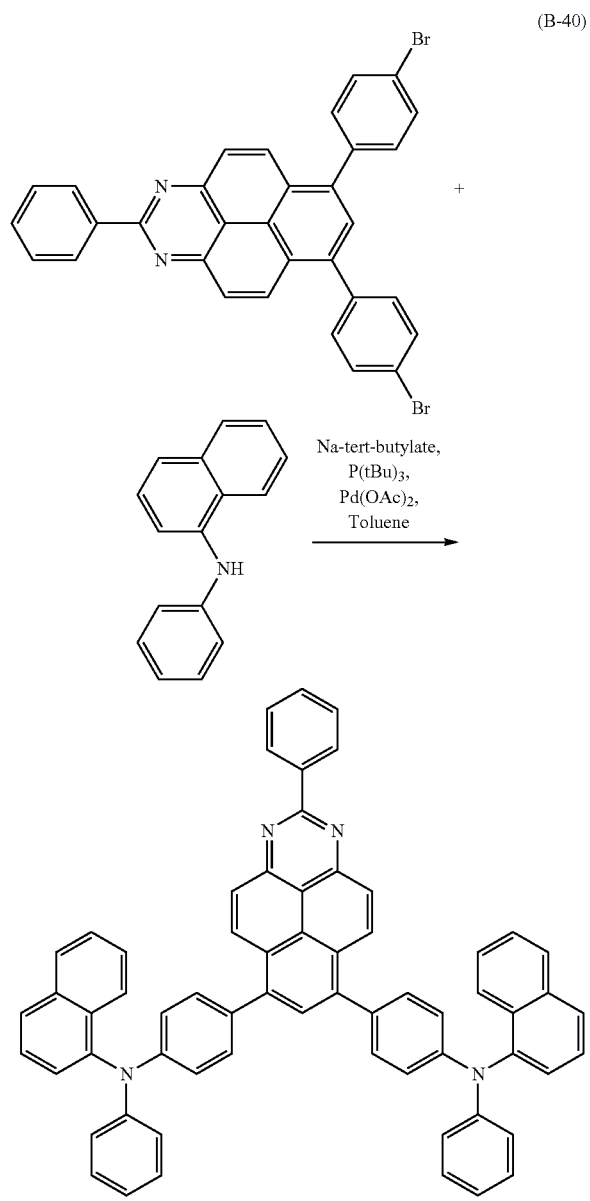

a) A mixture of 10.0 g (63.2 mmol) naphthalene-1,8-diamine, 361 g (190 mmol) sodium disulfite and 3.82 g (28.5 mmol) benzene-1,4-dicarbaldehyde in 120 ml ethanol is refluxed for 22 h under nitrogen. The reaction mixture is cooled to 25° C., the product is filtered off, washed with ethanol, water and ethanol. Soxhlet extraction with ethanol results in the product (yield 6.90 g (100%)).

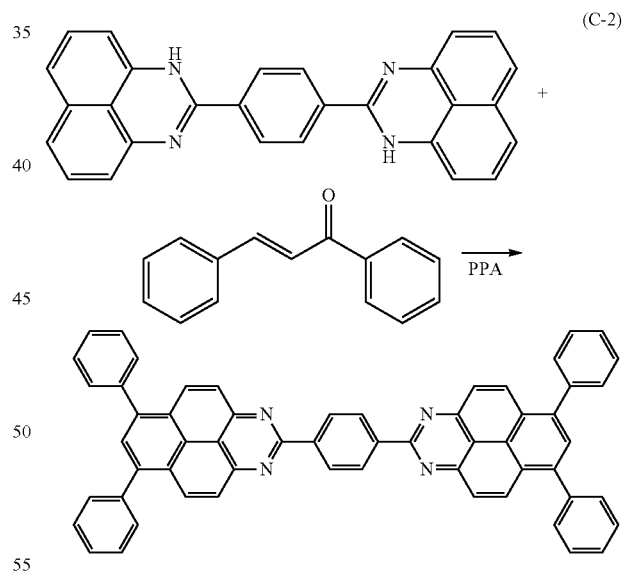

b) 2.00 g (3.39 mmol) of the product of example 9a, 1.63 g (7.45 mmol) naphthalene-1-yl-phenyl-amine and 980 mg (10.2 mmol) sodium tert-butylate are dissolved in 50 ml toluene. The reaction mixture is degassed with argon. 38 mg (0.17 mmol) palladium (II) acetate is added. The reaction mixture is degassed with argon. 69 mg (0.34 mmol) tri-tert-butyl-phosphene are added. The reaction mixture is degassed with argon and is stirred for 28 h at 100° C. under argon. The product is b) 5.70 g (13.9 mmol) of the product of example 9a and 13.0 g (62.5 mmol) (E)-1,3-diphenyl-propenone are added to a mixture of 60 g polyphosphoric acid and 5 ml toluene. The reaction mixture is heated at 100° C. for 47 h under nitrogen and is poured into water. The product is filtered off and is washed with water and ethanol. A suspension of the product in water is neutralized with an aqueous ammonia solution. The product is filtered off, washed with water, ethanol and again water and decocted with butan-2-one. Column chromatography on silica gel with toluene/ethyl acetate 100/1 results in the product (yield: 230 mg (8%)).

¹H NMR (300 MHz, CDCl₃): δ=9.10 (s, 4H), 8.72 (d, 2H, J=9.5 Hz, 4H), 8.34 (d, J=9.5 Hz, 4H), 8.15 (s, 2H), 7.53-7.78 ppm (m, 24H).

Example 11

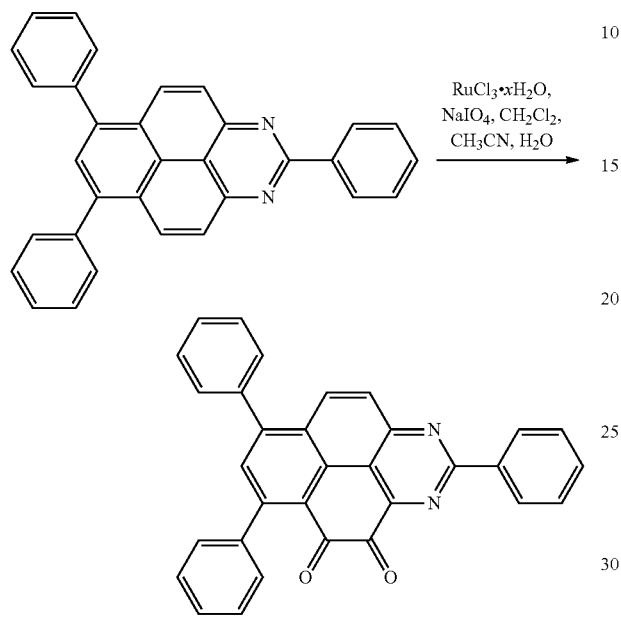

(G-4)

a) A mixture of 5.00 g (11.6 mmol) of the product of example 3b, 550 mg (2.66 mmol) ruthenium(III)-chloride hydrate (~41% Ru), 20.3 g (94.9 mmol) sodium periodate in 50 ml dichloromethane, 50 ml acetonitrile and 60 ml water is stirred at 60° C. for 15 h under nitrogen. The reaction mixture is poured into water. The product is filtered off, washed with water and ethanol, filtered on Hyflo with chloroform and is used without further purification in the next reaction step (yield 2.70 g (48%)).

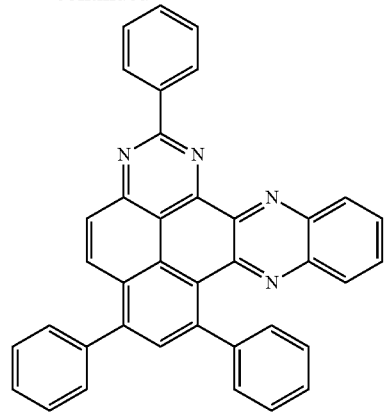

b) 2.70 g (5.48 mmol) of the product of example 11a and 1.42 g (13.2 mmol) benzene-1,2-diamine are dissolved in 15 ml chloroform and 30 ml ethanol. 5 drops of sulphuric acid (97%) are added. The reaction mixture is refluxed for 16 h and cooled to 25° C. The product is filtered off, washed with ethanol, water and again ethanol. Column chromatography on silica gel with dichloromethane leads to the product in 10% yield.

¹H NMR (300 MHz, CDCl₃): δ=8.63-8.67 (m, 2H), 8.42 (d, J=9.4 Hz, 1H), 8.05 (d, J=9.4 Hz, 1H), 7.77 (s, 1H), 7.42-7.60 ppm (m, 17H).

Example 12

(K-1)

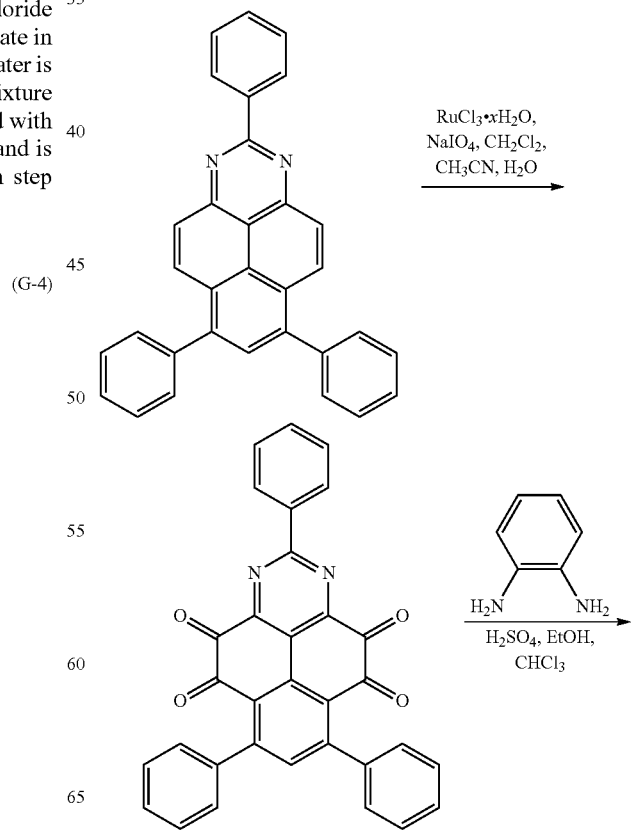

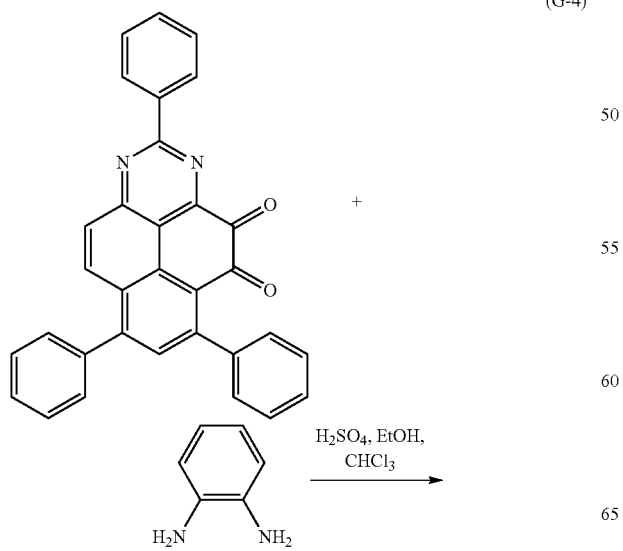

-continued

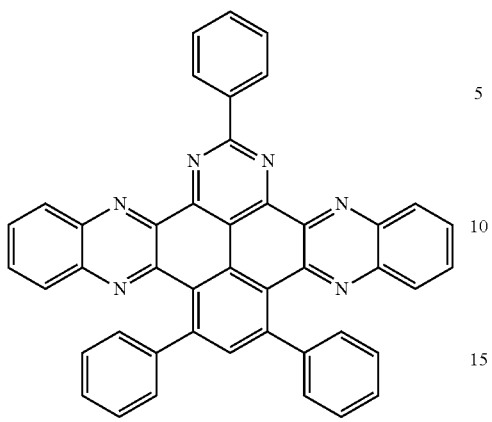

Example 11 is repeated, except that more oxidation agent and a longer reaction time are used in the first reaction step.

$^1$H NMR (300 MHz, CDCl$_3$): δ=9.13 (d, J=6.9 Hz, 2), 8.53 (d, J=8.4 Hz, 2H), 8.03 (s, 1H), 7.84 (dd, J=8.4 Hz, J=1.4 Hz, 2H), 7.76 (dd, J=8.4 Hz, J=1.3 Hz, 2H), 7.72-7.43 (m, 13H), 7.35 ppm (d, J=8.6 Hz, 2H).

Example 13

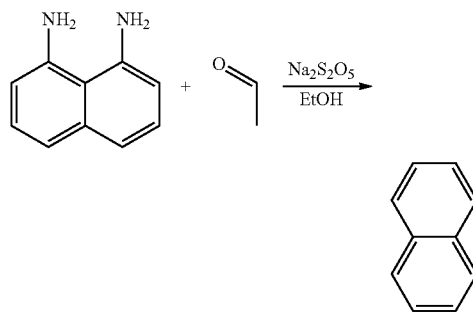

a) 100 ml ethanol are added to 10.0 g (63.2 mmol) naphthalene-1,8-diamine, 3.34 g (75.9 mmol) acetaldehyde and 24.0 g (126 mmol) sodium disulfite. The reaction mixture is stirred for 4 h at 40° C. (oil bath) under nitrogen and is poured into water. The water phase is extracted with dichloromethane. The organic phase is dried with magnesium sulphate and the solvent is removed in vacuum (yield: 6.55 g (57%)).

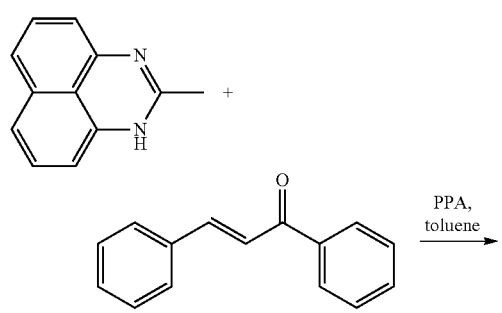

-continued

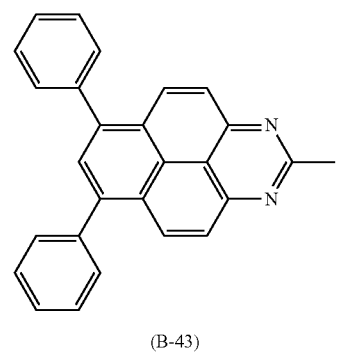

(B-43)

b) 4.00 g (22.0 mmol) of the product of example 13a, 5.03 g (24.2 mmol) (E)-1,3-diphenyl-propenone are added to a mixture of 40 g polyphosphoric acid (PPA) and 3 ml toluene. The reaction mixture is heated to 100° C. for 31 h under nitrogen and is poured into water. The product is filtered off and is washed with water, ethanol and again water. A suspension of the product in water is neutralized with an aqueous ammonia solution. The product is filtered off and is washed with ethanol (yield: 2.12 g (26%)).

$^1$H NMR (300 MHz, CDCl$_3$): δ=8.70 (d, J=9.4 Hz, 2H), 8.18 (d, J=9.4 Hz, 2H), 8.15 (s, 1H), 7.52-7.71 (m, 10H), 3.20 (s, 3H).

Example 14

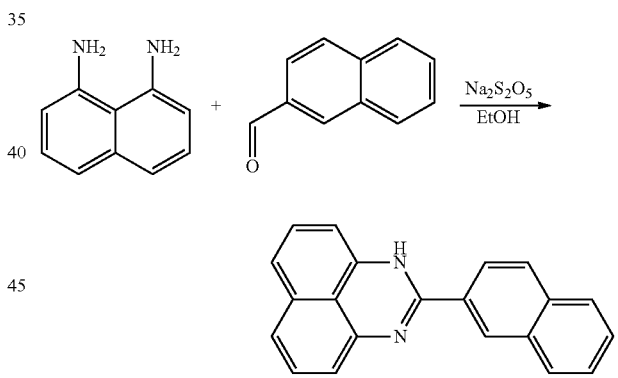

a) 100 ml ethanol are added to 7.00 g (44.3 mmol) naphthalene-1,8-diamine, 7.60 g (48.7 mmol) naphthalene-2-carbaldehyde and 9.25 g (48.7 mmol) sodium disulfite. The reaction is refluxed for 17 h under nitrogen. The product is filtered off and is washed with ethanol and water (yield: 7.27 g (56%)). The product is used without purification in the next reaction step.

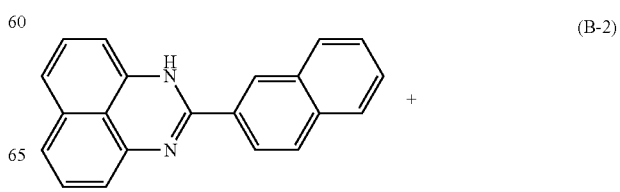

(B-2)

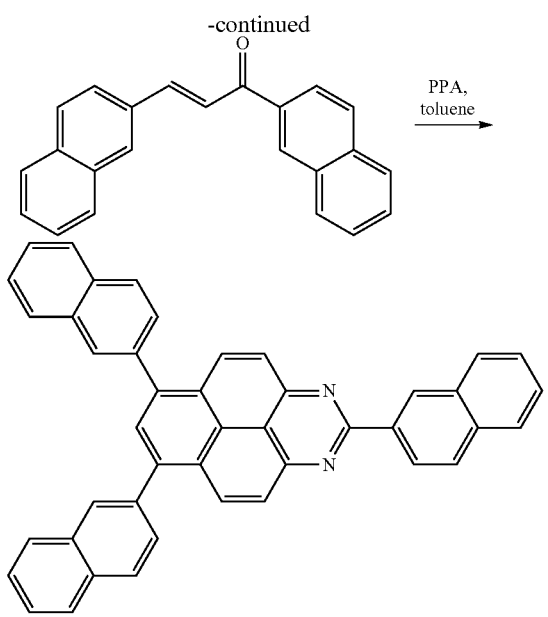

b) 5 g (17.0 mmol) of the product of example 14a, 6.29 g (20.4 mmol) (E)-1,3-di-naphthalen-2-yl-propenone are added to a mixture of 50 g polyphosphoric acid and 2 ml toluene. The reaction mixture is heated to 100° C. for 28 h under nitrogen and is poured into water. The water phase is neutralized with an aqueous ammonia solution. The product is filtered off and is washed with water, ethanol and again water. Soxhlet extraction with ethyl acetate and water with toluene gives the product, which is decocted with ethyl acetate (yield: 2.16 g (22%)). Melting point: 267-270° C.

Example 15

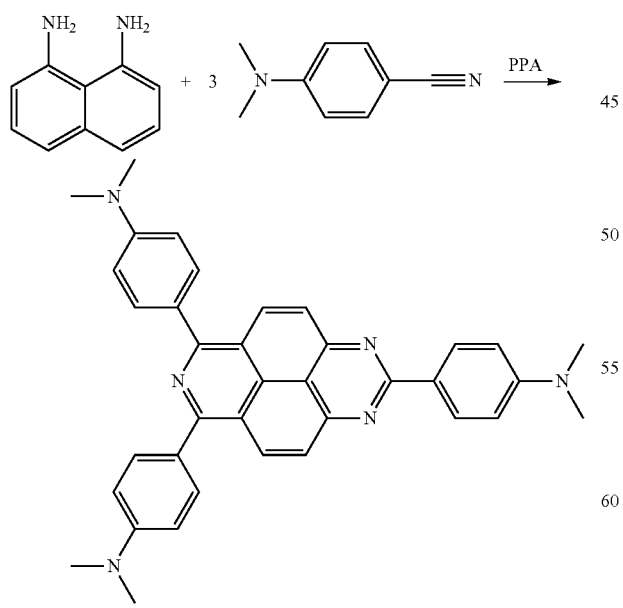

2.94 g (18 mmol) naphthalene-1.8-diamine and 9.40 g (63 mmol) 4-(dimethylamino)-benzonitrile are stirred into 100 g of polyphosphoric acid containing 83% of phosphorus pentoxide. The reaction mixture is heated up to 180° C. and is kept at this temperature for 3 hours. After cooling down to 90° C., the reaction mass in poured into 2.5 l of an ice/water mixture and is intensely stirred for 3 hours. The precipitate is filtered off and slurried up in 200 ml of water, the suspension is neutralized to pH 7 with diluted aqueous sodium hydroxide, stirred for 2 hours and filtered. The presscake is dried at 50° C. during 15 hours at reduced pressure. The well grinded powder is soxhlet extracted with 150 ml of ethyl acetate during 5 hours. The extract is concentrated to a volume of 60 ml on a rotavapor at slightly reduced pressure and left at room temperature for 18 hours. The product is isolated by filtration, dissolved again in 300 ml of boiling ethyl acetate, concentrated to a volume of 30 ml at slightly reduced pressure on a rotavapor and left at room temperature for 24 hours. The final product is isolated by filtration (yield: 0.39 g (4%)).

| Elemental composition: | 76.28% C | 5.95% H | 13.50% N |
| Calculated for $C_{37}H_{34}N_6 \times H_2O$: | 76.53% C | 6.25% H | 14.47% N |
| Calculated for $C_{37}H_{34}N_6$: | 78.98% C | 6.09% H | 14.93% N |

Example 16

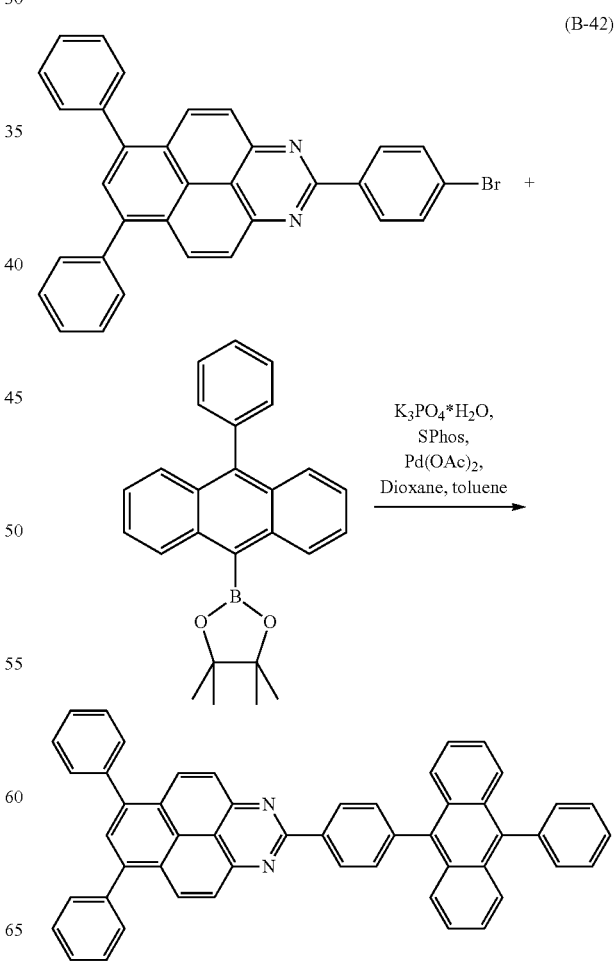

3.00 g (5.87 mmol) of the product of example 2b, 2.12 g (5.57 mmol) 4,4,5,5-tetramethyl-2-(10-phenyl-anthracen-9-yl)-1,3,2-dioxaborolane and 2.84 g (11.7 mmol) potassium phosphate tribasic monohydrate are degassed with argon. 200 ml 1,4-dioxane, 50 ml toluene and 10 ml water are added. The reaction mixture is degassed with argon. 145 mg (0.35 mmol) 2-dicyclohexylphosphino-2',6'-dimethoxybiphenyl (Sphos) and 13 mg (0.059 mmol) palladium(II)acetate are added. The reaction mixture is degassed with argon and heated under argon at 100° C. for 4 h. Work up is carried out in analogy to example 6c (yield: 1.47 g; (17%)).

$^1$H NMR (300 MHz, CDCl$_3$): δ=9.06 (d, J=8.3 Hz, 2H), 8.76 (d, J=9.4 Hz, 2H), 8.37 (d, J=9.4 Hz, 2H), 8.19 (s, 1H), 7.52-7.90 (m, 21H), 7.34-7.40 (m, 4H).

Example 17

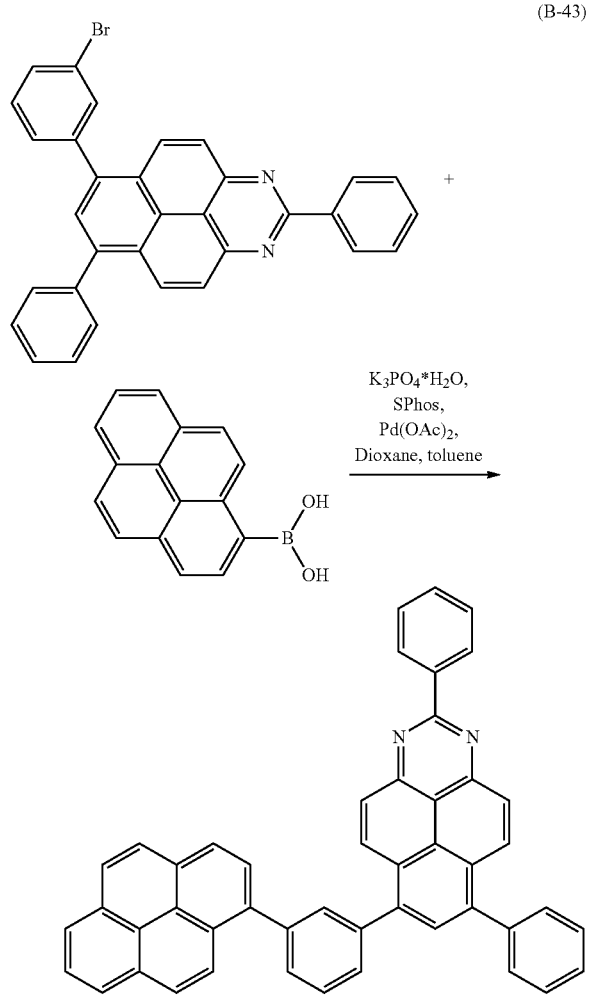

The product is prepared in analogy to example 6c.

$^1$H NMR (300 MHz, CDCl$_3$, δ): 8.92 (d, J=9.4 Hz, 2H), 8.87 (d, J=8.4 Hz, 2H), 7.71 (d, J=9.4 Hz, 2H), 7.48-7.40 (m, 22H).

Application Example 1

Devices are fabricated by thermal evaporation in high vacuum (<10$^{-6}$ mbar). The anode consists of ca. 120 nm of indium tin oxide (ITO) previously deposited on a glass substrate. The cathode consists of 1 nm of LiF followed by 100 nm of Al. All devices are tested immediately after preparation, without encapsulation, in the nitrogen atmosphere of a glove box (<1 ppm of H$_2$O and O$_2$).

The organic stack consists sequentially, from the ITO surface, of 60 nm of 2-TNATA (4,4",4"'-tris(N-(naphtha-2-yl)-N-phenyl-amino)triphenylamine) as the hole injection layer (HIL), 30 nm of 4,4'-bis[N-(1-naphtyl)-N-phenylamino]biphenyl (α-NPD) as the hole transport layer, 30 nm of a aluminum(III) bis(2-methyl-8-hydroxyquinolinato)-4-phenylphenolate (BalQ) doped with 10% of red emitter, bis(1-phenylisoquinoline) (acetylacetonate)iridium(III), as the emissive layer. The composition of the electron transport layer (ETL) is shown in the table below.

The luminous efficiency, along with the onset voltage (@1000 cd/m$^2$) and maximum luminance measured for devices 1-1, 1-2 and 1-3 is reported in the table below:

| ETL | C. Eff@1000 cd/m$^2$ | P. Eff@1000 cd/m2 | V@1000 cd/m$^2$ | Max Lum/ cd/m$^2$ |
|---|---|---|---|---|
| 1-1 Cpd. of Ex. 1 (10 nm)/AlQ$_3$ (30 nm) | 5.4 | 1.6 | 10.4 | 8200 |
| 1-2 TPBI (10 nm)/Cpd. of Ex. 1 (30 nm) | 6.3 | 1.5 | 13.4 | 1100 |
| 1-3 Cpd. of Ex. 6 (30 nm) | 7.6 | 2.3 | 10.3 | 6000 |

TPBI = 1,3,5-tris(N-phenylbenzimidazol-2-yl)benzene

Application Example 2

Devices 2-1 and 2-2 are fabricated the same way as in application example 1, except that the compound of Ex. 2 is used as a host instead of Balq and the composition of the electron transport layer, which is shown in the table below, is different.

The luminous efficiency, along with the onset voltage (@1000 cd/m$^2$) and maximum luminance measured for devices 2-1 and 2-2 is reported in the table below:

| ETL | C. Eff@1000 cd/m$^2$ | P. Eff@1000 cd/m2 | V@1000 cd/m$^2$ | Max Lum/cd/m$^2$ |
|---|---|---|---|---|
| 2-1 BalQ (10 nm)/ AlQ$_3$ (30 nm) | 2.5 | 0.6 | 13 | 1300 |
| 2-2 AlQ$_3$ (30 nm) | 1.8 | 0.5 | 10.9 | 1600 |

Application Example 3

Device 3-1 is fabricated the same way as device 1-2, except that the compound of Ex.1 is used as a host instead of Balq and the composition of the electron transport layer, which is shown in the table below, is different.

The luminous efficiency, along with the onset voltage (@1000 cd/m$^2$) and maximum luminance measured for device 3-1 is reported in the table below.

| ETL (nm) | C. Eff@1000 cd/m$^2$ | P. Eff@1000 cd/m2 | V@1000 cd/m$^2$ | Max Lum/cd/m$^2$ |
|---|---|---|---|---|
| 3-1 TPBI (10 nm)/ AlQ$_3$ (30 nm) | 2.7 | 0.8 | 10.3 | 4000 |

Application Example 4

A device is fabricated by thermal evaporation in high vacuum (<10⁻⁶ mbar). The anode consists of ca. 120 nm of indium tin oxide (ITO) previously deposited on a glass substrate. The cathode consists of 1 nm of LiF followed by 100 nm of Al.

The organic stack consists sequentially, from the ITO surface, α-NPD doped with $MoO_x$ (60 nm) as hole injection/hole transporting layer, α-NPD (10 nm) as electron-blocking layer, α-NPD doped with 10% of red emitter, bis(1-phenyl-isoquinoline) (acetylacetonate)iridium(III), as the emissive layer (20 nm). The composition of the electron transport layer (ETL), the luminous efficiency, along with the onset voltage (@1000 cd/m²) and maximum luminance measured for device 4-1 are reported in the table below.

| ETL | C. Eff@1000 cd/m² | P. Eff@1000 cd/m² | V@1000 cd/m² | Max Lum/cd/m² |
|---|---|---|---|---|
| 4-1 Cpd. of Ex. 6 (30 nm) | 6.7 | 2.4 | 8.6 | 2700 |

(NHT5 and NDP2 were provided by Novaled AG, Dresden)

Application Example 5

Device 5-1 is fabricated in the same way as device 4-1, except that the cathode consists of 100 nm of Al and the compound of Ex. 2 is used as host instead of α-NPD. The composition of the electron transport layer (ETL), the luminous efficiency, along with the onset voltage (@1000 cd/m²) and maximum luminance measured for device 5-1 are reported in the table below.

| ETL | C. Eff@1000 cd/m² | P. Eff@1000 cd/m² | V@1000 cd/m² | Max Lum/cd/m² |
|---|---|---|---|---|
| 5-1 BalQ (10 nm)/BCP doped with CsCO₃ (60 nm) | 2.6 | 2 | 4.1 | 1900 |

Application Example 6

Devices 6-1 and 6-2 are fabricated in the same way as device 5-1, except that iridium(III)bis-(2-methyldibenzo[th] quinoxaline) (acetylacetonate) is used as an emitter and α-NPD as host. The composition of the electron transport layer (ETL), the luminous efficiency, along with the onset voltage (@1000 cd/m²) and maximum luminance measured for devices 6-1 and 6-2 are reported in the table below.

| ETL | C. Eff@1000 cd/m² | P. Eff@1000 cd/m² | V@1000 cd/m² | Max Lum/cd/m² |
|---|---|---|---|---|
| 6-1 BalQ (10 nm)/cpd. of Ex. 1 doped with CsCO₃ (60 nm) | 1.2 | 0.6 | 6.3 | 1800 |
| 6-2 BalQ (10 nm)/cpd. of Ex. 6 doped with CsCO₃ (60 nm) | 1.2 | 0.5 | 6.8 | 1500 |

Application Example 7

Devices 7-1, 7-2 and 7-3 are fabricated in the same way as device 1-1, except that iridium(III)bis-(2-methyldibenzo[th] quinoxaline) (acetylacetonate) is used as an emitter. The composition of the electron transport layer (ETL), the luminous efficiency, along with the onset voltage (@1000 cd/m²) and maximum luminance measured for devices 7-1, 7-2 and 7-3 are reported in the table below.

| ETL | C. Eff@1000 cd/m² | P. Eff@1000 cd/m2 | V@1000 cd/m² | Max Lum/cd/m² |
|---|---|---|---|---|
| 7-1 Cpd. of Ex. 3 (30 nm) | 8 | 1.8 | 14 | 1000 |
| 7-2 Cpd. of Ex. 7 (30 nm) | 4 | 0.9 | 14 | 1000 |
| 7-3 BalQ (10 nm)/ Cpd. of Ex. 3 (30 nm) | 6.5 | 1.4 | 14 | 1000 |

Example 8

Devices 8-1, 8-2 and 8-3 are fabricated in the same way as device 4-1, except that iridium(III)bis-(2-methyldibenzo[th] quinoxaline) (acetylacetonate) is used as an emitter. The composition of the electron transport layer (ETL), the luminous efficiency, along with the onset voltage (@1000 cd/m²) and maximum luminance measured for devices 8-1, 8-2 and 8-3 are reported in the table below.

| ETL | C. Eff@1000 cd/m² | P. Eff@1000 cd/m2 | V@1000 cd/m² | Max Lum/cd/m² |
|---|---|---|---|---|
| 8-1 Cpd. of Ex. 3 (30 nm) | 10.4 | 3.9 | 8.3 | 2000 |
| 8-2 Cpd. of Ex. 7 (30 nm) | 2.8 | 1 | 9.1 | 2900 |
| 8-3 BalQ (10 nm)/ Cpd. of Ex. 3 (30 nm) | 4.4 | 1.5 | 9.2 | 3200 |

The invention claimed is:

1. An electronic device, comprising a compound of formula

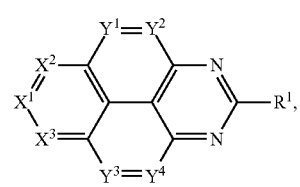

or

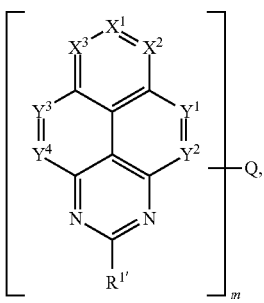

(III)

wherein $Y^1, Y^2, Y^3, Y^4, X^1, X^2$ and $X^3$ are independently each other N, or $CR^4$, with the proviso that at least one of the groups $X^1$, $X^2$ and $X^3$ is a group $CR^4$, $R^1$ is hydrogen, F, —$SiR^{100}R^{101}R^{102}$, or an organic substituent, $R^{1'}$ and $R^4$ are independently of each other hydrogen, F, —$SiR^{100}R^{101}R^{102}$, or an organic substituent, or any of the substituents $R^1$, $R^{1'}$ and $R^4$, which are adjacent to each other, together form an aromatic, or heteroaromatic ring, or ring system, which can optionally be substituted, m is an integer of 1 to 6, and $R^{100}$, $R^{101}$ and $R^{102}$ are independently of each other a $C_1$-$C_8$alkyl group, a $C_6$-$C_{24}$aryl group, or a $C_7$-$C_{12}$aralkyl group, which may optionally be substituted, and Q is a linking group; with the proviso that in the compound of formula III at least one of the substituents $R^{1'}$, or $R^4$ is a group Q.

2. An electronic device according to claim 1, comprising a compound of formula

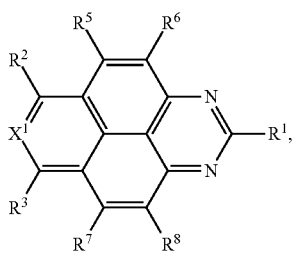

(II)

wherein $X^1$ is N, or $CR^4$, $R^1, R^2, R^3, R^4, R^5, R^6, R^7$ and $R^8$ are independently of each other H, $C_1$-$C_{18}$alkyl, $C_1$-$C_{18}$alkyl which is substituted by E and/or interrupted by D, $C_1$-$C_{18}$ perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —CO—$R^{28}$, —CN,

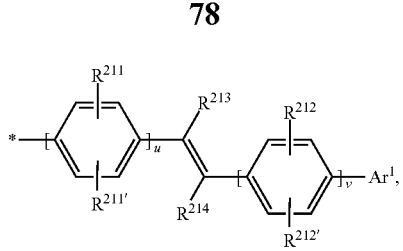

or a group -$L^1$-$NR^{25'}R^{26'}$, -wherein u is 0, or 1; v is 0, or 1;

$R^{211}, R^{211'}, R^{212}$ and $R^{212'}$ are independently of each other H, $C_1$-$C_{18}$alkyl, or $C_1$-$C_{18}$alkoxy, $R^{213}$ and $R^{214}$ are independently of each other H, or $C_1$-$C_{18}$alkyl, $Ar^1$ is —$NR^{25'}R^{26'}$, $C_6$-$C_{24}$aryl, $C_6$-$C_{24}$aryl which is substituted by G, $C_2$-$C_{20}$heteroaryl, or $C_2$-$C_{20}$heteroaryl which is substituted by G;

$R^{25'}$ and $R^{26'}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, or $R^{25'}$ and $R^{26'}$ together with the nitrogen atom to which they are bonded form a heteroaromatic ring, or ring system, which may optionally be substituted;

$L^1$ is a single bond, or a bridging unit BU, $R^5$ and $R^6$ and/or $R^7$ and $R^8$ together form a group

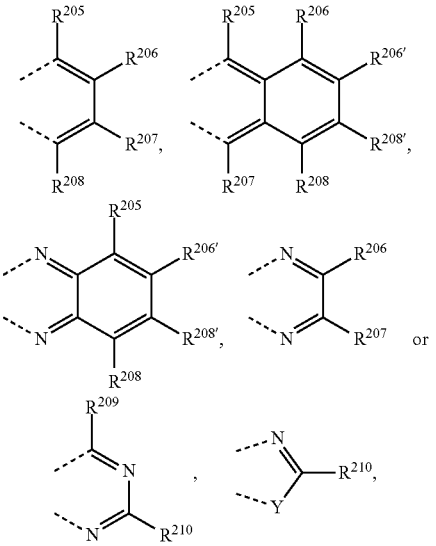

wherein $R^{206'}, R^{208'}, R^{205}, R^{206}, R^{207}$, $R^{208}, R^{209}$ and $R^{210}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $C_1$-$C_{18}$ perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_7$-$C_{25}$aralkyl, CN, or —CO—$R^{28}$, Y is O, or N—$R^{25}$, D is —CO—; —COO—; —S—; —SO—; —$SO_2$—; —O—; —$NR^{25}$—; —$SiR^{30}R^{31}$—; —$POR^{32}$—; —$CR^{23}$=$CR^{24}$—; or —C≡C—; and E is —OR²⁹; SR²⁹; —NR²⁵R²⁶; —COR²⁸; —COOR²⁷; —CONR²⁵R²⁶; —CN; or halogen;

G is E, $C_1$-$C_{18}$alkyl, $C_1$-$C_{18}$alkyl which is interrupted by D, $C_1$-$C_{18}$ perfluoroalkyl, $C_1$-$C_{18}$alkoxy, or $C_1$-$C_{18}$alkoxy which is substituted by E and/or interrupted by D, wherein R²³ and R²⁴ are independently of each other H, $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

R²⁵ and R²⁶ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; or R²⁵ and R²⁶ together form a five or six membered ring, or ring system;

R²⁷ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, R²⁸ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, R²⁹ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, R³⁰ and R³¹ are independently of each other $C_1$-$C_{18}$alkyl, $C_6$-$C_{18}$aryl, or $C_6$-$C_{18}$aryl, which is substituted by $C_1$-$C_{18}$alkyl, and R³² is $C_1$-$C_{18}$alkyl, $C_6$-$C_{18}$aryl, or $C_6$-$C_{18}$aryl, which is substituted by $C_1$-$C_{18}$alkyl.

3. An electronic device according to claim 2, comprising a compound of formula

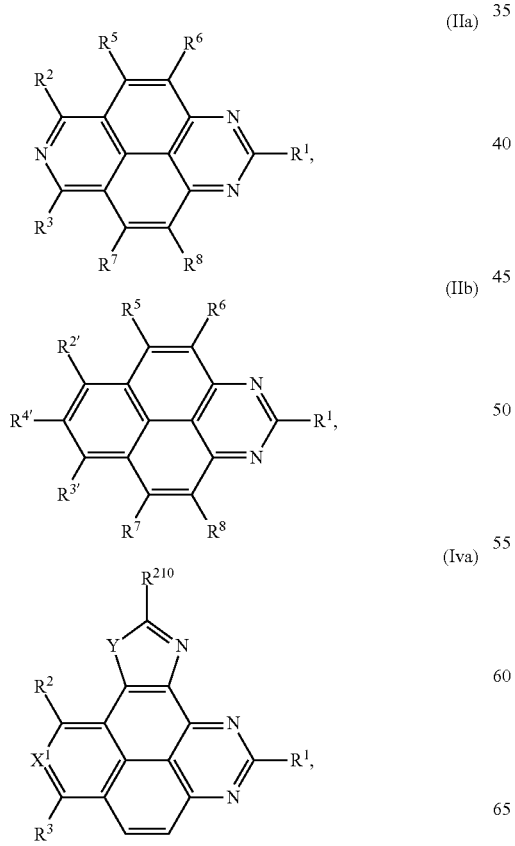

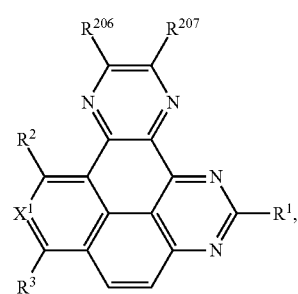

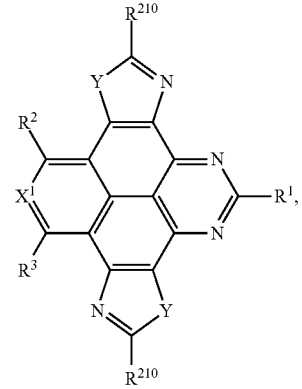

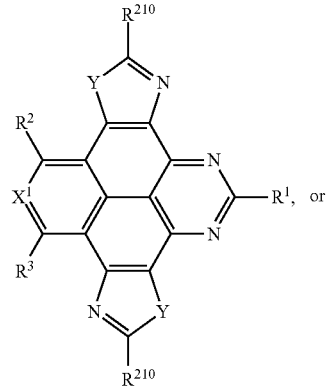

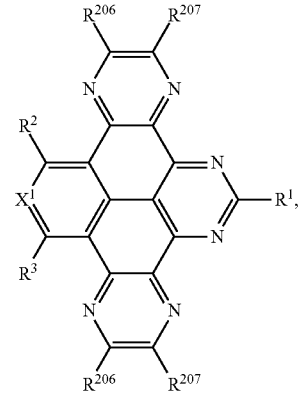

wherein
X¹ is N, or CH,
Y is O, or NR²⁵, wherein
R²⁵ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;
R²⁰⁶, R²⁰⁷, R²¹⁰ are as defined in claim 2, $R^5$, $R^6$, $R^7$ and $R^8$ are hydrogen,
$R^1$, $R^2$, $R^3$, $R^{2'}$, $R^{3'}$, and $R^{4'}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, such as
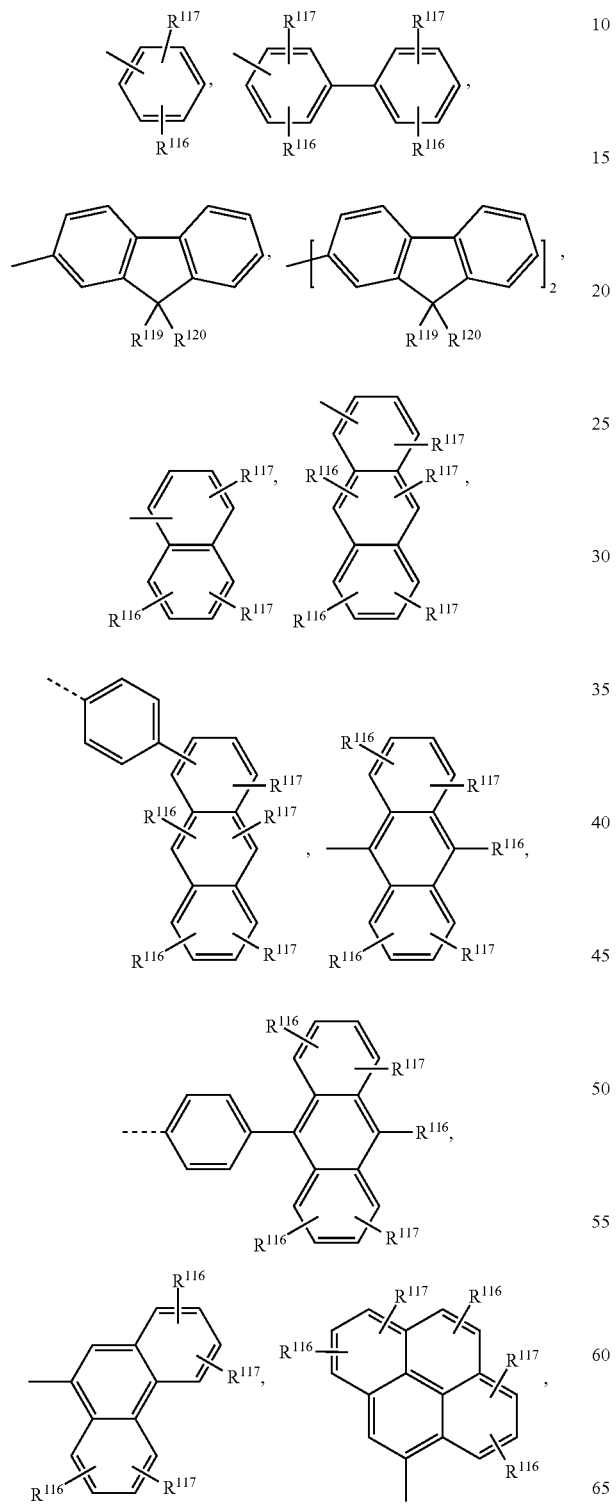
-continued
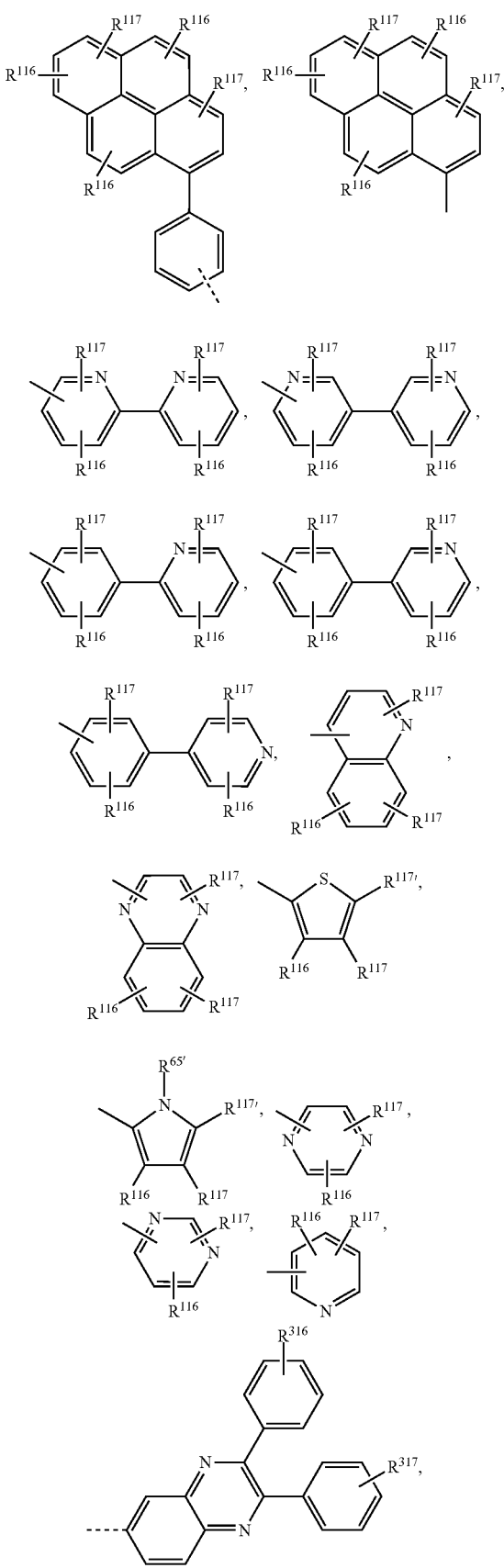

-continued

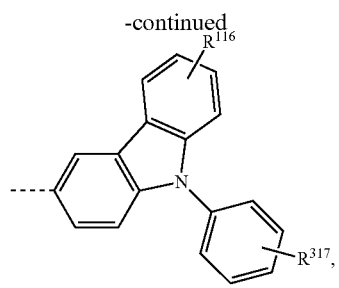

$C_1$-$C_{18}$alkoxy, $C_1$-$C_{18}$alkoxy which is substituted by E and/or interrupted by D,

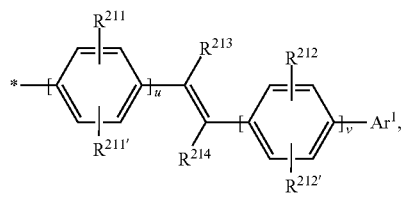

or -$L^1$-$NR^{25'}R^{26'}$, wherein
u is 0, or 1; v is 0, or 1;
$R^{211}$, $R^{211'}$, $R^{212}$ and $R^{212'}$ are independently of each other H, $C_1$-$C_{18}$alkyl, or $C_1$-$C_{18}$alkoxy,
$R^{213}$ and $R^{214}$ are independently of each other H, or $C_1$-$C_{18}$alkyl,
$Ar^1$ is —$NR^{25'}R^{26'}$, $C_6$-$C_{24}$aryl, $C_6$-$C_{24}$aryl which is substituted by G, $C_2$-$C_{20}$heteroaryl, or $C_2$-$C_{20}$heteroaryl which is substituted by G;
$L^1$ is a single bond, or a bridging unit BU, such as

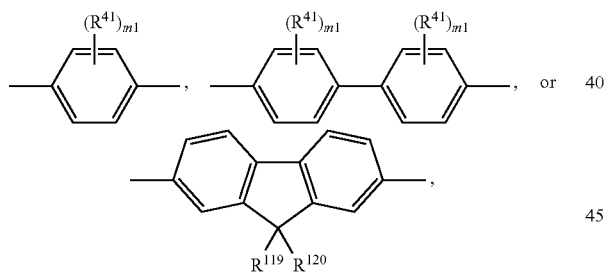

D is —O—; or —$NR^{25}$—,
E is —$OR^{29}$; —$NR^{25}R^{26}$; —CN, or F; $R^{29}$; $R^{25}$, and $R^{26}$ are as defined in claim 2;
G is E, $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D,
$R^{25'}$ and $R^{26'}$ are independently of each other phenyl, naphthyl, anthryl, biphenylyl, 2-fluorenyl, phenanthryl, or perylenyl, which can optionally be substituted, such as

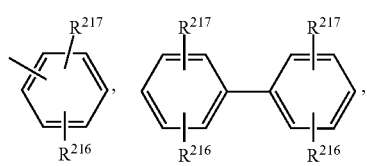

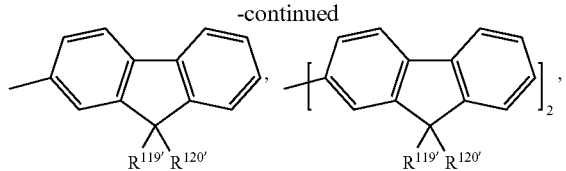

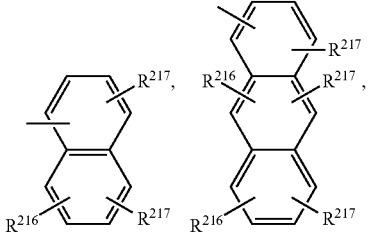

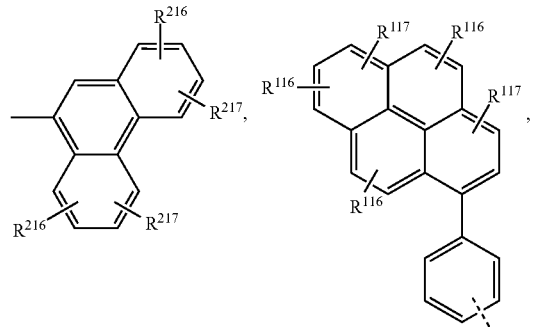

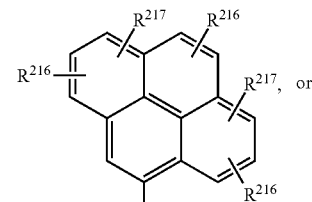

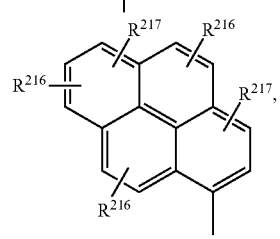

or $R^{25'}$ and $R^{26'}$ together with the nitrogen atom to which they are bonded form a heteroaromatic ring, or ring system, such as

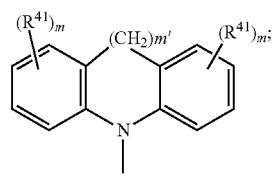

m' is 0, 1, or 2;
m can be the same or different at each occurrence and is 0, 1, 2, or 3, especially 0, 1, or 2, very especially 0 or 1;
m1 can be the same or different at each occurrence and is 0, 1, 2, 3, or 4, especially 0, 1, or 2, very especially 0 or 1,
$R^{41}$ can be the same or different at each occurrence and is Cl, F, CN, $N(R^{45})_2$, a $C_1$-$C_{25}$alkyl group, a $C_4$-$C_{18}$cycloalkyl group, a $C_1$-$C_{25}$alkoxy group, in which one or more carbon atoms which are not in neighbourhood to each other could be replaced by —$NR^{45}$—, —O—, —S—, or —C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, or two or more groups $R^{41}$ form a ring system;

$R^{45}$ is a $C_1$-$C_{25}$alkyl group, a $C_4$-$C_{18}$cycloalkyl group, in which one or more carbon atoms which are not in neighbourhood to each other could be replaced by —$NR^{45''}$—, —O—, —S—, —C(=O)—O—, or, —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, and $R^{45''}$ is a $C_1$-$C_{25}$alkyl group, or a $C_4$-$C_{18}$cycloalkyl group, $R^{216}$, $R^{217}$, $R^{116}$, $R^{117}$ and $R^{117'}$ are independently of each other H, halogen, —CN, $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', $C_2$-$C_{20}$heteroaryl, $C_2$-$C_{20}$heteroaryl which is substituted by G', $C_2$-$C_{18}$alkenyl, $C_2$-$C_{18}$alkynyl, $C_1$-$C_{18}$alkoxy, $C_1$-$C_{18}$alkoxy which is substituted by E' and/or interrupted by D', $C_7$-$C_{25}$aralkyl, —C(=O)—$R^{127}$, —C(=O)O$R^{127}$, or —C(=O)N$R^{127}R^{126}$, or substituents $R^{116}$, $R^{117}$ and $R^{117'}$, which are adjacent to each other, can form a ring, $R^{316}$ and $R^{317}$ have the meaning of $R^{116}$ and are preferably $C_1$-$C_{25}$alkyl, which may optionally be interrupted by —O—, or $C_1$-$C_{25}$alkoxy, $R^{119'}$ and $R^{120'}$ are independently of each other $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', $C_2$-$C_{20}$heteroaryl, $C_2$-$C_{20}$heteroaryl which is substituted by G', $C_2$-$C_{18}$alkenyl, $C_2$-$C_{18}$alkynyl, or $C_7$-$C_{25}$aralkyl, or $R^{119'}$ and $R^{120'}$ together form a group of formula =C$R^{121'}R^{122'}$, wherein $R^{121'}$ and $R^{122'}$ are independently of each other H, $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', or $C_2$-$C_{20}$heteroaryl, or $C_2$-$C_{20}$heteroaryl which is substituted by G', or $R^{119'}$ and $R^{120'}$ together form a five or six membered ring, which optionally can be substituted by $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', $C_2$-$C_{20}$heteroaryl, $C_2$-$C_{20}$heteroaryl which is substituted by G', $C_2$-$C_{18}$alkenyl, $C_2$-$C_{18}$alkynyl, $C_1$-$C_{18}$alkoxy, $C_1$-$C_{18}$alkoxy which is substituted by E' and/or interrupted by D', $C_7$-$C_{25}$aralkyl, or —C(=O)—$R^{127}$, and $R^{126}$ and $R^{127}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, D' is —CO—, —COO—, —S—, —SO—, —SO$_2$—, —O—, —N$R^{65}$—, —SiR$^{70}$R$^{71}$, —POR$^{72}$—, —CR$^{63}$=CR$^{64}$—, or —C≡C—, and E' is —O$R^{69}$, —S$R^{69}$, —N$R^{65}R^{66}$, —COR$^{68}$, —COOR$^{67}$, —CONR$^{65}R^{66}$, —CN, or halogen, G' is E', or $C_1$-$C_{18}$alkyl, $R^{63}$ and $R^{64}$ are independently of each other H; $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by —O—;

$R^{65}$, $R^{65'}$ and $R^{66}$ are independently of each other $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by —O—; or $R^{65}$ and $R^{66}$ together form a five or six membered ring, or $R^{65'}$ and $R^{66}$ together form a five or six membered ring, $R^{67}$ and $R^{68}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{69}$ is $C_6$-$C_{18}$aryl; $C_6$-$C_{18}$aryl, which is substituted by $C_1$-$C_{18}$alkyl, $C_1$-$C_{18}$alkoxy; $C_1$-$C_{18}$alkyl; or $C_1$-$C_{18}$alkyl which is interrupted by —O—, $R^{70}$ and $R^{71}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{72}$ is $C_1$-$C_{18}$alkyl, $C_6$-$C_{18}$aryl, or $C_6$-$C_{18}$aryl, which is substituted by $C_1$-$C_{18}$alkyl.

4. An electronic device according to claim 3, comprising a compound of formula IIa, wherein $R^5$, $R^6$, $R^7$ and $R^8$ are hydrogen, $R^1$, $R^2$, and $R^3$ are independently of each other a group

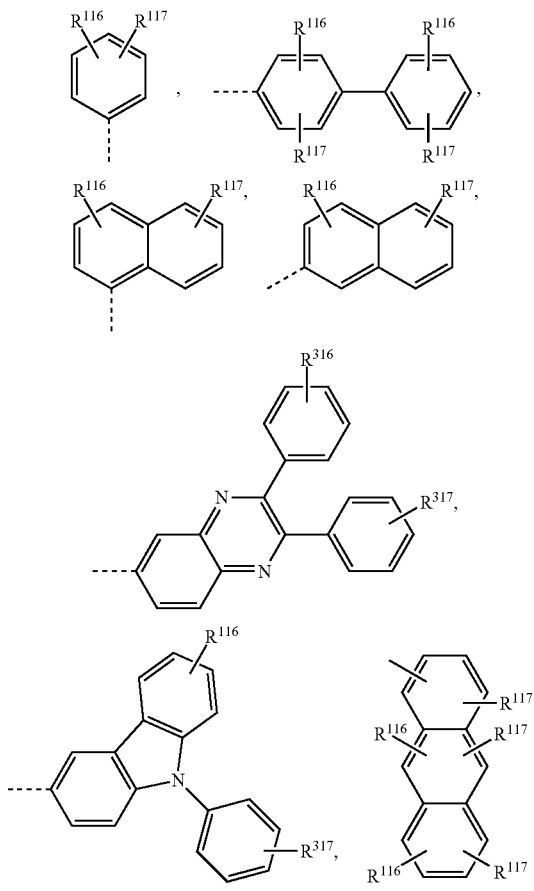

-continued

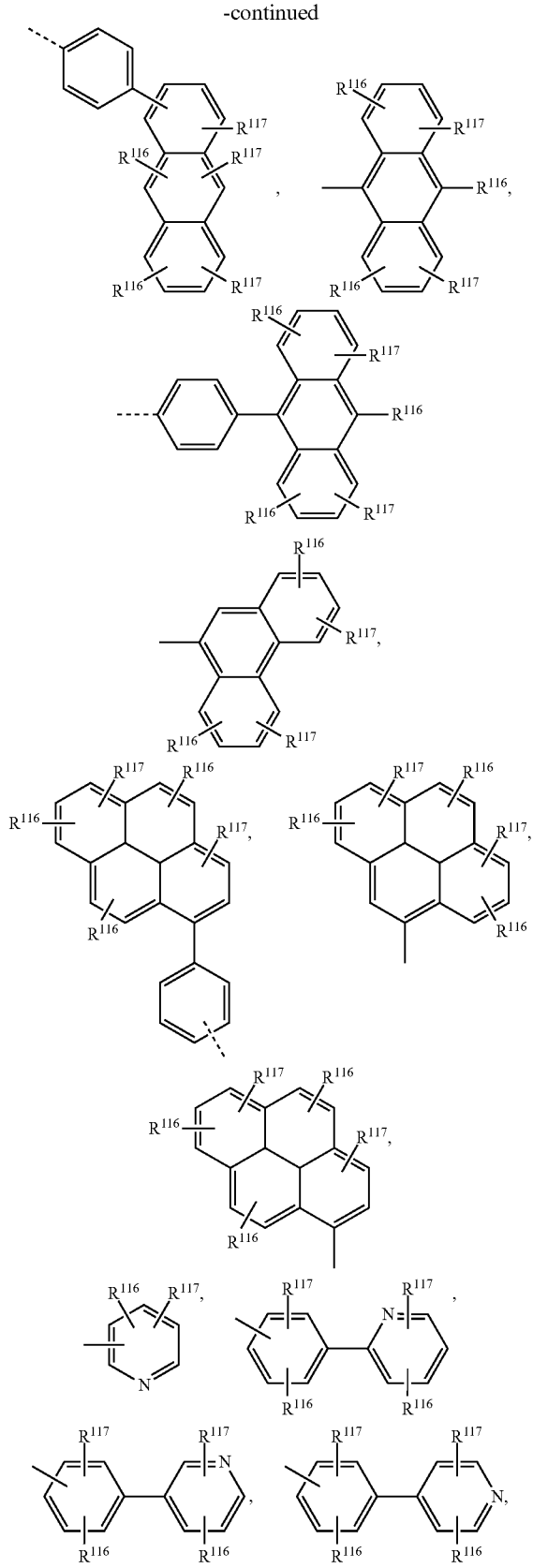

$C_1$-$C_{18}$alkoxy, $C_1$-$C_{18}$alkoxy which is substituted by E and/or interrupted by D,

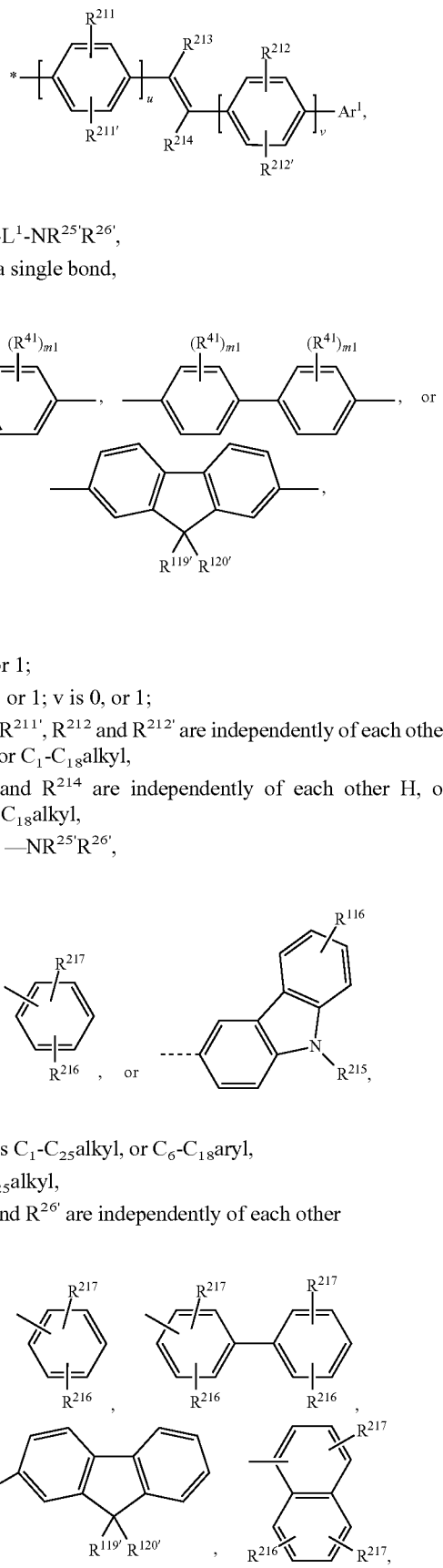

or -$L^1$-$NR^{25'}R^{26'}$, $L^1$ is a single bond, $m^1$ is 0, or 1;

u is 0, or 1; v is 0, or 1;

$R^{211}$, $R^{211'}$, $R^{212}$ and $R^{212'}$ are independently of each other H, or $C_1$-$C_{18}$alkyl, $R^{213}$ and $R^{214}$ are independently of each other H, or $C_1$-$C_{18}$alkyl, $Ar^1$ is —$NR^{25'}R^{26'}$, $R^{215}$ is $C_1$-$C_{25}$alkyl, or $C_6$-$C_{18}$aryl, $C_1$-$C_{25}$alkyl, $R^{25'}$ and $R^{26'}$ are independently of each other -continued

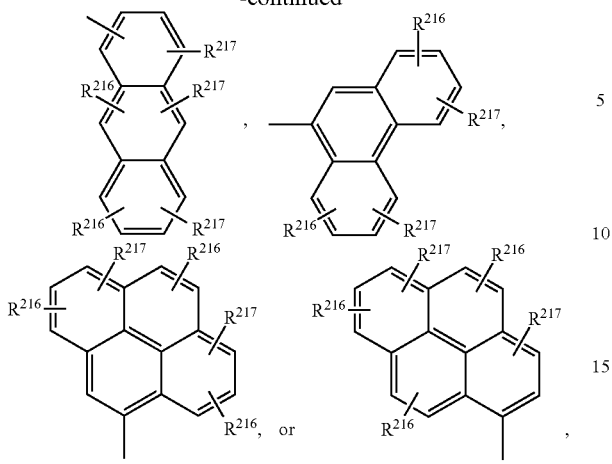

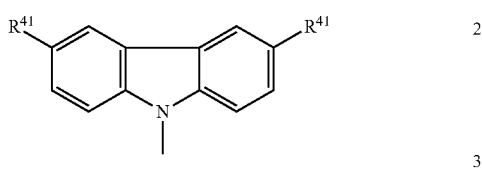

or R²⁵' and R²⁶' together with the nitrogen atom to which they are bonded form a group

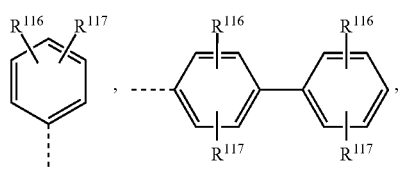

wherein

R⁴¹ is H, or $C_1$-$C_8$alkyl, and

R¹¹⁶ and R¹¹⁷ are independently of each other $C_1$-$C_{25}$alkyl, which may optionally be interrupted by —O—, or $C_1$-$C_{25}$alkoxy, 1-naphthyl, 2-naphthyl, phenyl, or pyridine, which may optionally be substituted by $C_1$-$C_{25}$alkyl, which may optionally be interrupted by —O—, or phenyl;

R¹¹⁹' and R¹²⁰' are independently of each other $C_1$-$C_{25}$alkyl, or $C_1$-$C_{25}$alkyl, which is substituted by E and/or interrupted by D, R²¹⁶ and R²¹⁷ are independently of each other $C_1$-$C_{25}$alkyl, which may optionally be interrupted by —O—, or $C_1$-$C_{25}$alkoxy, R³¹⁶ and R³¹⁷ have the meaning of R¹¹⁶ and are preferably $C_1$-$C_{25}$alkyl, which may optionally be interrupted by —O—, or $C_1$-$C_{25}$alkoxy, D is —O—; or —NR²⁵—, E is —OR²⁹; —NR²⁵R²⁶; —CN, or F; R²⁹; R²⁵, and R²⁶ are as defined in claim 2.

5. An electronic device according to claim 3, comprising a compound of formula IIb, wherein R⁵, R⁶, R⁷ and R⁸ are hydrogen, R¹, R²', and R³' are independently of each other a group, -continued

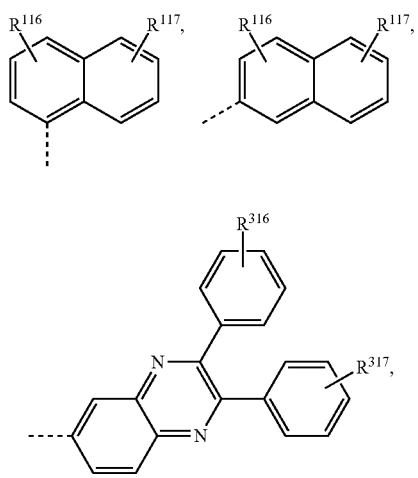

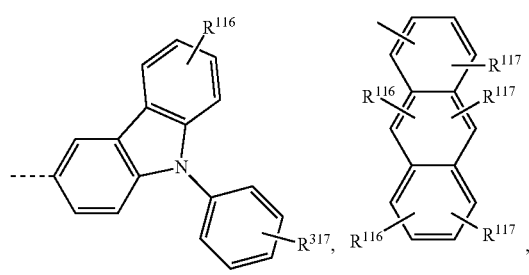

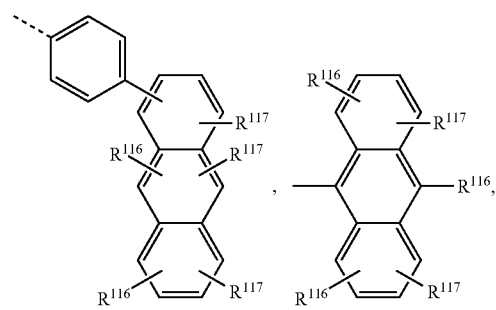

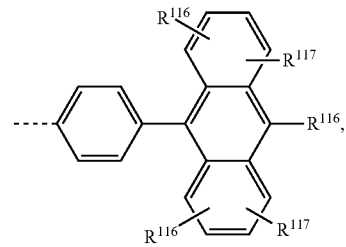

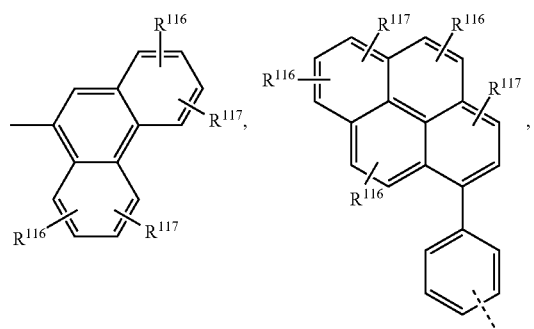

-continued

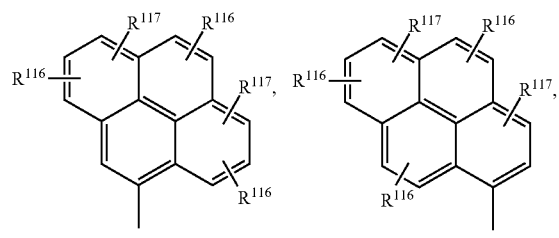

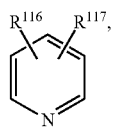

$C_1$-$C_{18}$alkoxy, $C_1$-$C_{18}$alkoxy which is substituted by E and/or interrupted by D,

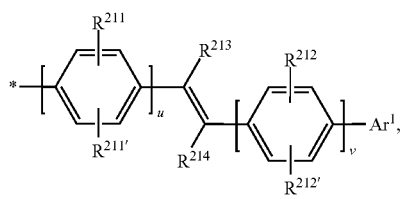

or -$L^1$-$NR^{26}R^{26'}$,
$L^1$ is a single bond,

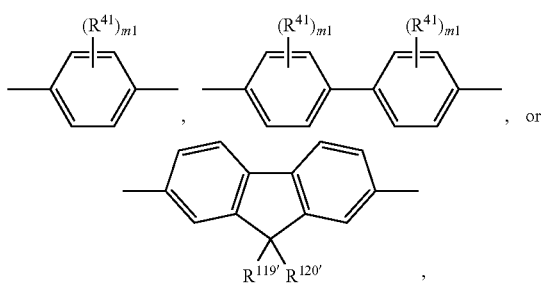

m1 is 0, or 1;
$R^{4'}$ is hydrogen, or a group

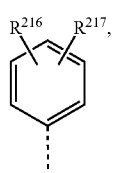

u is 0, or 1; v is 0, or 1;
$R^{211}$, $R^{211'}$, $R^{212}$ and $R^{212'}$ are independently of each other H, or $C_1$-$C_{18}$alkyl,
$R^{213}$ and $R^{214}$ are independently of each other H, or $C_1$-$C_{18}$alkyl, $Ar^1$ is —$NR^{25'}R^{26'}$,

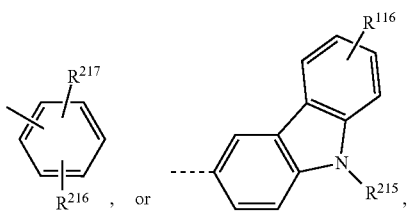

$R^{25'}$ and $R^{26'}$ are independently of each other

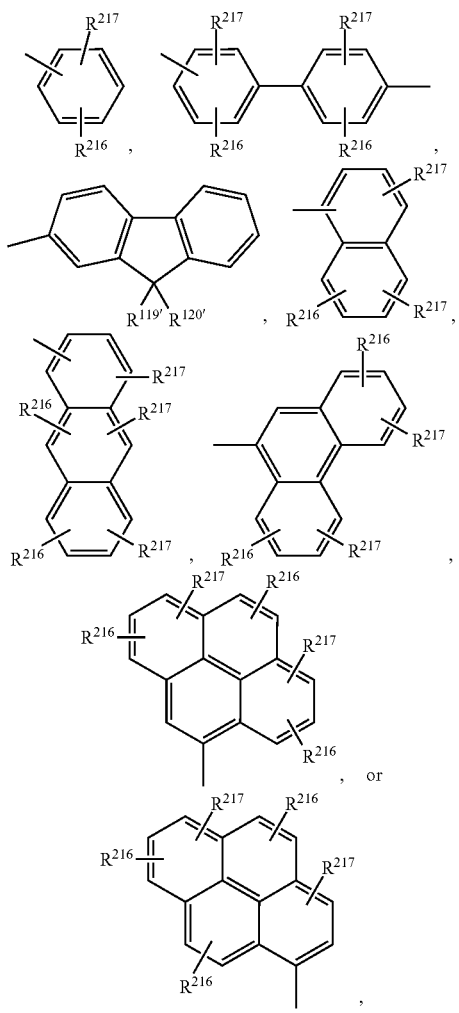

or $R^{25'}$ and $R^{26'}$ together with the nitrogen atom to which they are bonded form a group

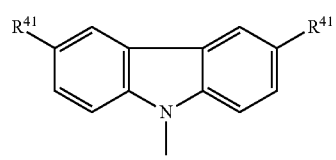

wherein
$R^{41}$ is H, or $C_1$-$C_8$alkyl, and
$R^{116}$ and $R^{117}$ are independently of each other $C_1$-$C_{25}$alkyl, which may optionally be interrupted by —O—, or $C_1$-$C_{25}$alkoxy, 1-naphthyl, 2-naphthyl, phenyl, or pyridine, which may optionally be substituted by $C_1$-$C_{25}$alkyl, which may optionally be interrupted by —O—, or phenyl; and $R^{119'}$ and $R^{120'}$ are independently of each other $C_1$-$C_{25}$alkyl, or $C_1$-$C_{25}$alkyl, which is substituted by E and/or interrupted by D, $R^{216}$ and $R^{217}$ are independently of each other $C_1$-$C_{25}$alkyl, which may optionally be interrupted by —O—, or $C_1$-$C_{25}$alkoxy, $R^{316}$ and $R^{317}$ have the meaning of $R^{116}$ and are preferably $C_1$-$C_{25}$alkyl, which may optionally be interrupted by —O—, or $C_1$-$C_{25}$alkoxy, D is —O—; or —$NR^{25}$—, E is —$OR^{29}$; —$NR^{25}R^{26}$; —CN, or F; $R^{29}$; $R^{25}$, and $R^{26}$ are as defined in claim 2.

6. An electronic device according to claim 3, comprising a compound of formula

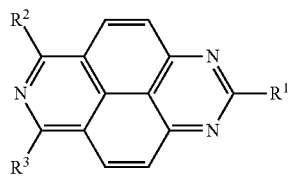

| Cpd. | $R^1$ | $R^2$ | $R^3$ |
|---|---|---|---|
| A-1 | phenyl | phenyl | phenyl |
| A-2 | 2-naphthyl | 2-naphthyl | 2-naphthyl |
| A-3 | 1-naphthyl | 1-naphthyl | 1-naphthyl |
| A-4 | biphenyl | biphenyl | biphenyl |
| A-5 | 2-naphthyl | phenyl | phenyl |
| A-6 | pyrenyl | phenyl | phenyl |
| A-7 | 2,3-diphenylquinoxalinyl | phenyl | phenyl |

-continued
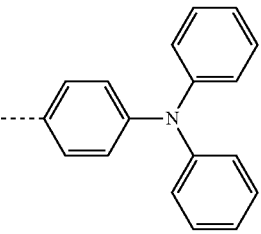
| Cpd. | R¹ | R² | R³ |
|---|---|---|---|
| A-8 | 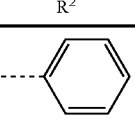 | 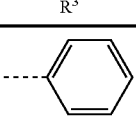 | 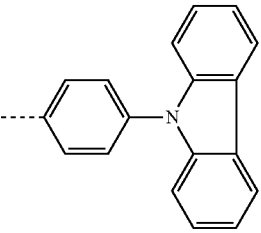 |
| A-9 | 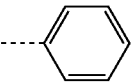 | 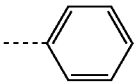 | 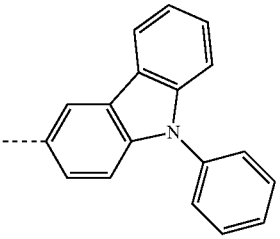 |
| A-10 | 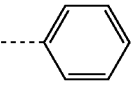 | 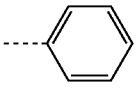 | 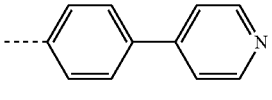 |
| A-11 | 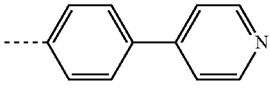 | 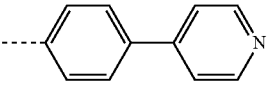 | 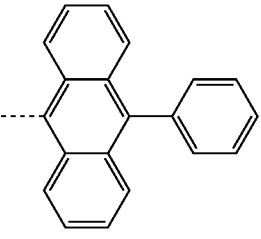 |
| A-12 | 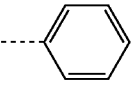 | 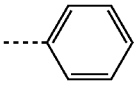 | 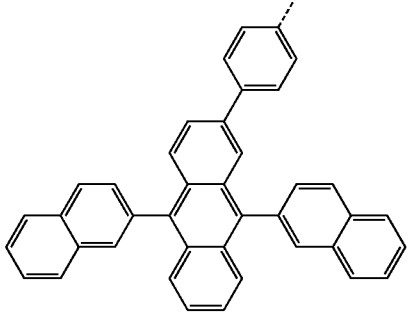 |
| A-13 | 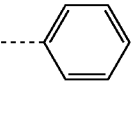 | 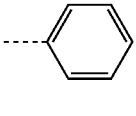 | 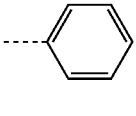 |

-continued

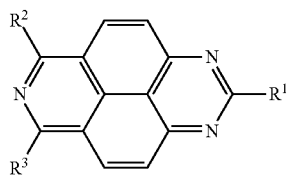

| Cpd. | R¹ | R² | R³ |
|---|---|---|---|
| A-14 | phenyl | 10-phenylanthracen-9-yl | phenyl |
| A-15 | phenyl | 2,6,10-tri(naphthalen-2-yl/p-tolyl)anthracen-9-yl | phenyl |
| A-16 | 4-(pyridin-3-yl)phenyl | 4-(pyridin-3-yl)phenyl | 4-(pyridin-3-yl)phenyl |
| A-17 | 4-(pyridin-4-yl)phenyl | 4-(pyridin-4-yl)phenyl | 4-(pyridin-4-yl)phenyl |
| A-18 | 4-(pyridin-2-yl)phenyl | 4-(pyridin-2-yl)phenyl | 4-(pyridin-2-yl)phenyl |
| A-19 | 4-(N-naphthalen-1-yl-N-phenylamino)phenyl | phenyl | phenyl |
| A-20 | 4-(N(CH₃)₂)phenyl | 4-(N(CH₃)₂)phenyl | 4-(N(CH₃)₂)phenyl | and/or a compound of formula

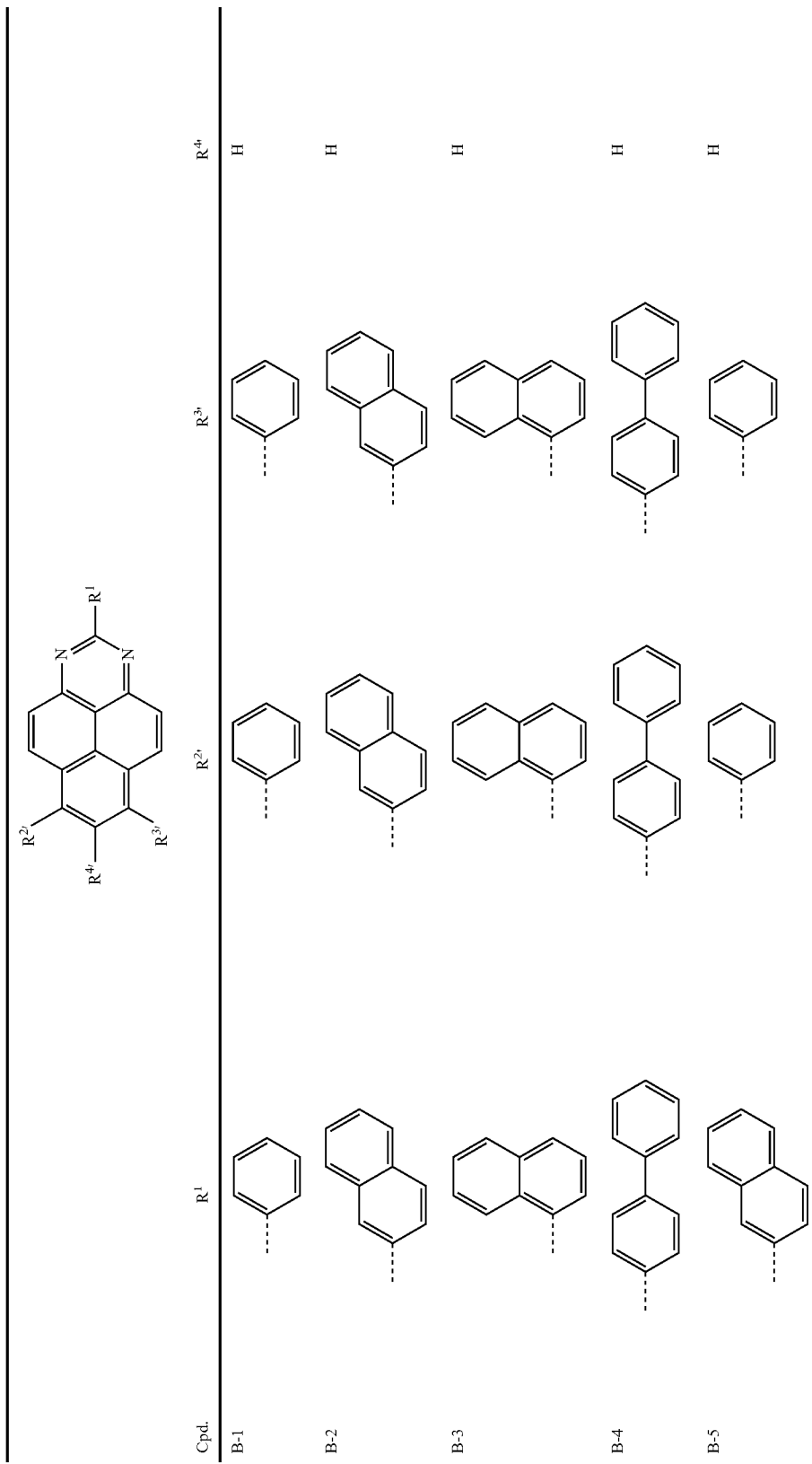

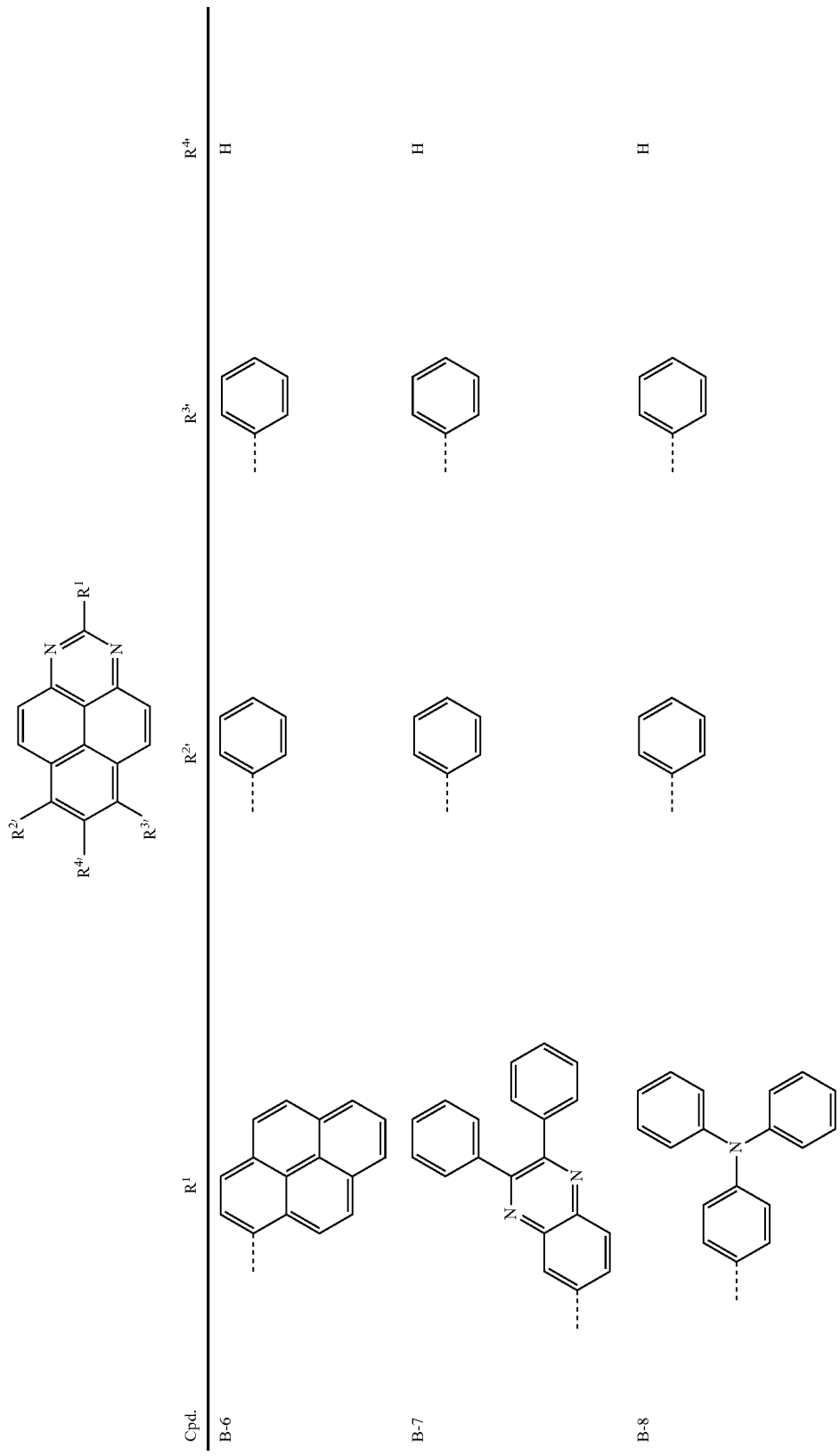

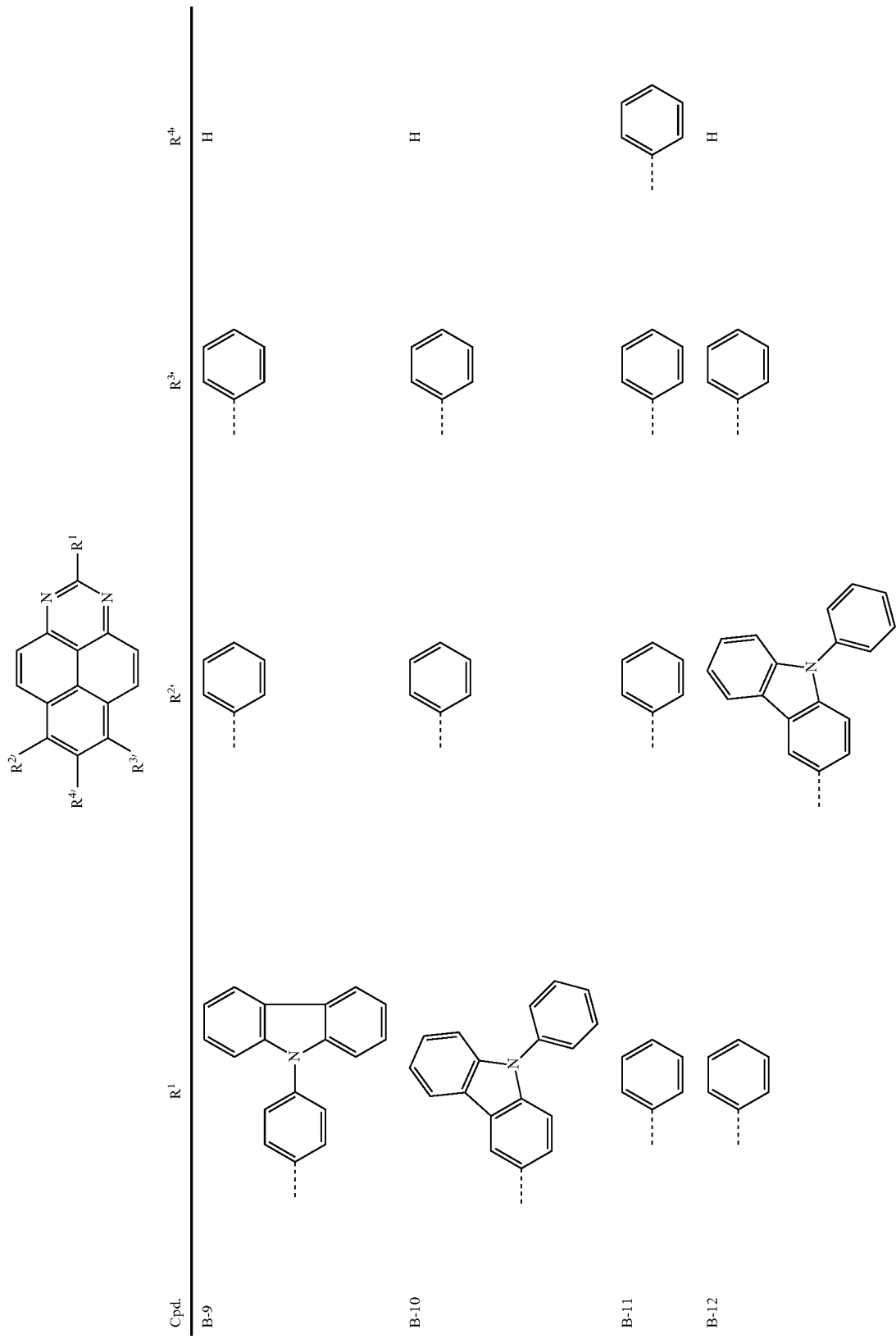

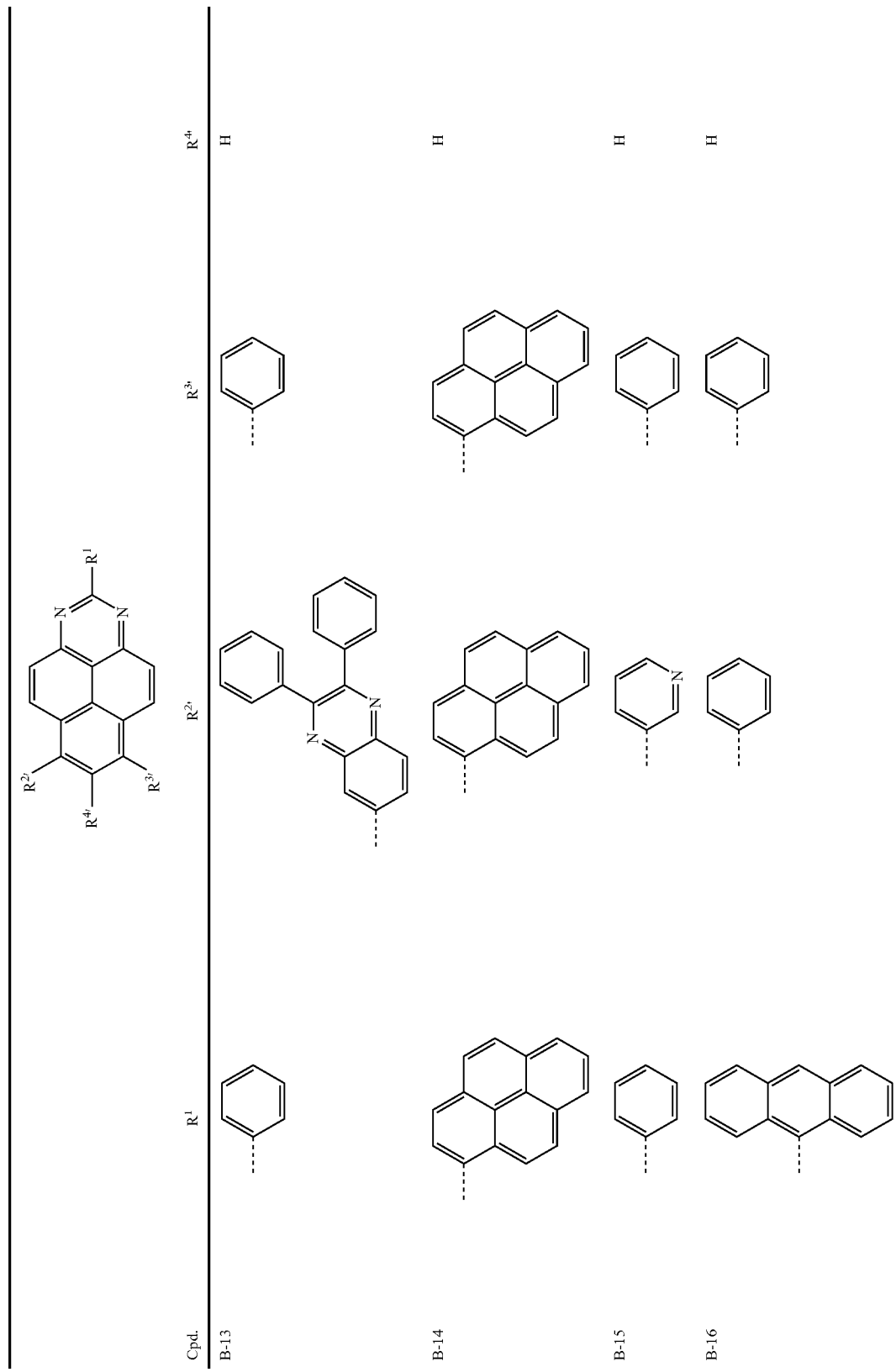

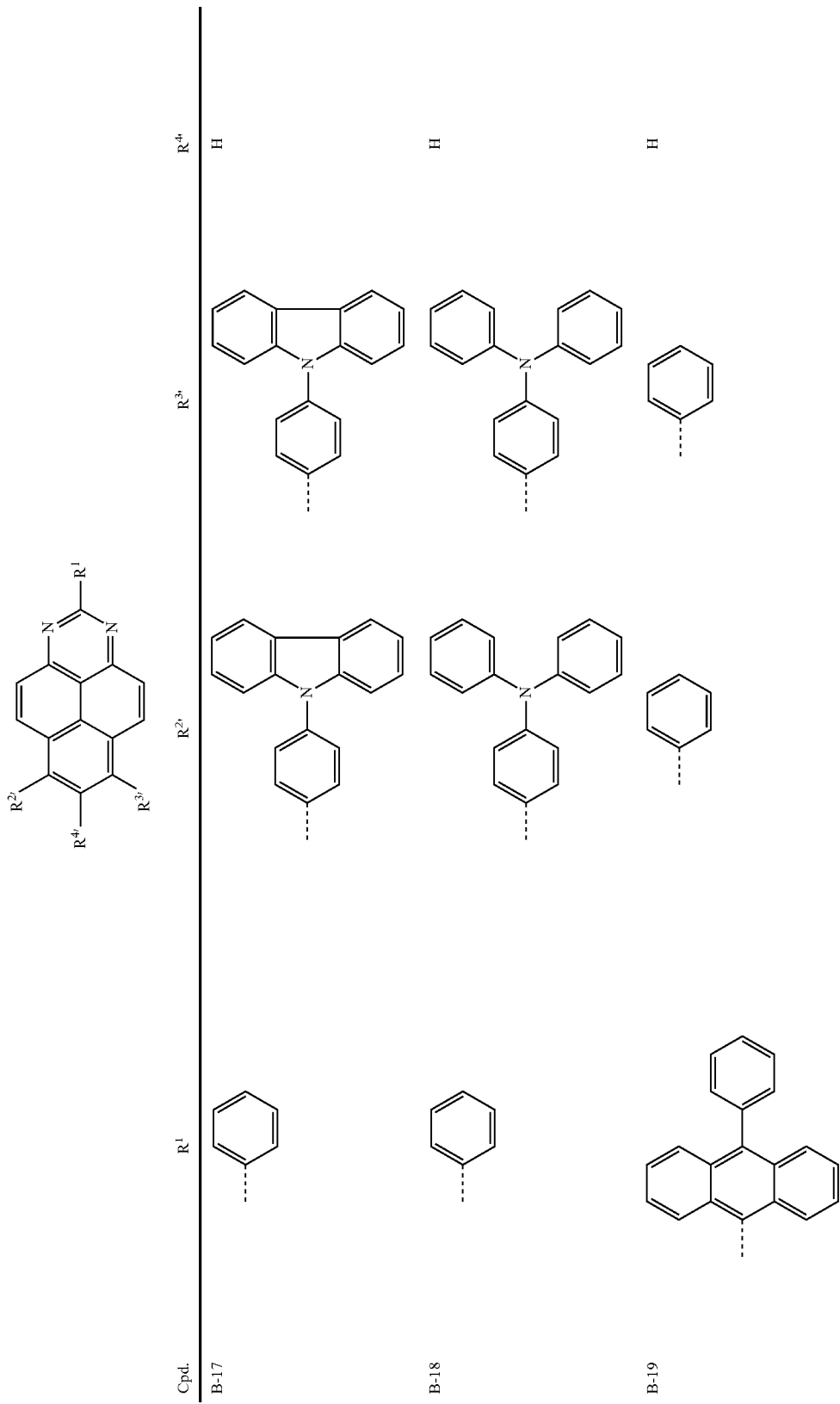

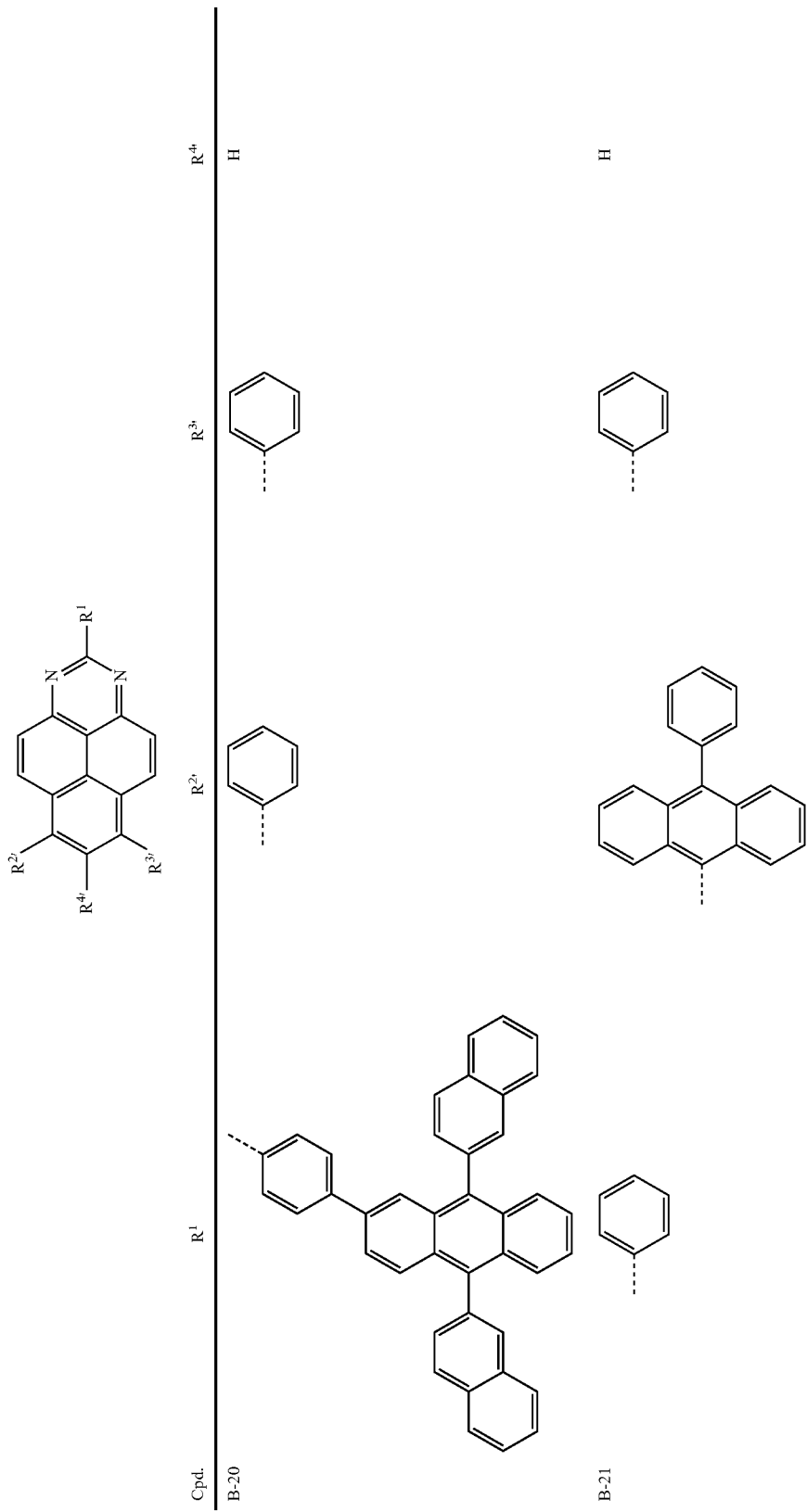

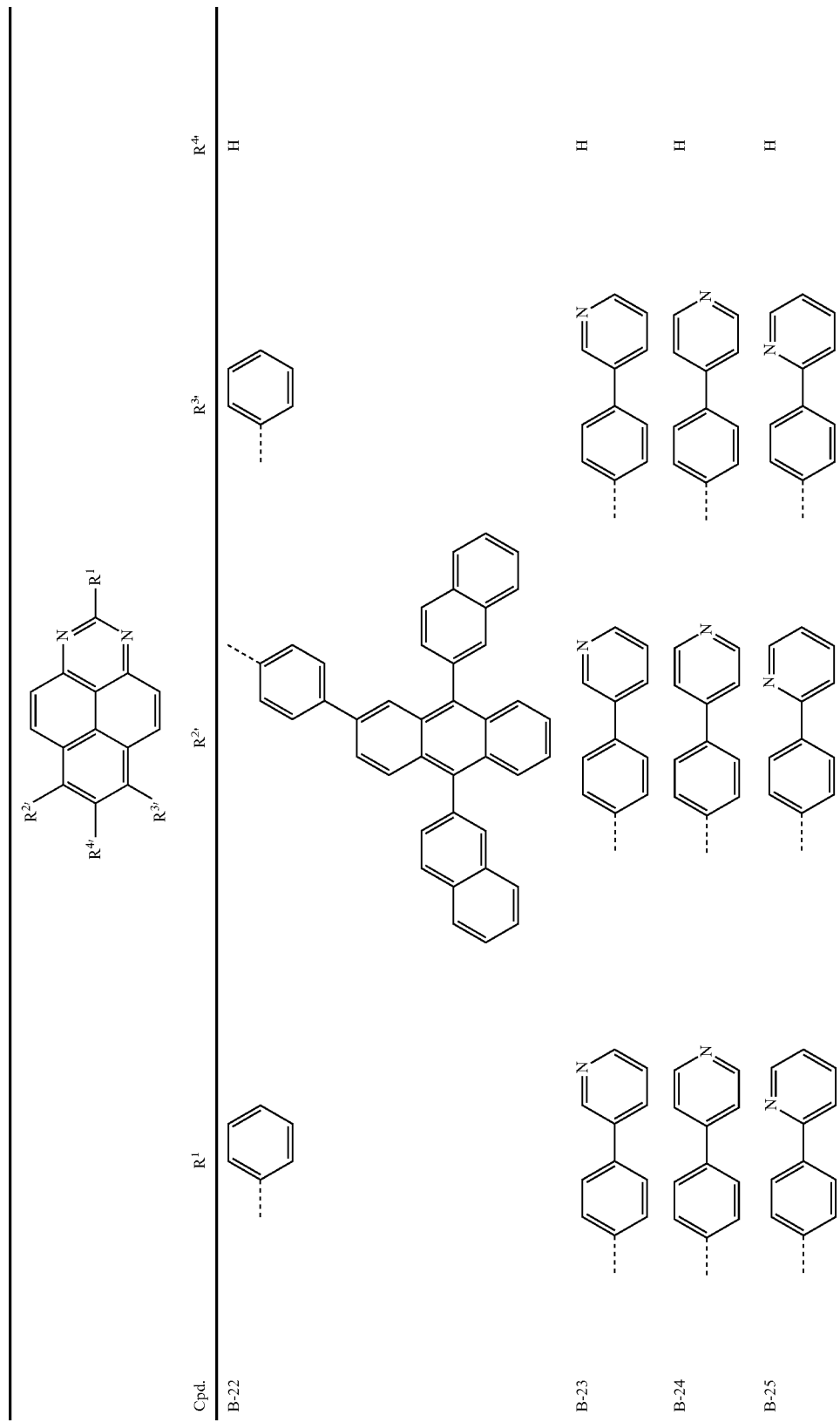

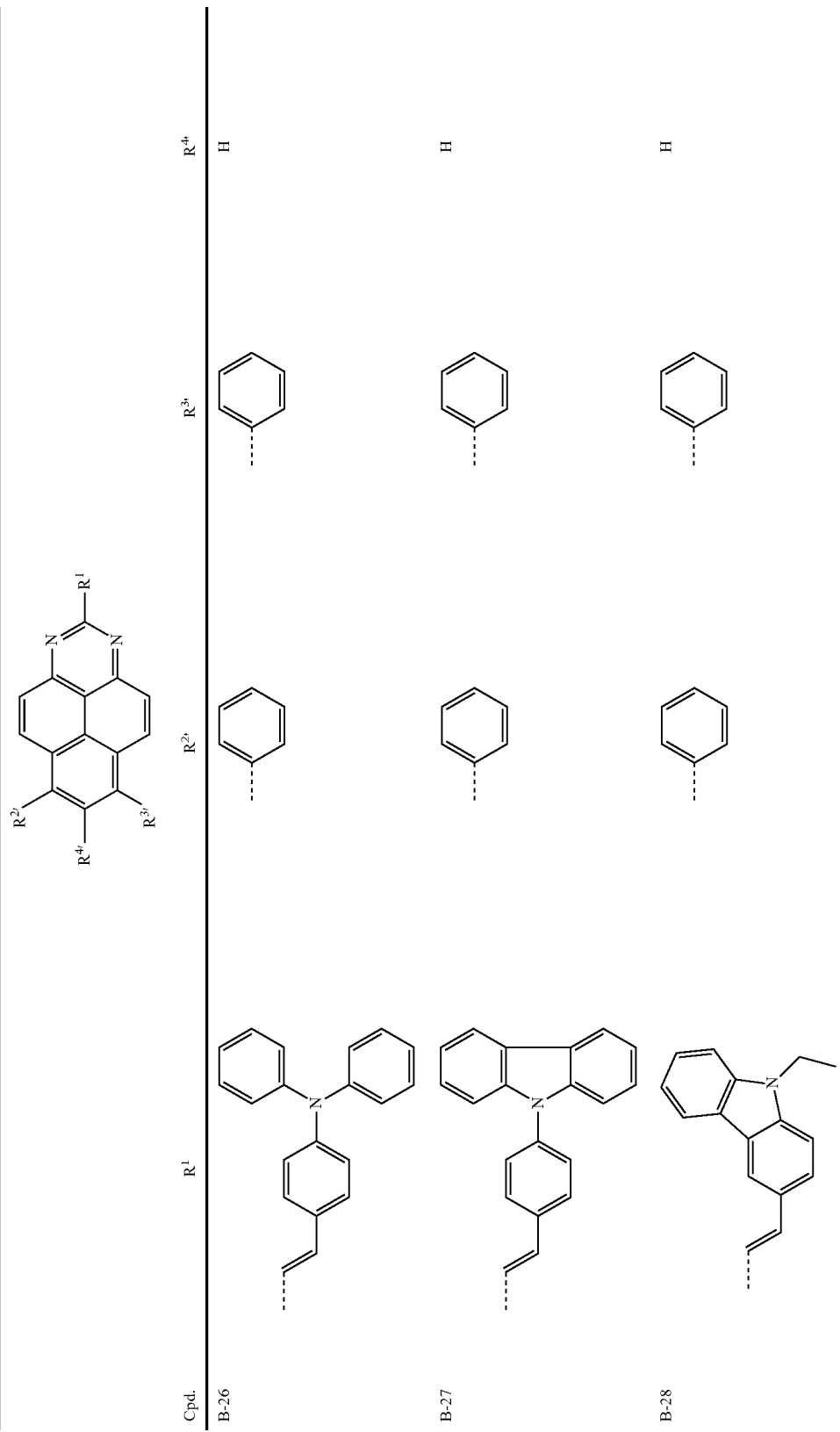

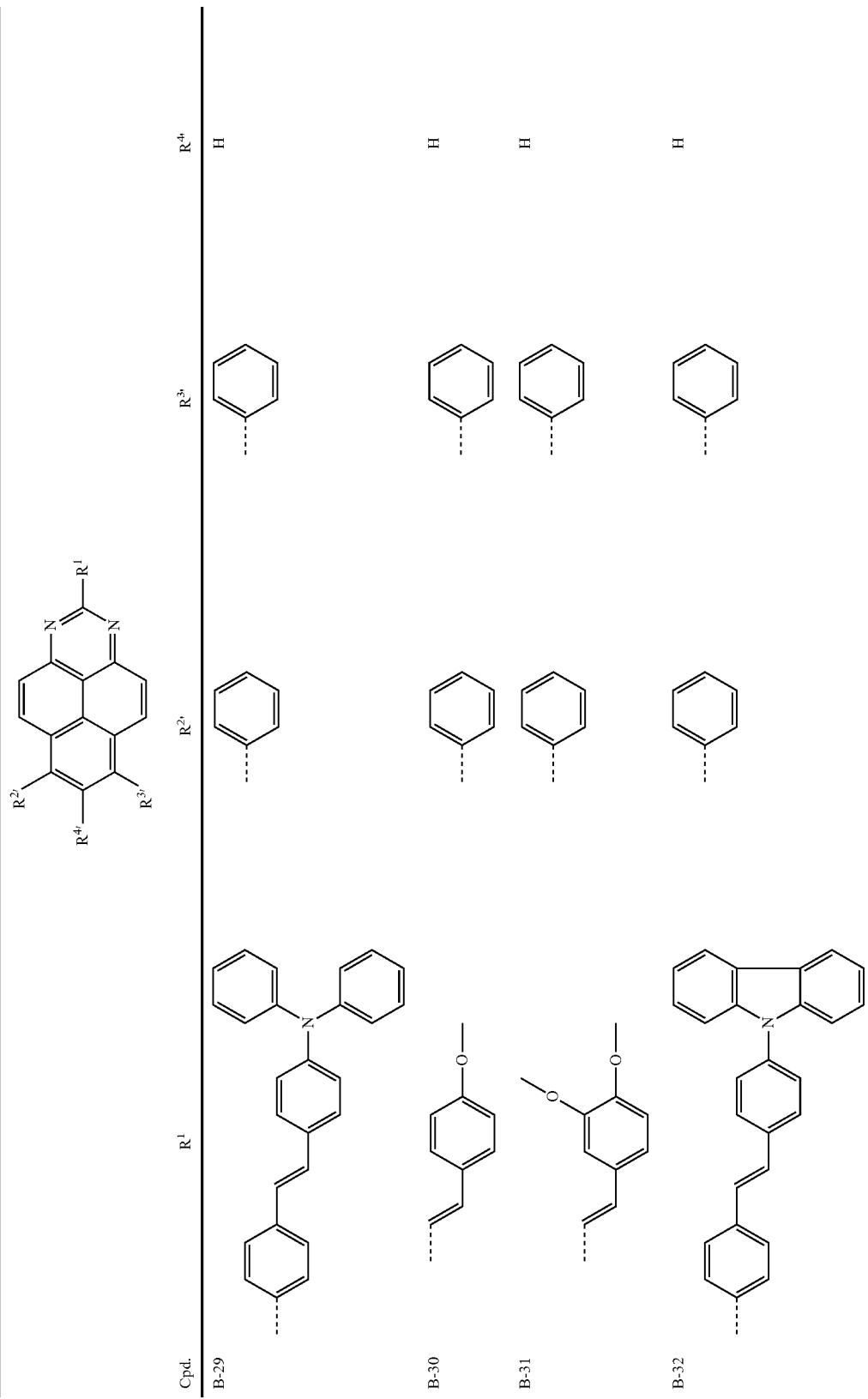

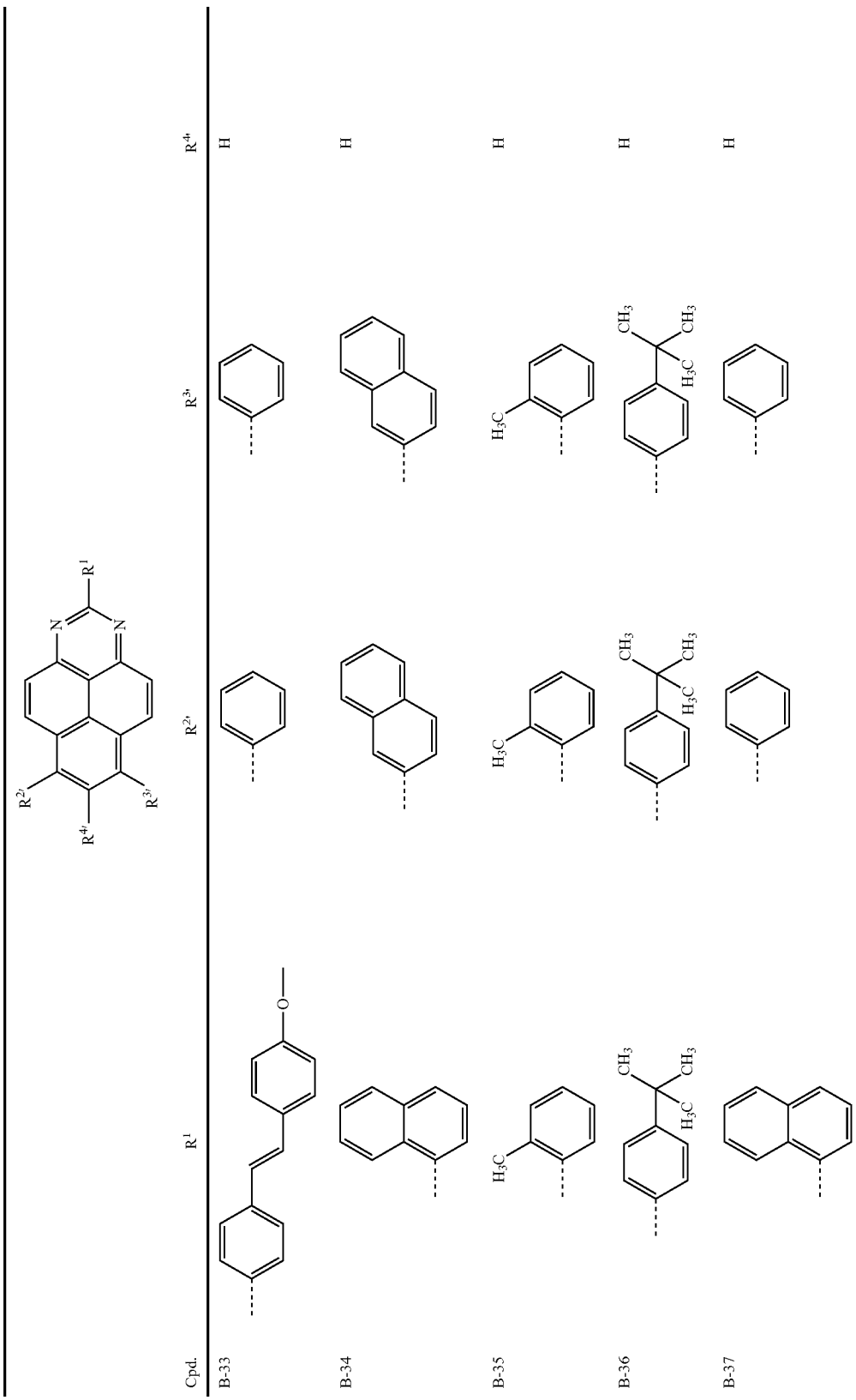

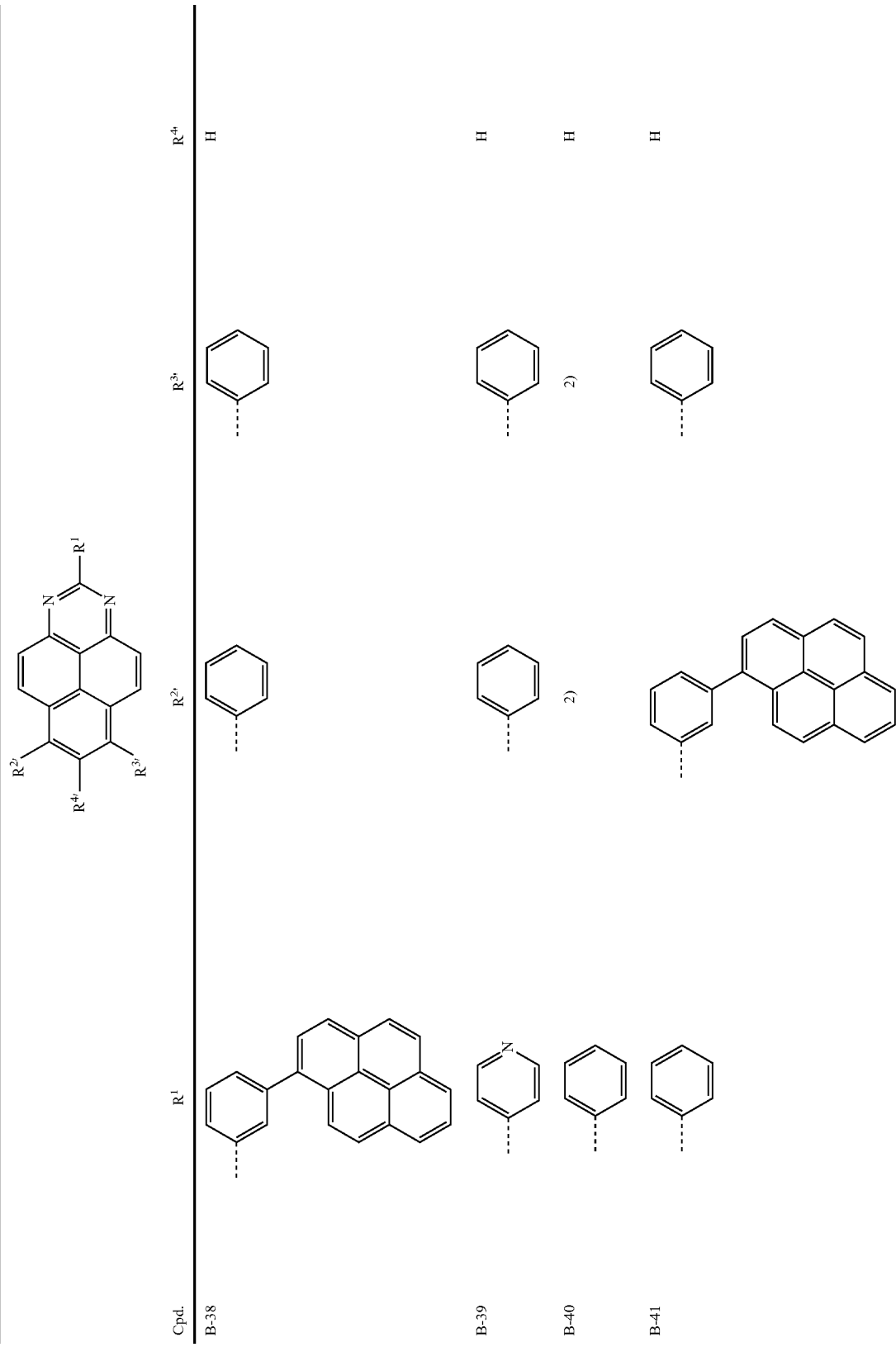

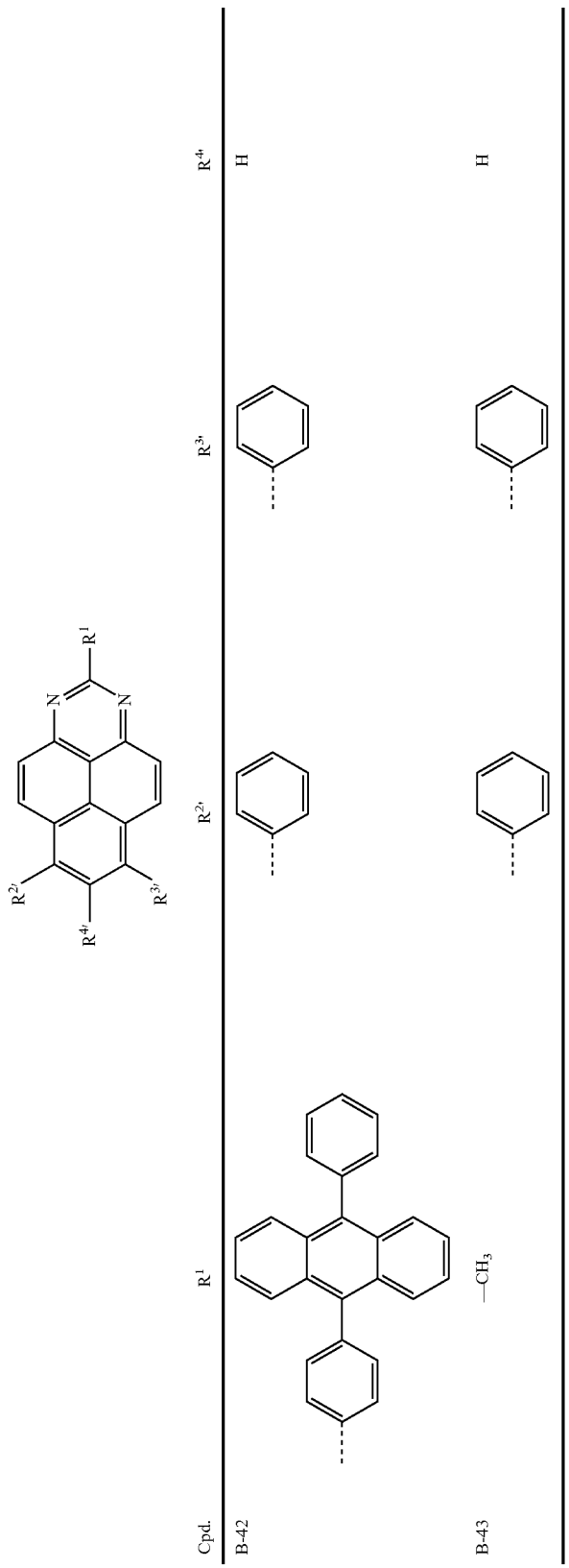

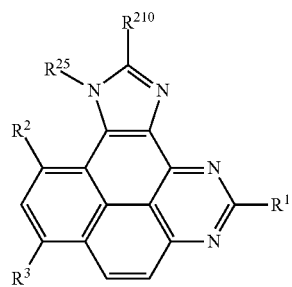
| Cpd. | R¹ | R² | R³ | R²⁵ | R²¹⁰ |
|---|---|---|---|---|---|
| E-1 | phenyl | phenyl | phenyl | phenyl | phenyl |
| E-2 | phenyl | phenyl | phenyl | phenyl | 1-naphthyl |
| E-3 | 1-naphthyl | phenyl | phenyl | phenyl | phenyl |
| E-4 | phenyl | phenyl | phenyl | phenyl | 4-biphenyl |
| E-5 | 1) | phenyl | phenyl | phenyl | phenyl |
| E-6 | 2) | phenyl | phenyl | phenyl | phenyl |
| E-7 | 3) | phenyl | phenyl | phenyl | phenyl |
| E-8 | phenyl | phenyl | phenyl | phenyl | 4) |

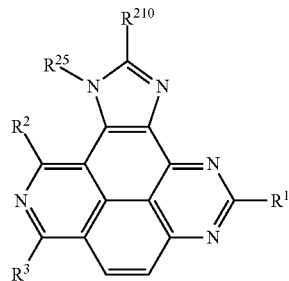
| Cpd. | R¹ | R² | R³ | R²⁵ | R²¹⁰ |
|---|---|---|---|---|---|
| F-1 | Ph | Ph | Ph | Ph | Ph |
| F-2 | Ph | Ph | Ph | Ph | 4-CN-C₆H₄ |
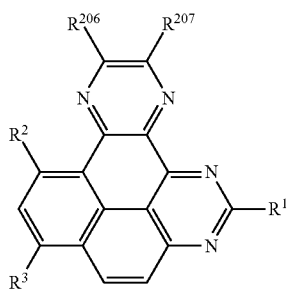
| Cpd. | R¹ | R² | R³ | R²⁰⁶ | R²⁰⁷ |
|---|---|---|---|---|---|
| G-1 | Ph | Ph | Ph | CN | CN |
| G-2 | Ph | Ph | Ph | H | CH₃ |
| G-3 | Ph | Ph | Ph | H | H |
| G-4 | Ph | Ph | Ph | 5) | 5) |
| G-5 | Ph | Ph | Ph | 6) | 6) |

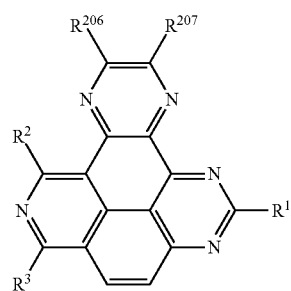
| Cpd. | R¹ | R² | R³ | $R^{206}$ | $R^{207}$ |
|---|---|---|---|---|---|
| H-1 | phenyl | phenyl | phenyl | H | H |
| H-2 | phenyl | phenyl | phenyl | 5) | 5) |
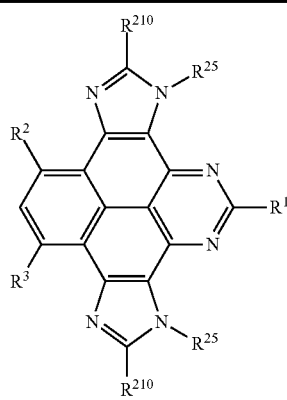
| Cpd. | R¹ | R² | R³ | $R^{25}$ | $R^{210}$ |
|---|---|---|---|---|---|
| I-1 | phenyl | pyridyl | phenyl | phenyl | phenyl |
| I-2 | 1-naphthyl | phenyl | phenyl | phenyl | phenyl |
| I-3 | 2-naphthyl | phenyl | phenyl | phenyl | phenyl |
| I-4 | phenyl | phenyl | phenyl | phenyl | 1-naphthyl |

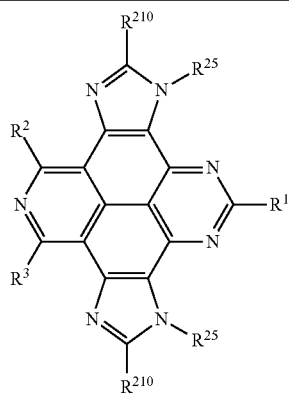
| Cpd. | R¹ | R² | R³ | R²⁵ | R²¹⁰ |
|---|---|---|---|---|---|
| J-1 | phenyl | phenyl | phenyl | phenyl | phenyl |
| J-2 | 1-naphthyl | phenyl | phenyl | phenyl | phenyl |
| J-3 | 2-naphthyl | phenyl | phenyl | phenyl | phenyl |
| J-4 | phenyl | phenyl | phenyl | phenyl | 1-naphthyl |
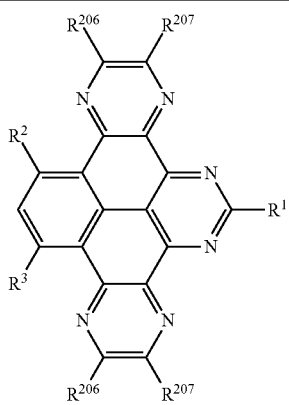
| Cpd. | R¹ | R² | R³ | R²⁰⁶ | R²⁰⁷ |
|---|---|---|---|---|---|
| K-1 | phenyl | phenyl | phenyl | 5) | 5) |

-continued
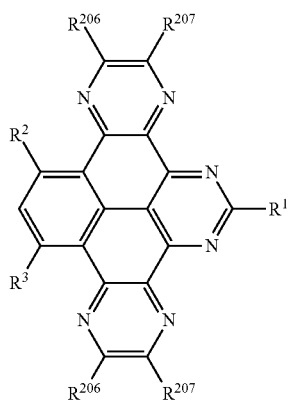
| Cpd. | R¹ | R² | R³ | R²⁰⁶ | R²⁰⁷ |
|---|---|---|---|---|---|
| K-2 | phenyl | phenyl | phenyl | CN | CN |
| K-3 | phenyl | phenyl | phenyl | H | CH₃ |
| K-4 | phenyl | phenyl | phenyl | CH₃ | H |
| K-5 | phenyl | phenyl | phenyl | H | H |
| K-6 | 3) | pyridyl | phenyl | H | H |
| K-7 | 7) | phenyl | phenyl | H | H |
| K-8 | 1-naphthyl | phenyl | phenyl | 5) | 5) |

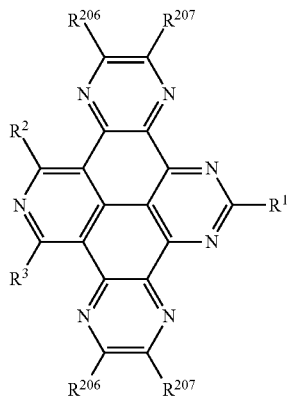
| Cpd. | R¹ | R² | R³ | R²⁰⁶ | R²⁰⁷ |
|---|---|---|---|---|---|
| L-1 | phenyl | phenyl | phenyl | 5) | 5) |
| L-2 | phenyl | phenyl | phenyl | CH₃ | H |
1) 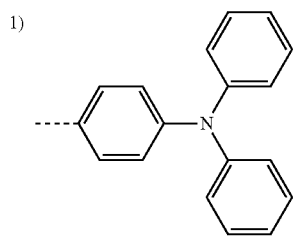
2) 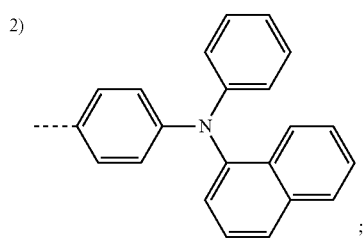
3) 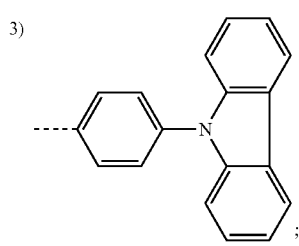
-continued
4) 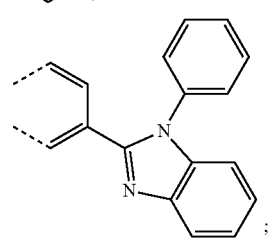
5) R²⁰⁶ and R²⁰⁷ together form a group ;
6) R²⁰⁶ and R²⁰⁷ together form a group 

7)

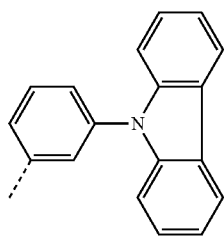

7. An electronic device according to claim 1, comprising a compound of formula

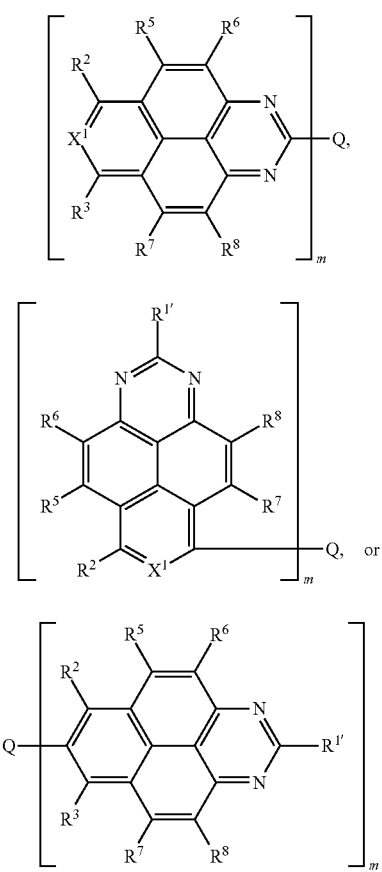

(IIIa)
(IIIb)
(IIIc)

wherein m, $R^{1'}$, $R^2$, $R^3$, $X^1$, $R^5$, $R^6$, $R^7$ and $R^8$ are as defined in claim 1, and Q is a group of formula

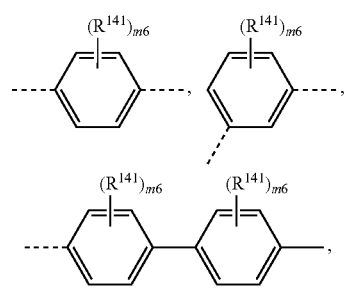

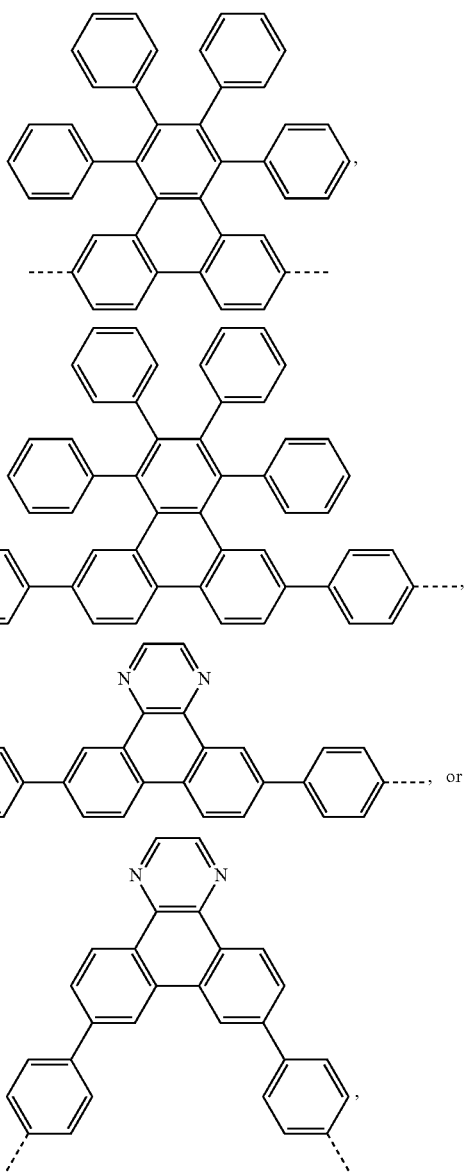

wherein $R^{141}$ can be the same or different at each occurrence and is $C_1$-$C_{25}$alkyl, which may optionally be interrupted by —O—, or $C_1$-$C_{25}$alkoxy; m6 is 0, 1, or 2.

8. An electronic device according to claim 7, comprising a compound of formula

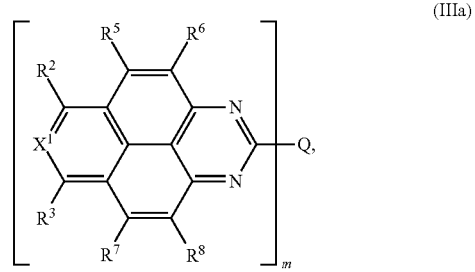

(IIIa)

-continued

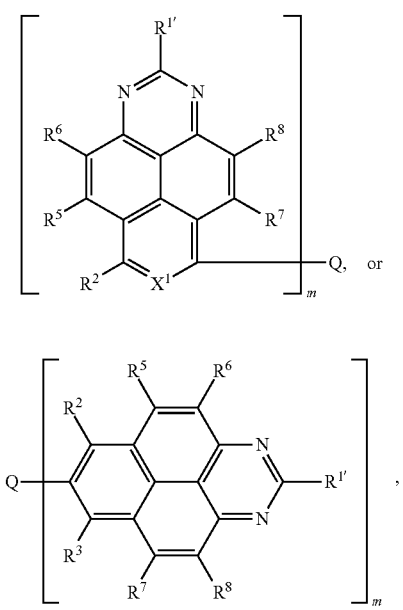

wherein $X^1$ is CH, or N,
$R^5$, $R^6$, $R^7$ and $R^8$ are hydrogen,
$R^{1'}$, $R^2$, $R^3$ are independently of each other

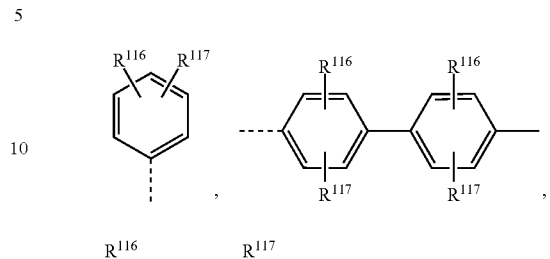

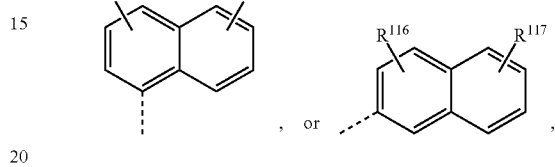

$R^{116}$ and $R^{117}$ are independently of each other $C_1$-$C_{25}$alkyl, which may optionally be interrupted by —O—, or $C_1$-$C_{25}$alkoxy, and
and Q and m are as defined in claim 7.

9. An electronic device according to claim 8, comprising a compound of formula

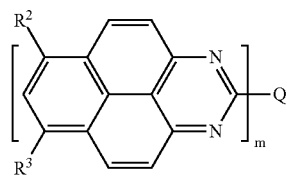

| Cpd. | $R^2$ | $R^3$ | Q | m |
|---|---|---|---|---|
| C-1 | phenyl | phenyl | phenyl (meta) | 2 |
| C-2 | phenyl | phenyl | phenyl (para) | 2 |
| C-3 | phenyl | phenyl | hexaphenyltriphenylene | 2 |

-continued
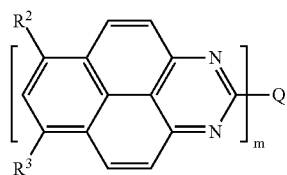
| Cpd. | R² | R³ | Q | m |
|---|---|---|---|---|
| C-4 | phenyl | phenyl | hexaphenyltriphenylene-bis(phenylene) | 2 |
| C-5 | phenyl | phenyl | dibenzo[a,c]phenazine-bis(phenylene) | 2 |
| C-6 | phenyl | phenyl | dibenzo[a,c]phenazine-bis(phenylene) | 2 |
| C-6 | phenyl | phenyl | phenylene | 2 | and/or a compound of formula
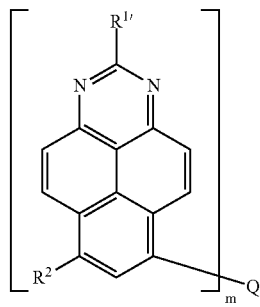
| Cpd. | R² | R¹' | Q | m |
|---|---|---|---|---|
| D-1 | phenyl | phenyl | m-phenylene | 2 |
| D-2 | phenyl | phenyl | p-phenylene | 2 |
| D-3 | phenyl | phenyl | tetraphenyl-triphenylene | 2 |
| D-4 | phenyl | phenyl | tetraphenyl-triphenylene-bis(phenylene) | 2 |
| D-5 | phenyl | phenyl | pyrazino-triphenylene-bis(phenylene) | 2 |

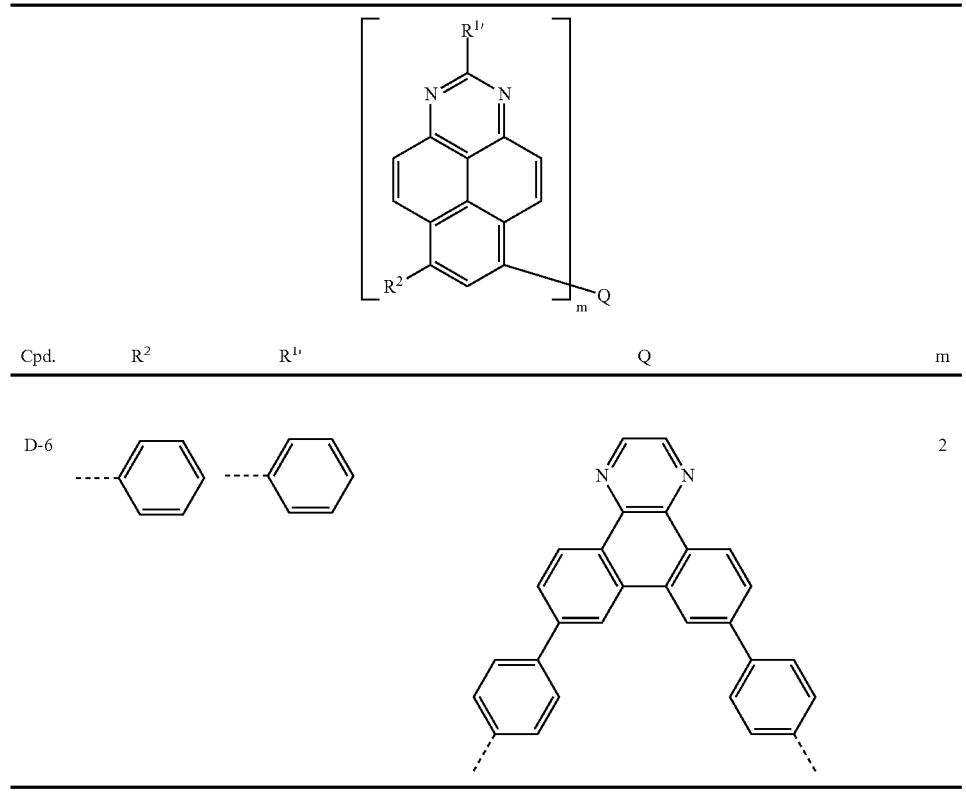

| Cpd. | R² | R¹' | Q | m |
|------|----|----|---|---|
| D-6 | 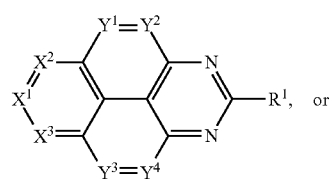 | | 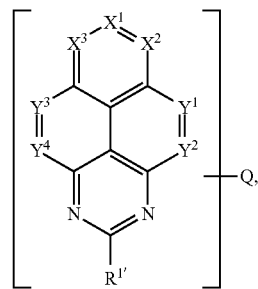 | 2 |

10. Electronic device according to claim 1, wherein the electronic device is an electroluminescent device.

11. Electronic device according to claim 10, comprising a cathode, an anode, and there between a light emitting layer containing a host material and a phosphorescent light-emitting material, wherein the host material is a compound of formula I, or III according to claim 1.

12. Electronic device according to claim 10, comprising a cathode, an anode, and an electron transport material, wherein the electron transport material is, or comprises a compound of formula I, or III according to claim 1.

13. Electronic device according to claim 10, comprising a cathode, an anode, and an emitting layer, wherein the emitting layer consists of, or comprises a compound of formula I, or III according to claim 1.

14. Electrophotographic photoreceptors, photoelectric converters, solar cells, image sensors, dye lasers and electroluminescent devices comprise the compounds of formula I, or III according to claim 1.

15. A compound of formula (I)

$$\begin{array}{c}\text{structure with } Y^1=Y^2, X^2, X^1, X^3, Y^3=Y^4, R^1 \end{array}$$

or (III)

$$\begin{array}{c}\text{structure with } X^1, X^2, X^3, Y^1, Y^2, Y^3, Y^4, R^{1\prime}, Q \end{array}$$

wherein
$Y^1, Y^2, Y^3, Y^4, X^1, X^2$ and $X^3$ are independently each other N, or $CR^4$,
with the proviso that at least one of the groups $X^1, X^2$ and $X^3$ is a group $CR^4$,
$R^1$ is F, $-SiR^{100}R^{101}R^{102}$, or an organic substituent,
$R^{1\prime}$ and $R^4$ are independently of each other hydrogen, F, $-SiR^{100}R^{101}R^{102}$, or an organic substituent, or
any of the substituents $R^1, R^{1\prime}$ and $R^4$, which are adjacent to each other, together form an aromatic, or heteroaromatic ring, or ring system, which can optionally be substituted,
m is an integer of 1 to 6, and
$R^{100}, R^{101}$ and $R^{102}$ are independently of each other a $C_1$-$C_8$alkyl group, a $C_6$-$C_{24}$aryl group, or a $C_7$-$C_{12}$aralkyl group, which may optionally be substituted, and Q is a linking group; with the proviso that in the compound of formula III at least one of the substituents $R^{1\prime}$, or $R^4$ is a group Q and with the further proviso that the following compounds 1 to 12 are excluded:

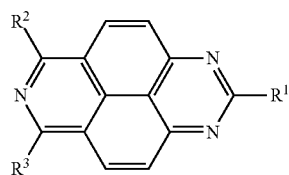
| Cpd. | R¹ | R² | R³ |
|---|---|---|---|
| 1 | phenyl | phenyl | phenyl |
| 2 | 4-Br-phenyl | 4-Br-phenyl | 4-Br-phenyl |
| 3 | 4-NO₂-phenyl | 4-NO₂-phenyl | 4-NO₂-phenyl |
| 4 | —CH₃ | H | H |
| 5 | phenyl | H | H |
| 6 | —CH₃ | —CH₃ | —CH₃ |
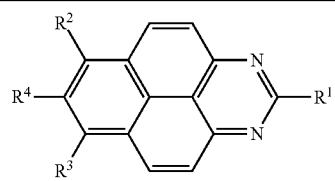
| Cpd. | R¹ | R² | R³ | R⁴ |
|---|---|---|---|---|
| 7 | —CH₃ | phenyl | phenyl | H |
| 8 | phenyl | phenyl | phenyl | H |
| 9 | —CH₃ | H | —CH₃ | —CO₂C₂H₅ |
| 10 | phenyl | phenyl | phenyl | H |
| 11 | —CH₃ | —CH₃ | phenyl | H |
| 12 | phenyl | —CH₃ | phenyl | H |

16. A compound of formula
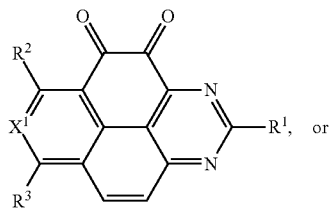
(VIa)
or
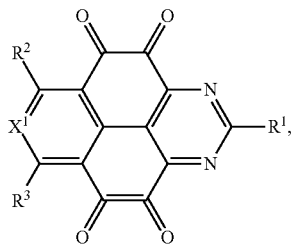
(VIb)
wherein $X^1$, $R^1$, $R^2$ and $R^3$ are as defined in claim 2.
* * * * *